(12) United States Patent
Wieland et al.

(10) Patent No.: US 7,510,859 B2
(45) Date of Patent: Mar. 31, 2009

(54) SUBTILISIN VARIANTS WITH IMPROVED PERHYDROLASE ACTIVITY

(75) Inventors: Susanne Wieland, Dormagen-Zons (DE); Laura Polanyi-Bald, Frechen (DE); Inken Prueser, Duesseldorf (DE); Regina Stehr, Neuss (DE); Karl-Heinz Maurer, Erkrath (DE)

(73) Assignee: Henkel Kommanditgesellschaft Auf Aktien, Duesseldorf (DE)

( * ) Notice: Subject to any disclaimer, the term of this patent is extended or adjusted under 35 U.S.C. 154(b) by 426 days.

(21) Appl. No.: 11/156,062

(22) Filed: Jun. 17, 2005

(65) Prior Publication Data
US 2005/0281773 A1 Dec. 22, 2005

Related U.S. Application Data

(63) Continuation of application No. PCT/EP03/14127, filed on Dec. 12, 2003.

(30) Foreign Application Priority Data
Dec. 20, 2002 (DE) ............... 102 60 903

(51) Int. Cl.
| C12N 9/16 | (2006.01) |
| C12N 15/55 | (2006.01) |
| C12N 15/74 | (2006.01) |
| C12N 15/75 | (2006.01) |
| A61Q 5/10 | (2006.01) |
| A61Q 11/02 | (2006.01) |
| C11D 3/386 | (2006.01) |
| C11D 3/395 | (2006.01) |
| C12P 7/02 | (2006.01) |
| C12N 9/54 | (2006.01) |
| C12N 15/70 | (2006.01) |
| A61K 8/38 | (2006.01) |
| A61Q 5/08 | (2006.01) |

(52) U.S. Cl. ................ 435/197; 435/132; 435/221; 435/252.3; 435/252.31; 435/252.35; 435/263; 435/320.1; 536/23.2; 424/401; 424/50; 424/62; 424/70.1; 510/116; 510/226; 510/300; 510/305; 8/406

(58) Field of Classification Search .................. None
See application file for complete search history.

(56) References Cited

U.S. PATENT DOCUMENTS

| 3,547,828 A | 12/1970 | Mansfield et al. |
| 3,707,535 A | 12/1972 | Lew |
| 3,772,269 A | 11/1973 | Lew |
| 3,839,318 A | 10/1974 | Mansfield |
| 3,985,923 A | 10/1976 | Basadur |
| 4,116,885 A | 9/1978 | Derstadt et al. |
| 4,172,887 A | 10/1979 | Vanlergerghe et al. |
| 4,349,772 A | 9/1982 | Weiss et al. |
| 4,820,439 A | 4/1989 | Rieck |
| 5,336,611 A * | 8/1994 | van Eekelen et al. ......... 435/221 |
| 5,364,554 A * | 11/1994 | Stanislowski et al. .. 252/186.38 |
| 5,382,377 A | 1/1995 | Raehse et al. |
| 5,614,161 A | 3/1997 | Wilkens et al. |
| 5,616,550 A | 4/1997 | Kruse et al. |
| 5,677,272 A | 10/1997 | Ghosh et al. |
| 5,705,169 A | 1/1998 | Stein et al. |
| 5,730,960 A | 3/1998 | Stein et al. |
| 5,783,545 A | 7/1998 | Paatz et al. |
| 5,925,609 A * | 7/1999 | Baillely et al. ............... 510/306 |
| 6,075,001 A | 6/2000 | Wilde |
| 6,187,055 B1 | 2/2001 | Kottwitz et al. |
| 6,193,960 B1 | 2/2001 | Metzger et al. |
| 6,287,841 B1 * | 9/2001 | Mulleners et al. ........... 435/221 |
| 6,379,394 B1 | 4/2002 | Chilou et al. |
| 6,407,247 B1 | 6/2002 | Habeck et al. |
| 6,432,661 B1 * | 8/2002 | Heitfeld et al. ............... 435/27 |
| 6,436,690 B1 * | 8/2002 | Brode et al. ................. 435/222 |
| 6,451,574 B1 * | 9/2002 | Brode et al. ................. 435/219 |
| 6,455,295 B1 * | 9/2002 | Brode et al. ................. 435/221 |
| 6,475,765 B1 * | 11/2002 | Brode et al. ................. 435/221 |
| 6,541,233 B1 | 4/2003 | Hillen et al. |
| 6,599,730 B1 * | 7/2003 | Brode et al. ................. 435/221 |
| 2004/0102349 A1 | 5/2004 | Breves et al. |
| 2004/0235125 A1 | 11/2004 | Kottwitz et al. |
| 2004/0259222 A1 | 12/2004 | Breves et al. |
| 2005/0003419 A1 | 1/2005 | Breves et al. |
| 2005/0003504 A1 | 1/2005 | Weber et al. |
| 2005/0003985 A1 | 1/2005 | Kottwitz et al. |
| 2005/0009167 A1 | 1/2005 | Weber et al. |
| 2005/0026269 A1 | 2/2005 | Kottwitz et al. |
| 2005/0043198 A1 | 2/2005 | Weber et al. |
| 2005/0049165 A1 | 3/2005 | Kottwitz et al. |
| 2005/0113273 A1 | 5/2005 | Weber et al. |
| 2005/0181446 A1 * | 8/2005 | Roggen et al. ............... 435/7.1 |

FOREIGN PATENT DOCUMENTS

CA 2 306 376 10/2000

(Continued)

OTHER PUBLICATIONS

E.L. Smith et al., J. Biol. Chem., vol. 243, pp. 2184-2191 (1968).

(Continued)

*Primary Examiner*—Rebecca E Prouty
*Assistant Examiner*—William W Moore
(74) *Attorney, Agent, or Firm*—Woodcock Washburn LLP

(57) ABSTRACT

The invention relates to novel perhydrolases, derived from the protease Carlsberg by amino acid exchange in positions 11, 15, 21, 38, 50, 54, 58, 77, 83, 89, 93, 96, 107, 117, 120, 134, 135, 136, 140, 147, 150, 154, 155, 160, 161, 171, 179, 180, 181, 194, 205, 208, 213, 216, 217, 238, 239, 251, 253, 257, and/or 261. The invention further relates to methods for production of said novel perhydrolases, products comprising said novel perhydrolases, particularly bodycare, haircare, shampoo, hair-dyeing, hair-bleaching, oral-care, dental-dare, dental-prosthesis-care, cosmetic, therapeutic (textile) washing, cleaning, rinsing, handwash, washing-up and dish-washing products, and corresponding applications of said novel perhydrolases.

23 Claims, No Drawings

FOREIGN PATENT DOCUMENTS

| | | |
|---|---|---|
| CA | 2 326 758 | 5/2001 |
| DE | 1 165 574 | 3/1964 |
| DE | 1 943 689 | 3/1970 |
| DE | 2 036 472 | 2/1971 |
| DE | 16 17 141 | 3/1973 |
| DE | 2 253 063 | 5/1973 |
| DE | 2 200 911 | 10/1973 |
| DE | 30 01 064 A1 | 7/1981 |
| DE | 33 24 258 A1 | 1/1984 |
| DE | 20 24 051 C3 | 5/1986 |
| DE | 28 57 292 C2 | 7/1992 |
| DE | 44 43 177 A1 | 6/1996 |
| DE | 196 01 063 A1 | 9/1996 |
| DE | 196 16 693 A1 | 11/1997 |
| DE | 196 16 767 A1 | 11/1997 |
| DE | 196 16 769 A1 | 11/1997 |
| DE | 196 16 770 A1 | 11/1997 |
| DE | 197 09 284 A1 | 9/1998 |
| DE | 197 12 033 A1 | 9/1998 |
| DE | 199 18 267 A1 | 10/2000 |
| DE | 199 56 382 A1 | 5/2001 |
| DE | 101 38 753 A1 | 3/2003 |
| EP | 0 077 167 A1 | 4/1983 |
| EP | 0 066 944 B1 | 11/1986 |
| EP | 0 272 033 A2 | 6/1988 |
| EP | 0 164 514 B1 | 6/1989 |
| EP | 0 253 567 B1 | 12/1990 |
| EP | 0 241 985 B1 | 1/1991 |
| EP | 0 472 042 A1 | 2/1992 |
| EP | 0 185 427 B1 | 3/1992 |
| EP | 0 274 907 B1 | 8/1992 |
| EP | 0 241 984 B1 | 3/1994 |
| EP | 0 486 592 B1 | 6/1994 |
| EP | 0 357 280 B1 | 2/1996 |
| EP | 0 642 576 B1 | 7/1996 |
| EP | 0 728 749 A2 | 8/1996 |
| EP | 0 525 239 B1 | 7/1997 |
| EP | 0 693 471 B1 | 1/1998 |
| EP | 0 694 521 B1 | 1/1998 |
| EP | 0 818 450 A1 | 1/1998 |
| EP | 0 736 084 B1 | 9/1998 |
| EP | 0 755 944 B1 | 10/2001 |
| FR | 2 252 840 | 6/1975 |
| GB | 962 919 | 7/1964 |
| GB | 1 154 730 | 6/1969 |
| GB | 1 333 475 | 10/1973 |
| GB | 1 377 092 | 12/1974 |
| GB | 2 165 856 | 4/1986 |
| WO | WO 96/28566 A2 | 9/1966 |
| WO | WO 91/02792 A1 | 3/1991 |
| WO | WO 92/21760 A1 | 12/1992 |
| WO | WO 94/27970 A1 | 12/1994 |
| WO | WO 94/28102 A1 | 12/1994 |
| WO | WO 94/28103 A1 | 12/1994 |
| WO | WO 95/00626 A1 | 1/1995 |
| WO | WO 95/14075 A1 | 5/1995 |
| WO | WO 95/14759 A1 | 6/1995 |
| WO | WO 95/17498 A1 | 6/1995 |
| WO | WO 95/23221 A1 | 8/1995 |
| WO | WO 95/32232 A1 | 11/1995 |
| WO | WO 96/29397 A1 | 9/1996 |
| WO | WO 96/34092 A2 | 10/1996 |
| WO | WO 97/14804 A1 | 4/1997 |
| WO | WO 97/18287 A1 | 5/1997 |
| WO | WO 97/24177 A1 | 7/1997 |
| WO | WO 97/25399 A1 | 7/1997 |
| WO | WO 97/31085 A1 | 8/1997 |
| WO | WO 98/12307 A1 | 3/1998 |
| WO | WO 98/45396 A1 | 10/1998 |
| WO | WO 99/06573 A1 | 2/1999 |
| WO | WO 99/20723 A2 | 4/1999 |
| WO | WO 99/49057 A1 | 9/1999 |
| WO | WO 99/63036 A1 | 12/1999 |
| WO | WO 99/63037 A1 | 12/1999 |
| WO | WO 99/63038 A1 | 12/1999 |
| WO | WO 99/63041 A1 | 12/1999 |
| WO | WO 02/10356 A2 | 2/2002 |
| WO | WO 02/44350 A2 | 6/2002 |
| WO | WO 02/088340 A2 | 11/2002 |
| WO | WO 03/002711 A2 | 1/2003 |
| WO | WO 03/054177 A2 | 3/2003 |
| WO | WO 03/038082 A2 | 5/2003 |
| WO | WO 03/054184 A1 | 7/2003 |
| WO | WO 03/054185 A1 | 7/2003 |
| WO | WO 03/055974 A2 | 7/2003 |
| WO | WO 03/056017 A2 | 7/2003 |

OTHER PUBLICATIONS

Jacobs et al., Nucl. Acids. Res., vol. 13, pp. 8913-8926 (1985).
Lipman et al., "Rapid and Sensitive Protein Similarity Searches", Science, vol. 227, pp. 1435-1441 (1985).
P. Finkel, "Formulierung kosmetischer Sonnenschutzmittel", SOFW-Journal, vol. 122, pp. 543-548 (1996).
Gornall et al., "Determination of Serum Proteins By Means of the Biurent Reaction", J. Biol. Chem., vol. 177, pp. 751-766 (1948).
Todd et al., "Volatile silicone fluids for cosmetic formulations", Cosmetics and Toiletries, vol. 91, pp. 29-32 (1976).
Lochhead et al., "Encyclopedia of Polymers and Thickeners for Cosmetics", Cosmetics & Toiletries, vol. 108, pp. 95-135 (1993).
Kosmetische Farbemittel der Farbstoffkommission der Deutschen Forschungsgemeinschaft, Verlag Chemie, Weihheim, pp. 81-106 (1984).
Kawamura et al., J. Bacteriol., vol. 160 (1), pp. 442-444 (1984).
Genbank Accession No. X91261, B, lichenformis mRNA for subtilisin Carlsberg isoform (strain 14353), sequence comparison with SEQ 23 and SEQ 24 (1995).
Genbank Accession No. S51909, *Bacillus subtilis* var. natto subtilisin NAT (aprN) gene, complete cds, Sequence comparison with SEQ 23 (2001).
Genbank Accession No. AF282895, *Bacillus lichenformis* isolate 837B KerA gene, partial cds, sequence comparison with SEQ 1 and SEQ 10 (2000).

* cited by examiner

SEQUENCE LISTING

```
<160> NUMBER OF SEQ ID NOS: 24

<210> SEQ ID NO 1
<211> LENGTH: 824
<212> TYPE: DNA
<213> ORGANISM: Artificial
<220> FEATURE:
<223> OTHER INFORMATION: Variant L89S/L216W/N217D of Subtilisin
      Carlsberg
<220> FEATURE:
<221> NAME/KEY: CDS
<222> LOCATION: (1)..(822)

<400> SEQUENCE: 1 gcg caa acc gtt cct tac ggc att cct ctc att aaa gcg gac aaa gtg      48
Ala Gln Thr Val Pro Tyr Gly Ile Pro Leu Ile Lys Ala Asp Lys Val
1               5                   10                  15 cag gct caa ggc ttt aag gga gcg aat gta aaa gta gcc gtc ctg gat      96
Gln Ala Gln Gly Phe Lys Gly Ala Asn Val Lys Val Ala Val Leu Asp
            20                  25                  30 aca gga atc caa gct tct cat ccg gac ttg aac gta gtc ggc gga gca      144
Thr Gly Ile Gln Ala Ser His Pro Asp Leu Asn Val Val Gly Gly Ala
```

-continued

```
                35                  40                  45
agc ttt gtg gct ggc gaa gct tat aac acc gac ggc aac gga cac ggc      192
Ser Phe Val Ala Gly Glu Ala Tyr Asn Thr Asp Gly Asn Gly His Gly
     50                  55                  60 aca cat gtt gcc ggt aca gta gct gcg ctt gac aat aca acg ggt gta      240
Thr His Val Ala Gly Thr Val Ala Ala Leu Asp Asn Thr Thr Gly Val
 65                  70                  75                  80 tta ggc gtt gcg cca agc gta tcc tcg tac gcg gtt aaa gta ctg aat      288
Leu Gly Val Ala Pro Ser Val Ser Ser Tyr Ala Val Lys Val Leu Asn
                 85                  90                  95 tca agc gga agc gga tca tac agc ggc att gta agc gga atc gag tgg      336
Ser Ser Gly Ser Gly Ser Tyr Ser Gly Ile Val Ser Gly Ile Glu Trp
            100                 105                 110 gcg act aca aac ggc atg gat gtt atc aat atg agc ctt ggg gga gca      384
Ala Thr Thr Asn Gly Met Asp Val Ile Asn Met Ser Leu Gly Gly Ala
        115                 120                 125 tca ggc tcg aca gcg atg aaa cag gca gtc gac aat gca tat gca aga      432
Ser Gly Ser Thr Ala Met Lys Gln Ala Val Asp Asn Ala Tyr Ala Arg
    130                 135                 140 ggg gtt gtc gtt gta gct gca gca ggg aac agc gga tct tca gga aac      480
Gly Val Val Val Val Ala Ala Ala Gly Asn Ser Gly Ser Ser Gly Asn
145                 150                 155                 160 acg aat aca att ggc tat cct gcg aaa tac gat tct gtc atc gct gtt      528
Thr Asn Thr Ile Gly Tyr Pro Ala Lys Tyr Asp Ser Val Ile Ala Val
                165                 170                 175 ggt gcg gta gac tct aac agc aac aga gct tca ttt tcc agc gtc gga      576
Gly Ala Val Asp Ser Asn Ser Asn Arg Ala Ser Phe Ser Ser Val Gly
            180                 185                 190 gca gag ctt gaa gtc atg gct cct ggc gca ggc gta tac agc act tac      624
Ala Glu Leu Glu Val Met Ala Pro Gly Ala Gly Val Tyr Ser Thr Tyr
        195                 200                 205 cca acg aac act tat gca aca tgg gac gga acg tca atg gct tct cct      672
Pro Thr Asn Thr Tyr Ala Thr Trp Asp Gly Thr Ser Met Ala Ser Pro
    210                 215                 220 cat gta gcg gga gca gca gct ttg atc ttg tca aaa cat ccg aac ctt      720
His Val Ala Gly Ala Ala Ala Leu Ile Leu Ser Lys His Pro Asn Leu
225                 230                 235                 240 tca gct tca caa gtc cgc aac cgt ctc tcc agc acg gcg act tat ttg      768
Ser Ala Ser Gln Val Arg Asn Arg Leu Ser Ser Thr Ala Thr Tyr Leu
                245                 250                 255 gga agc tcc ttc tac tat ggg aaa ggt ctg atc aat gtc gaa gct gcc      816
Gly Ser Ser Phe Tyr Tyr Gly Lys Gly Leu Ile Asn Val Glu Ala Ala
            260                 265                 270 gct caa ta                                                            824
Ala Gln
```

<210> SEQ ID NO 2
<211> LENGTH: 274
<212> TYPE: PRT
<213> ORGANISM: Artificial
<220> FEATURE:
<223> OTHER INFORMATION: Synthetic Construct

<400> SEQUENCE: 2

```
Ala Gln Thr Val Pro Tyr Gly Ile Pro Leu Ile Lys Ala Asp Lys Val
 1               5                  10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45
```

```
Ser Phe Val Ala Gly Glu Ala Tyr Asn Thr Asp Gly Asn Gly His Gly
     50                  55                  60

Thr His Val Ala Gly Thr Val Ala Ala Leu Asp Asn Thr Thr Gly Val
 65                  70                  75                  80

Leu Gly Val Ala Pro Ser Val Ser Ser Tyr Ala Val Lys Val Leu Asn
                 85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
    130                 135                 140

Gly Val Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
    195                 200                 205

Pro Thr Asn Thr Tyr Ala Thr Trp Asp Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 3
<211> LENGTH: 824
<212> TYPE: DNA
<213> ORGANISM: Artificial
<220> FEATURE:
<223> OTHER INFORMATION: Variant L216W/N217D of Subtilisin Carlsberg
<220> FEATURE:
<221> NAME/KEY: CDS
<222> LOCATION: (1)..(822)

<400> SEQUENCE: 3 gcg caa acc gtt cct tac ggc att cct ctc att aaa gcg gac aaa gtg      48
Ala Gln Thr Val Pro Tyr Gly Ile Pro Leu Ile Lys Ala Asp Lys Val
 1               5                  10                  15 cag gct caa ggc ttt aag gga gcg aat gta aaa gta gcc gtc ctg gat      96
Gln Ala Gln Gly Phe Lys Gly Ala Asn Val Lys Val Ala Val Leu Asp
             20                  25                  30 aca gga atc caa gct tct cat ccg gac ttg aac gta gtc ggc gga gca     144
Thr Gly Ile Gln Ala Ser His Pro Asp Leu Asn Val Val Gly Gly Ala
         35                  40                  45 agc ttt gtg gct ggc gaa gct tat aac acc gac ggc aac gga cac ggc     192
Ser Phe Val Ala Gly Glu Ala Tyr Asn Thr Asp Gly Asn Gly His Gly
     50                  55                  60 aca cat gtt gcc ggt aca gta gct gcg ctt gac aat aca acg ggt gta     240
Thr His Val Ala Gly Thr Val Ala Ala Leu Asp Asn Thr Thr Gly Val
 65                  70                  75                  80 tta ggc gtt gcg cca agc gta tcc ttg tac gcg gtt aaa gta ctg aat     288
```

```
Leu Gly Val Ala Pro Ser Val Ser Leu Tyr Ala Val Lys Val Leu Asn
                85                  90                  95 tca agc gga agc gga tca tac agc ggc att gta agc gga atc gag tgg      336
Ser Ser Gly Ser Gly Ser Tyr Ser Gly Ile Val Ser Gly Ile Glu Trp
            100                 105                 110 gcg act aca aac ggc atg gat gtt atc aat atg agc ctt ggg gga gca      384
Ala Thr Thr Asn Gly Met Asp Val Ile Asn Met Ser Leu Gly Gly Ala
        115                 120                 125 tca ggc tcg aca gcg atg aaa cag gca gtc gac aat gca tat gca aga      432
Ser Gly Ser Thr Ala Met Lys Gln Ala Val Asp Asn Ala Tyr Ala Arg
    130                 135                 140 ggg gtt gtc gtt gta gct gca gca ggg aac agc gga tct tca gga aac      480
Gly Val Val Val Val Ala Ala Ala Gly Asn Ser Gly Ser Ser Gly Asn
145                 150                 155                 160 acg aat aca att ggc tat cct gcg aaa tac gat tct gtc atc gct gtt      528
Thr Asn Thr Ile Gly Tyr Pro Ala Lys Tyr Asp Ser Val Ile Ala Val
                165                 170                 175 ggt gcg gta gac tct aac agc aac aga gct tca ttt tcc agc gtc gga      576
Gly Ala Val Asp Ser Asn Ser Asn Arg Ala Ser Phe Ser Ser Val Gly
            180                 185                 190 gca gag ctt gaa gtc atg gct cct ggc gca ggc gta tac agc act tac      624
Ala Glu Leu Glu Val Met Ala Pro Gly Ala Gly Val Tyr Ser Thr Tyr
        195                 200                 205 cca acg aac act tat gca aca tgg gac gga acg tca atg gct tct cct      672
Pro Thr Asn Thr Tyr Ala Thr Trp Asp Gly Thr Ser Met Ala Ser Pro
    210                 215                 220 cat gta gcg gga gca gca gct ttg atc ttg tca aaa cat ccg aac ctt      720
His Val Ala Gly Ala Ala Ala Leu Ile Leu Ser Lys His Pro Asn Leu
225                 230                 235                 240 tca gct tca caa gtc cgc aac cgt ctc tcc agc acg gcg act tat ttg      768
Ser Ala Ser Gln Val Arg Asn Arg Leu Ser Ser Thr Ala Thr Tyr Leu
                245                 250                 255 gga agc tcc ttc tac tat ggg aaa ggt ctg atc aat gtc gaa gct gcc      816
Gly Ser Ser Phe Tyr Tyr Gly Lys Gly Leu Ile Asn Val Glu Ala Ala
            260                 265                 270 gct caa ta                                                            824
Ala Gln <210> SEQ ID NO 4
<211> LENGTH: 274
<212> TYPE: PRT
<213> ORGANISM: Artificial
<220> FEATURE:
<223> OTHER INFORMATION: Synthetic Construct

<400> SEQUENCE: 4

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
```

```
                    100                 105                 110
Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
    130                 135                 140

Gly Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Trp Asp Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 5
<211> LENGTH: 824
<212> TYPE: DNA
<213> ORGANISM: Artificial
<220> FEATURE:
<223> OTHER INFORMATION: Variant T58A/L89S/L216W/N217D of Subtilisin
      Carlsberg
<220> FEATURE:
<221> NAME/KEY: CDS
<222> LOCATION: (1)..(822)

<400> SEQUENCE: 5 gcg caa acc gtt cct tac ggc att cct ctc att aaa gcg gac aaa gtg       48
Ala Gln Thr Val Pro Tyr Gly Ile Pro Leu Ile Lys Ala Asp Lys Val
1               5                   10                  15 cag gct caa ggc ttt aag gga gcg aat gta aaa gta gcc gtc ctg gat       96
Gln Ala Gln Gly Phe Lys Gly Ala Asn Val Lys Val Ala Val Leu Asp
                20                  25                  30 aca gga atc caa gct tct cat ccg gac ttg aac gta gtc ggc gga gca      144
Thr Gly Ile Gln Ala Ser His Pro Asp Leu Asn Val Val Gly Gly Ala
            35                  40                  45 agc ttt gtg gct ggc gaa gct tat aac gcc gac ggc aac gga cac ggc      192
Ser Phe Val Ala Gly Glu Ala Tyr Asn Ala Asp Gly Asn Gly His Gly
    50                  55                  60 aca cat gtt gcc ggt aca gta gct gcg ctt gac aat aca acg ggt gta      240
Thr His Val Ala Gly Thr Val Ala Ala Leu Asp Asn Thr Thr Gly Val
65                  70                  75                  80 tta ggc gtt gcg cca agc gta tcc tcg tac gcg gtt aaa gta ctg aat      288
Leu Gly Val Ala Pro Ser Val Ser Ser Tyr Ala Val Lys Val Leu Asn
                85                  90                  95 tca agc gga agc gga tca tac agc ggc att gta agc gga atc gag tgg      336
Ser Ser Gly Ser Gly Ser Tyr Ser Gly Ile Val Ser Gly Ile Glu Trp
            100                 105                 110 gcg aca aca aac ggc atg gat gtt atc aat atg agc ctt ggg gga gca      384
Ala Thr Thr Asn Gly Met Asp Val Ile Asn Met Ser Leu Gly Gly Ala
    115                 120                 125
```

-continued

| | | |
|---|---|---|
| tca ggc tcg aca gcg atg aaa cag gca gtc gac aat gca tat gca aga<br>Ser Gly Ser Thr Ala Met Lys Gln Ala Val Asp Asn Ala Tyr Ala Arg<br>130                       135                     140 | | 432 |
| ggg gtc gtc gtt gta gct gca gca ggg aac agc gga tct tca gga aac<br>Gly Val Val Val Ala Ala Ala Gly Asn Ser Gly Ser Ser Gly Asn<br>145                       150                     155                     160 | | 480 |
| acg aat aca att ggc tat cct gcg aaa tac gat tct gtc atc gct gtt<br>Thr Asn Thr Ile Gly Tyr Pro Ala Lys Tyr Asp Ser Val Ile Ala Val<br>                     165                     170                     175 | | 528 |
| ggt gcg gta gac tct aac agc aac aga gct tca ttt tcc agc gtc gga<br>Gly Ala Val Asp Ser Asn Ser Asn Arg Ala Ser Phe Ser Ser Val Gly<br>180                       185                     190 | | 576 |
| gca gag ctt gaa gtc atg gct cct ggc gca ggc gta tac agc act tac<br>Ala Glu Leu Glu Val Met Ala Pro Gly Ala Gly Val Tyr Ser Thr Tyr<br>             195                     200                     205 | | 624 |
| cca acg aac act tat gca aca tgg gac gga acg tca atg gct tct cct<br>Pro Thr Asn Thr Tyr Ala Thr Trp Asp Gly Thr Ser Met Ala Ser Pro<br>210                       215                     220 | | 672 |
| cat gta gcg gga gca gca gct ttg atc ttg tca aaa cat ccg aac ctt<br>His Val Ala Gly Ala Ala Ala Leu Ile Leu Ser Lys His Pro Asn Leu<br>225                       230                     235                     240 | | 720 |
| tca gct tca caa gtc cgc aac cgt ctc tcc agc acg gcg act tat ttg<br>Ser Ala Ser Gln Val Arg Asn Arg Leu Ser Ser Thr Ala Thr Tyr Leu<br>                     245                     250                     255 | | 768 |
| gga agc tcc ttc tac tat ggg aaa ggt ctg atc aat gtc gaa gct gcc<br>Gly Ser Ser Phe Tyr Tyr Gly Lys Gly Leu Ile Asn Val Glu Ala Ala<br>             260                     265                     270 | | 816 |
| gct caa ta<br>Ala Gln | | 824 |

<210> SEQ ID NO 6
<211> LENGTH: 274
<212> TYPE: PRT
<213> ORGANISM: Artificial
<220> FEATURE:
<223> OTHER INFORMATION: Synthetic Construct

<400> SEQUENCE: 6

Ala Gln Thr Val Pro Tyr Gly Ile Pro Leu Ile Lys Ala Asp Lys Val
1                   5                    10                   15

Gln Ala Gln Gly Phe Lys Gly Ala Asn Val Lys Val Ala Val Leu Asp
              20                    25                    30

Thr Gly Ile Gln Ala Ser His Pro Asp Leu Asn Val Val Gly Gly Ala
        35                    40                    45

Ser Phe Val Ala Gly Glu Ala Tyr Asn Ala Asp Gly Asn Gly His Gly
50                     55                    60

Thr His Val Ala Gly Thr Val Ala Ala Leu Asp Asn Thr Thr Gly Val
65                   70                    75                    80

Leu Gly Val Ala Pro Ser Val Ser Tyr Ala Val Lys Val Leu Asn
                  85                    90                    95

Ser Ser Gly Ser Gly Ser Tyr Ser Gly Ile Val Ser Gly Ile Glu Trp
              100                    105                   110

Ala Thr Thr Asn Gly Met Asp Val Ile Asn Met Ser Leu Gly Gly Ala
           115                    120                   125

Ser Gly Ser Thr Ala Met Lys Gln Ala Val Asp Asn Ala Tyr Ala Arg
130                       135                     140

Gly Val Val Val Ala Ala Ala Gly Asn Ser Gly Ser Ser Gly Asn
145                       150                     155                    160

```
Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Trp Asp Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 7
<211> LENGTH: 824
<212> TYPE: DNA
<213> ORGANISM: Artificial
<220> FEATURE:
<223> OTHER INFORMATION: Variant T58A/G117D/L216W/N217D of Subtilisin
      Carlsberg
<220> FEATURE:
<221> NAME/KEY: CDS
<222> LOCATION: (1)..(822)

<400> SEQUENCE: 7 gcg caa acc gtt cct tac ggc att cct ctc att aaa gcg gac aaa gtg    48
Ala Gln Thr Val Pro Tyr Gly Ile Pro Leu Ile Lys Ala Asp Lys Val
1               5                   10                  15 cag gct caa ggc ttt aag gga gcg aat gta aaa gta gcc gtc ctg gat    96
Gln Ala Gln Gly Phe Lys Gly Ala Asn Val Lys Val Ala Val Leu Asp
            20                  25                  30 aca gga atc caa gct tct cat ccg gac ttg aac gta gtc ggc gga gca   144
Thr Gly Ile Gln Ala Ser His Pro Asp Leu Asn Val Val Gly Gly Ala
        35                  40                  45 agc ttt gtg gct ggc gaa gct tat aac gcc gac ggc aac gga cac ggc   192
Ser Phe Val Ala Gly Glu Ala Tyr Asn Ala Asp Gly Asn Gly His Gly
    50                  55                  60 aca cat gtt gcc ggt aca gta gct gcg ctt gac aat aca acg ggt gta   240
Thr His Val Ala Gly Thr Val Ala Ala Leu Asp Asn Thr Thr Gly Val
65                  70                  75                  80 tta ggc gtt gcg cca agc gta tcc ttg tac gcg gtt aaa gta ctg aat   288
Leu Gly Val Ala Pro Ser Val Ser Leu Tyr Ala Val Lys Val Leu Asn
                85                  90                  95 tca agc gga agc gga tca tac agc ggc att gta agc gga atc gag tgg   336
Ser Ser Gly Ser Gly Ser Tyr Ser Gly Ile Val Ser Gly Ile Glu Trp
            100                 105                 110 gcg aca aca aac gac atg gat gtt atc aat atg agc ctt ggg gga gca   384
Ala Thr Thr Asn Asp Met Asp Val Ile Asn Met Ser Leu Gly Gly Ala
        115                 120                 125 tca ggc tcg aca gcg atg aaa cag gca gtc gac aat gca tat gca aga   432
Ser Gly Ser Thr Ala Met Lys Gln Ala Val Asp Asn Ala Tyr Ala Arg
    130                 135                 140 ggg gtc gtc gtt gta gct gca gca ggg aac agc gga tct tca gga aac   480
Gly Val Val Val Val Ala Ala Ala Gly Asn Ser Gly Ser Ser Gly Asn
145                 150                 155                 160 acg aat aca att ggc tat cct gcg aaa tac gat tct gtc atc gct gtt   528
Thr Asn Thr Ile Gly Tyr Pro Ala Lys Tyr Asp Ser Val Ile Ala Val
```

```
Thr Asn Thr Ile Gly Tyr Pro Ala Lys Tyr Asp Ser Val Ile Ala Val
            165                 170                 175 ggt gcg gta gac tct aac agc aac aga gct tca ttt tcc agc gtc gga      576
Gly Ala Val Asp Ser Asn Ser Asn Arg Ala Ser Phe Ser Ser Val Gly
            180                 185                 190 gca gag ctt gaa gtc atg gct cct ggc gca ggc gta tac agc act tac      624
Ala Glu Leu Glu Val Met Ala Pro Gly Ala Gly Val Tyr Ser Thr Tyr
            195                 200                 205 cca acg aac act tat gca aca tgg gac gga acg tca atg gct tct cct      672
Pro Thr Asn Thr Tyr Ala Thr Trp Asp Gly Thr Ser Met Ala Ser Pro
        210                 215                 220 cat gta gcg gga gca gca gct ttg atc ttg tca aaa cat ccg aac ctt      720
His Val Ala Gly Ala Ala Ala Leu Ile Leu Ser Lys His Pro Asn Leu
225                 230                 235                 240 tca gct tca caa gtc cgc aac cgt ctc tcc agc acg gcg act tat ttg      768
Ser Ala Ser Gln Val Arg Asn Arg Leu Ser Ser Thr Ala Thr Tyr Leu
                245                 250                 255 gga agc tcc ttc tac tat ggg aaa ggt ctg atc aat gtc gaa gct gcc      816
Gly Ser Ser Phe Tyr Tyr Gly Lys Gly Leu Ile Asn Val Glu Ala Ala
                260                 265                 270 gct caa ta                                                            824
Ala Gln <210> SEQ ID NO 8
<211> LENGTH: 274
<212> TYPE: PRT
<213> ORGANISM: Artificial
<220> FEATURE:
<223> OTHER INFORMATION: Synthetic Construct

<400> SEQUENCE: 8

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Ala Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Asp Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205
```

```
Pro Thr Asn Thr Tyr Ala Thr Trp Asp Gly Thr Ser Met Ala Ser Pro
    210                 215                 220

His Val Ala Gly Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
                260                 265                 270

Ala Gln

<210> SEQ ID NO 9
<211> LENGTH: 822
<212> TYPE: DNA
<213> ORGANISM: Artificial
<220> FEATURE:
<223> OTHER INFORMATION: Variant T58A/L89S/L216W/N217D of Subtilisin
      Carlsberg
<220> FEATURE:
<221> NAME/KEY: CDS
<222> LOCATION: (1)..(822)

<400> SEQUENCE: 9 gcg caa acc gtt cct tac ggc att cct ctc att aaa gcg gac aaa gtg     48
Ala Gln Thr Val Pro Tyr Gly Ile Pro Leu Ile Lys Ala Asp Lys Val
1               5                   10                  15 cag gct caa ggc ttt aag gga gcg aat gta aaa gta gcc gtc ctg gat     96
Gln Ala Gln Gly Phe Lys Gly Ala Asn Val Lys Val Ala Val Leu Asp
                20                  25                  30 aca gga atc caa gct tct cat ccg gac ttg aac gta gtc ggc gga gca    144
Thr Gly Ile Gln Ala Ser His Pro Asp Leu Asn Val Val Gly Gly Ala
            35                  40                  45 agc ttt gtg gct ggc gaa gct tat aac gcc gac ggc aac gga cac ggc    192
Ser Phe Val Ala Gly Glu Ala Tyr Asn Ala Asp Gly Asn Gly His Gly
        50                  55                  60 aca cat gtt gcc ggt aca gta gct gcg ctt gac aat aca acg ggt gtt    240
Thr His Val Ala Gly Thr Val Ala Ala Leu Asp Asn Thr Thr Gly Val
65                  70                  75                  80 tta ggc gtt gcg cca agc gta tcc tcg tac gcg gtt aaa gta ctg aat    288
Leu Gly Val Ala Pro Ser Val Ser Ser Tyr Ala Val Lys Val Leu Asn
                85                  90                  95 tca agc gga agc gga tca tac agc ggc att gta agc gga atc gag tgg    336
Ser Ser Gly Ser Gly Ser Tyr Ser Gly Ile Val Ser Gly Ile Glu Trp
            100                 105                 110 gcg aca aca aac ggc atg gat gtt atc aat atg agc ctt ggg gga gca    384
Ala Thr Thr Asn Gly Met Asp Val Ile Asn Met Ser Leu Gly Gly Ala
        115                 120                 125 tca ggc tcg aca gcg atg aaa cag gca gtc gac aat gca tat gca aga    432
Ser Gly Ser Thr Ala Met Lys Gln Ala Val Asp Asn Ala Tyr Ala Arg
130                 135                 140 ggg gtc gtc gtt gta gct gca gca ggg aac agc gga tct tca gga aac    480
Gly Val Val Val Val Ala Ala Ala Gly Asn Ser Gly Ser Ser Gly Asn
145                 150                 155                 160 acg aat aca att ggc tat cct gcg aaa tac gat tct gtc atc gct gtt    528
Thr Asn Thr Ile Gly Tyr Pro Ala Lys Tyr Asp Ser Val Ile Ala Val
                165                 170                 175 ggt gcg gta gac tct aac agc aac aga gct tca ttt tcc agc gtc gga    576
Gly Ala Val Asp Ser Asn Ser Asn Arg Ala Ser Phe Ser Ser Val Gly
            180                 185                 190 gca gag ctt gaa gtc atg gct cct ggc gca ggc gta tac agc act tac    624
Ala Glu Leu Glu Val Met Ala Pro Gly Ala Gly Val Tyr Ser Thr Tyr
        195                 200                 205
```

```
cca acg aac act tat gca aca tgg aac gga acg tca atg gct tct cct    672
Pro Thr Asn Thr Tyr Ala Thr Trp Asn Gly Thr Ser Met Ala Ser Pro
    210                 215                 220 cat gta gcg gga gca gca gct ttg atc ttg tca aaa cat ccg aac ctt    720
His Val Ala Gly Ala Ala Ala Leu Ile Leu Ser Lys His Pro Asn Leu
225                 230                 235                 240 tca gct tca caa gtc cgc aac cgt ctc tcc agc acg gcg act tat ttg    768
Ser Ala Ser Gln Val Arg Asn Arg Leu Ser Ser Thr Ala Thr Tyr Leu
                245                 250                 255 gga agc tcc ttc tac tat ggg aaa ggt ctg atc aat gtc gaa gct gcc    816
Gly Ser Ser Phe Tyr Tyr Gly Lys Gly Leu Ile Asn Val Glu Ala Ala
            260                 265                 270 gct caa                                                            822
Ala Gln
```

<210> SEQ ID NO 10
<211> LENGTH: 274
<212> TYPE: PRT
<213> ORGANISM: Artificial
<220> FEATURE:
<223> OTHER INFORMATION: Synthetic Construct

<400> SEQUENCE: 10

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Gly Gly Ala
        35                  40                  45

Ser Phe Val Ala Gly Glu Ala Tyr Asn Ala Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Trp Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
```

```
                    260                 265                 270
Ala Gln

<210> SEQ ID NO 11
<211> LENGTH: 824
<212> TYPE: DNA
<213> ORGANISM: Artificial
<220> FEATURE:
<223> OTHER INFORMATION: Variant T58A/L89S/N96D/L216W/N217D of
      Subtilisin Carlsberg
<220> FEATURE:
<221> NAME/KEY: CDS
<222> LOCATION: (1)..(822)

<400> SEQUENCE: 11 gcg cag acc gtt cct tac ggc att cct ctc att aaa gcg gac aaa gtg      48
Ala Gln Thr Val Pro Tyr Gly Ile Pro Leu Ile Lys Ala Asp Lys Val
1               5                   10                  15 cag gct caa ggc ttt aag gga gcg aat gta aaa gta gcc gtc ctg gat      96
Gln Ala Gln Gly Phe Lys Gly Ala Asn Val Lys Val Ala Val Leu Asp
            20                  25                  30 aca gga atc cag gct tct cat ccg gac ttg aac gta gtc ggc gga gca     144
Thr Gly Ile Gln Ala Ser His Pro Asp Leu Asn Val Val Gly Gly Ala
        35                  40                  45 agc ttt gtg gct ggc gaa gct tat aac gcc gac ggc aac gga cac ggc     192
Ser Phe Val Ala Gly Glu Ala Tyr Asn Ala Asp Gly Asn Gly His Gly
    50                  55                  60 aca cat gtt gcc ggt aca gta gct gcg ctc gac aat aca acg ggt gtt     240
Thr His Val Ala Gly Thr Val Ala Ala Leu Asp Asn Thr Thr Gly Val
65                  70                  75                  80 tta ggc gtt gcg cca agc gta tcc tcg tac gcg gtt aaa gta ctg gat     288
Leu Gly Val Ala Pro Ser Val Ser Ser Tyr Ala Val Lys Val Leu Asp
                85                  90                  95 tca agc gga agc gga tca tac agc ggc att gta agc gga atc gag tgg     336
Ser Ser Gly Ser Gly Ser Tyr Ser Gly Ile Val Ser Gly Ile Glu Trp
            100                 105                 110 gcg aca aca aac ggc atg gat gtt atc aat atg agc ctt ggg gga gca     384
Ala Thr Thr Asn Gly Met Asp Val Ile Asn Met Ser Leu Gly Gly Ala
        115                 120                 125 tca ggc tcg aca gcg atg aaa cag gca gtc gac aat gca tat gcg aga     432
Ser Gly Ser Thr Ala Met Lys Gln Ala Val Asp Asn Ala Tyr Ala Arg
    130                 135                 140 ggg gtc gtc gtt gta gct gca gca ggg aac agc gga tct tca gga aac     480
Gly Val Val Val Val Ala Ala Ala Gly Asn Ser Gly Ser Ser Gly Asn
145                 150                 155                 160 acg aat aca att ggc tat cct gcg aaa tac gat tct gtc atc gct gtt     528
Thr Asn Thr Ile Gly Tyr Pro Ala Lys Tyr Asp Ser Val Ile Ala Val
                165                 170                 175 ggt gcg gta gac tct aac agc aac aga gct tca ttt tcc agc gtc gga     576
Gly Ala Val Asp Ser Asn Ser Asn Arg Ala Ser Phe Ser Ser Val Gly
            180                 185                 190 gca gag ctt gaa gtc atg gct cct ggc gca ggc gta tac agc act tac     624
Ala Glu Leu Glu Val Met Ala Pro Gly Ala Gly Val Tyr Ser Thr Tyr
        195                 200                 205 cca acg aac act tat gca aca tgg aac gga acg tca atg gct tct cct     672
Pro Thr Asn Thr Tyr Ala Thr Trp Asn Gly Thr Ser Met Ala Ser Pro
    210                 215                 220 cat gta gcg gga gca gca gct ttg atc ttg tca aaa cat ccg aac ctt     720
His Val Ala Gly Ala Ala Ala Leu Ile Leu Ser Lys His Pro Asn Leu
225                 230                 235                 240 tca gct tca caa gtc cgc aac cgt ctc tcc agc acg gcg act tat ttg     768
```

```
Ser Ala Ser Gln Val Arg Asn Arg Leu Ser Ser Thr Ala Thr Tyr Leu
                245                 250                 255 gga agc tcc ttc tac tat ggg aaa ggt ctg atc aat gtc gaa gct gcc      816
Gly Ser Ser Phe Tyr Tyr Gly Lys Gly Leu Ile Asn Val Glu Ala Ala
            260                 265                 270 gct caa ta                                                           824
Ala Gln
```

<210> SEQ ID NO 12
<211> LENGTH: 274
<212> TYPE: PRT
<213> ORGANISM: Artificial
<220> FEATURE:
<223> OTHER INFORMATION: Synthetic Construct

<400> SEQUENCE: 12

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Ala Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Ser Tyr Ala Val Lys Val Leu Asp
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Trp Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln
```

<210> SEQ ID NO 13
<211> LENGTH: 824
<212> TYPE: DNA
<213> ORGANISM: Artificial
<220> FEATURE:

<223> OTHER INFORMATION: Variant T58A/L216W of Subtilisin Carlsberg
<220> FEATURE:
<221> NAME/KEY: CDS
<222> LOCATION: (1)..(822)

<400> SEQUENCE: 13

| gcg | caa | acc | gtt | cct | tac | ggc | att | cct | ctc | att | aaa | gcg | gac | aaa | gtg | 48 |
|---|---|---|---|---|---|---|---|---|---|---|---|---|---|---|---|---|
| Ala | Gln | Thr | Val | Pro | Tyr | Gly | Ile | Pro | Leu | Ile | Lys | Ala | Asp | Lys | Val | |
| 1 | | | | 5 | | | | | 10 | | | | | 15 | | |

| cag | gct | caa | ggc | ttt | aag | gga | gcg | aat | gta | aaa | gta | gcc | gtc | ctg | gat | 96 |
|---|---|---|---|---|---|---|---|---|---|---|---|---|---|---|---|---|
| Gln | Ala | Gln | Gly | Phe | Lys | Gly | Ala | Asn | Val | Lys | Val | Ala | Val | Leu | Asp | |
| | | | 20 | | | | | 25 | | | | | 30 | | | |

| aca | gga | atc | caa | gct | tct | cat | ccg | gac | ttg | aac | gta | gtc | ggc | gga | gca | 144 |
|---|---|---|---|---|---|---|---|---|---|---|---|---|---|---|---|---|
| Thr | Gly | Ile | Gln | Ala | Ser | His | Pro | Asp | Leu | Asn | Val | Val | Gly | Gly | Ala | |
| | | 35 | | | | | 40 | | | | | 45 | | | | |

| agc | ttt | gtg | gct | ggc | gaa | gct | tat | aac | gcc | gac | ggc | aac | gga | cac | ggc | 192 |
|---|---|---|---|---|---|---|---|---|---|---|---|---|---|---|---|---|
| Ser | Phe | Val | Ala | Gly | Glu | Ala | Tyr | Asn | Ala | Asp | Gly | Asn | Gly | His | Gly | |
| | 50 | | | | | 55 | | | | | 60 | | | | | |

| aca | cat | gtt | gcc | ggt | aca | gta | gct | gcg | ctt | gac | aat | aca | acg | ggt | gtt | 240 |
|---|---|---|---|---|---|---|---|---|---|---|---|---|---|---|---|---|
| Thr | His | Val | Ala | Gly | Thr | Val | Ala | Ala | Leu | Asp | Asn | Thr | Thr | Gly | Val | |
| 65 | | | | 70 | | | | | 75 | | | | | 80 | | |

| tta | ggc | gtt | gcg | cca | agc | gta | tcc | ttg | tac | gcg | gtt | aaa | gta | ctg | aat | 288 |
|---|---|---|---|---|---|---|---|---|---|---|---|---|---|---|---|---|
| Leu | Gly | Val | Ala | Pro | Ser | Val | Ser | Leu | Tyr | Ala | Val | Lys | Val | Leu | Asn | |
| | | | | 85 | | | | | 90 | | | | | 95 | | |

| tca | agc | gga | agc | gga | tca | tac | agc | ggc | att | gta | agc | gga | atc | gag | tgg | 336 |
|---|---|---|---|---|---|---|---|---|---|---|---|---|---|---|---|---|
| Ser | Ser | Gly | Ser | Gly | Ser | Tyr | Ser | Gly | Ile | Val | Ser | Gly | Ile | Glu | Trp | |
| | | | 100 | | | | | 105 | | | | | 110 | | | |

| gcg | aca | aca | aac | ggc | atg | gat | gtt | atc | aat | atg | agc | ctt | ggg | gga | gca | 384 |
|---|---|---|---|---|---|---|---|---|---|---|---|---|---|---|---|---|
| Ala | Thr | Thr | Asn | Gly | Met | Asp | Val | Ile | Asn | Met | Ser | Leu | Gly | Gly | Ala | |
| | | 115 | | | | | 120 | | | | | 125 | | | | |

| tca | ggc | tcg | aca | gcg | atg | aaa | cag | gca | gtc | gac | aat | gca | tat | gca | aga | 432 |
|---|---|---|---|---|---|---|---|---|---|---|---|---|---|---|---|---|
| Ser | Gly | Ser | Thr | Ala | Met | Lys | Gln | Ala | Val | Asp | Asn | Ala | Tyr | Ala | Arg | |
| | 130 | | | | | 135 | | | | | 140 | | | | | |

| ggg | gtc | gtc | gtt | gta | gct | gca | gca | ggg | aac | agc | gga | tct | tca | gga | aac | 480 |
|---|---|---|---|---|---|---|---|---|---|---|---|---|---|---|---|---|
| Gly | Val | Val | Val | Val | Ala | Ala | Ala | Gly | Asn | Ser | Gly | Ser | Ser | Gly | Asn | |
| 145 | | | | 150 | | | | | 155 | | | | | 160 | | |

| acg | aat | aca | att | ggc | tat | cct | gcg | aaa | tac | gat | tct | gtc | atc | gct | gtt | 528 |
|---|---|---|---|---|---|---|---|---|---|---|---|---|---|---|---|---|
| Thr | Asn | Thr | Ile | Gly | Tyr | Pro | Ala | Lys | Tyr | Asp | Ser | Val | Ile | Ala | Val | |
| | | | 165 | | | | | 170 | | | | | 175 | | | |

| ggt | gcg | gta | gac | tct | aac | agc | aac | aga | gct | tca | ttt | tcc | agc | gtc | gga | 576 |
|---|---|---|---|---|---|---|---|---|---|---|---|---|---|---|---|---|
| Gly | Ala | Val | Asp | Ser | Asn | Ser | Asn | Arg | Ala | Ser | Phe | Ser | Ser | Val | Gly | |
| | | | 180 | | | | | 185 | | | | | 190 | | | |

| gca | gag | ctt | gaa | gtc | atg | gct | cct | ggc | gca | ggc | gta | tac | agc | act | tac | 624 |
|---|---|---|---|---|---|---|---|---|---|---|---|---|---|---|---|---|
| Ala | Glu | Leu | Glu | Val | Met | Ala | Pro | Gly | Ala | Gly | Val | Tyr | Ser | Thr | Tyr | |
| | | | | 195 | | | | | 200 | | | | | 205 | | |

| cca | acg | aac | act | tat | gca | aca | tgg | aac | gga | acg | tca | atg | gct | tct | cct | 672 |
|---|---|---|---|---|---|---|---|---|---|---|---|---|---|---|---|---|
| Pro | Thr | Asn | Thr | Tyr | Ala | Thr | Trp | Asn | Gly | Thr | Ser | Met | Ala | Ser | Pro | |
| | 210 | | | | | 215 | | | | | 220 | | | | | |

| cat | gta | gcg | gga | gca | gca | gct | ttg | atc | ttg | tca | aaa | cat | ccg | aac | ctt | 720 |
|---|---|---|---|---|---|---|---|---|---|---|---|---|---|---|---|---|
| His | Val | Ala | Gly | Ala | Ala | Ala | Leu | Ile | Leu | Ser | Lys | His | Pro | Asn | Leu | |
| 225 | | | | 230 | | | | | 235 | | | | | 240 | | |

| tca | gct | tca | caa | gtc | cgc | aac | cgt | ctc | tcc | agc | acg | gcg | act | tat | ttg | 768 |
|---|---|---|---|---|---|---|---|---|---|---|---|---|---|---|---|---|
| Ser | Ala | Ser | Gln | Val | Arg | Asn | Arg | Leu | Ser | Ser | Thr | Ala | Thr | Tyr | Leu | |
| | | | | 245 | | | | | 250 | | | | | 255 | | |

| gga | agc | tcc | ttc | tac | tat | ggg | aaa | ggt | ctg | atc | aat | gtc | gaa | gct | gcc | 816 |
|---|---|---|---|---|---|---|---|---|---|---|---|---|---|---|---|---|
| Gly | Ser | Ser | Phe | Tyr | Tyr | Gly | Lys | Gly | Leu | Ile | Asn | Val | Glu | Ala | Ala | |
| | | | 260 | | | | | 265 | | | | | 270 | | | |

| gct | caa | ta | | | | | | | | | | | | | | 824 |
|---|---|---|---|---|---|---|---|---|---|---|---|---|---|---|---|---|
| Ala | Gln | | | | | | | | | | | | | | | |

<210> SEQ ID NO 14
<211> LENGTH: 274
<212> TYPE: PRT
<213> ORGANISM: Artificial
<220> FEATURE:
<223> OTHER INFORMATION: Synthetic Construct

<400> SEQUENCE: 14

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Ala Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Trp Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln
```

<210> SEQ ID NO 15
<211> LENGTH: 824
<212> TYPE: DNA
<213> ORGANISM: Artificial
<220> FEATURE:
<223> OTHER INFORMATION: Variant T58Q/L89S/L216W of Subtilisin Carlsberg
<220> FEATURE:
<221> NAME/KEY: CDS
<222> LOCATION: (1)..(822)

<400> SEQUENCE: 15

```
gcg caa acc gtt cct tac ggc att cct ctc att aaa gcg gac aaa gtg    48
Ala Gln Thr Val Pro Tyr Gly Ile Pro Leu Ile Lys Ala Asp Lys Val
1               5                   10                  15
```

|     |     |     |     |     |     |     |     |     |     |     |     |     |     |     |     |     |
|---|---|---|---|---|---|---|---|---|---|---|---|---|---|---|---|---|
| cag | gct | caa | ggc | ttt | aag | gga | gcg | aat | gta | aaa | gta | gcc | gtc | ctg | gat | 96 |
| Gln | Ala | Gln | Gly | Phe | Lys | Gly | Ala | Asn | Val | Lys | Val | Ala | Val | Leu | Asp | |
| | | | 20 | | | | | 25 | | | | | 30 | | | |
| aca | gga | atc | caa | gct | tct | cat | ccg | gac | ttg | aac | gta | gtc | ggc | gga | gca | 144 |
| Thr | Gly | Ile | Gln | Ala | Ser | His | Pro | Asp | Leu | Asn | Val | Val | Gly | Gly | Ala | |
| | | | 35 | | | | | 40 | | | | | 45 | | | |
| agc | ttt | gtg | gct | ggc | gaa | gct | tat | aac | cag | gac | ggc | aac | gga | cac | ggc | 192 |
| Ser | Phe | Val | Ala | Gly | Glu | Ala | Tyr | Asn | Gln | Asp | Gly | Asn | Gly | His | Gly | |
| | 50 | | | | | 55 | | | | | 60 | | | | | |
| aca | cat | gtt | gcc | ggt | aca | gta | gct | gcg | ctt | gac | aat | aca | acg | ggt | gtt | 240 |
| Thr | His | Val | Ala | Gly | Thr | Val | Ala | Ala | Leu | Asp | Asn | Thr | Thr | Gly | Val | |
| 65 | | | | | 70 | | | | | 75 | | | | | 80 | |
| tta | ggc | gtt | gcg | cca | agc | gta | tcc | tcg | tac | gcg | gtt | aaa | gta | ctg | aat | 288 |
| Leu | Gly | Val | Ala | Pro | Ser | Val | Ser | Ser | Tyr | Ala | Val | Lys | Val | Leu | Asn | |
| | | | | 85 | | | | | 90 | | | | | 95 | | |
| tca | agc | gga | agc | gga | tca | tac | agc | ggc | att | gta | agc | gga | atc | gag | tgg | 336 |
| Ser | Ser | Gly | Ser | Gly | Ser | Tyr | Ser | Gly | Ile | Val | Ser | Gly | Ile | Glu | Trp | |
| | | | | 100 | | | | | 105 | | | | | 110 | | |
| gcg | aca | aca | aac | ggc | atg | gat | gtt | atc | aat | atg | agc | ctt | ggg | gga | gca | 384 |
| Ala | Thr | Thr | Asn | Gly | Met | Asp | Val | Ile | Asn | Met | Ser | Leu | Gly | Gly | Ala | |
| | | | 115 | | | | | 120 | | | | | 125 | | | |
| tca | ggc | tcg | aca | gcg | atg | aaa | cag | gca | gtc | gac | aat | gca | tat | gca | aga | 432 |
| Ser | Gly | Ser | Thr | Ala | Met | Lys | Gln | Ala | Val | Asp | Asn | Ala | Tyr | Ala | Arg | |
| | 130 | | | | | 135 | | | | | 140 | | | | | |
| ggg | gtc | gtc | gtt | gta | gct | gca | gca | ggg | aac | agc | gga | tct | tca | gga | aac | 480 |
| Gly | Val | Val | Val | Val | Ala | Ala | Ala | Gly | Asn | Ser | Gly | Ser | Ser | Gly | Asn | |
| 145 | | | | | 150 | | | | | 155 | | | | | 160 | |
| acg | aat | aca | att | ggc | tat | cct | gcg | aaa | tac | gat | tct | gtc | atc | gct | gtt | 528 |
| Thr | Asn | Thr | Ile | Gly | Tyr | Pro | Ala | Lys | Tyr | Asp | Ser | Val | Ile | Ala | Val | |
| | | | | 165 | | | | | 170 | | | | | 175 | | |
| ggt | gcg | gta | gac | tct | aac | agc | aac | aga | gct | tca | ttt | tcc | agc | gtc | gga | 576 |
| Gly | Ala | Val | Asp | Ser | Asn | Ser | Asn | Arg | Ala | Ser | Phe | Ser | Ser | Val | Gly | |
| | | | 180 | | | | | 185 | | | | | 190 | | | |
| gca | gag | ctt | gaa | gtc | atg | gct | cct | ggc | gca | ggc | gta | tac | agc | act | tac | 624 |
| Ala | Glu | Leu | Glu | Val | Met | Ala | Pro | Gly | Ala | Gly | Val | Tyr | Ser | Thr | Tyr | |
| | | 195 | | | | | 200 | | | | | 205 | | | | |
| cca | acg | aac | act | tat | gca | aca | tgg | aac | gga | acg | tca | atg | gct | tct | cct | 672 |
| Pro | Thr | Asn | Thr | Tyr | Ala | Thr | Trp | Asn | Gly | Thr | Ser | Met | Ala | Ser | Pro | |
| | 210 | | | | | 215 | | | | | 220 | | | | | |
| cat | gta | gcg | gga | gca | gca | gct | ttg | atc | ttg | tca | aaa | cat | ccg | aac | ctt | 720 |
| His | Val | Ala | Gly | Ala | Ala | Ala | Leu | Ile | Leu | Ser | Lys | His | Pro | Asn | Leu | |
| 225 | | | | | 230 | | | | | 235 | | | | | 240 | |
| tca | gct | tca | caa | gtc | cgc | aac | cgt | ctc | tcc | agc | acg | gcg | act | tat | ttg | 768 |
| Ser | Ala | Ser | Gln | Val | Arg | Asn | Arg | Leu | Ser | Ser | Thr | Ala | Thr | Tyr | Leu | |
| | | | | 245 | | | | | 250 | | | | | 255 | | |
| gga | agc | tcc | ttc | tac | tat | ggg | aaa | ggt | ctg | atc | aat | gtc | gaa | gct | gcc | 816 |
| Gly | Ser | Ser | Phe | Tyr | Tyr | Gly | Lys | Gly | Leu | Ile | Asn | Val | Glu | Ala | Ala | |
| | | | 260 | | | | | 265 | | | | | 270 | | | |
| gct | caa | ta | | | | | | | | | | | | | | 824 |
| Ala | Gln | | | | | | | | | | | | | | | |

<210> SEQ ID NO 16
<211> LENGTH: 274
<212> TYPE: PRT
<213> ORGANISM: Artificial
<220> FEATURE:
<223> OTHER INFORMATION: Synthetic Construct

<400> SEQUENCE: 16

Ala Gln Thr Val Pro Tyr Gly Ile Pro Leu Ile Lys Ala Asp Lys Val
1               5                   10                  15

```
Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Gln Asp Gly Asn Gly His Gly
    50                  55                  60

Thr His Val Ala Gly Thr Val Ala Leu Asp Asn Thr Thr Gly Val
65                  70                  75                  80

Leu Gly Val Ala Pro Ser Val Ser Ser Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Trp Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 17
<211> LENGTH: 824
<212> TYPE: DNA
<213> ORGANISM: Artificial
<220> FEATURE:
<223> OTHER INFORMATION: Variant L89S/L216W of Subtilisin Carlsberg
<220> FEATURE:
<221> NAME/KEY: CDS
<222> LOCATION: (1)..(822)

<400> SEQUENCE: 17 gcg caa acc gtt cct tac ggc att cct ctc att aaa gcg gac aaa gtg      48
Ala Gln Thr Val Pro Tyr Gly Ile Pro Leu Ile Lys Ala Asp Lys Val
1               5                   10                  15 cag gct caa ggc ttt aag gga gcg aat gta aaa gta gcc gtc ctg gat      96
Gln Ala Gln Gly Phe Lys Gly Ala Asn Val Lys Val Ala Val Leu Asp
            20                  25                  30 aca gga atc caa gct tct cat ccg gac ttg aac gta gtc ggc gga gca     144
Thr Gly Ile Gln Ala Ser His Pro Asp Leu Asn Val Val Gly Gly Ala
        35                  40                  45 agc ttt gtg gct ggc gaa gct tat aac acc gac ggc aac gga cac ggc     192
Ser Phe Val Ala Gly Glu Ala Tyr Asn Thr Asp Gly Asn Gly His Gly
    50                  55                  60
```

```
aca cat gtt gcc ggt aca gta gct gcg ctt gac aat aca acg ggt gtt      240
Thr His Val Ala Gly Thr Val Ala Ala Leu Asp Asn Thr Thr Gly Val
 65              70                  75                  80 tta ggc gtt gcg cca agc gta tcc tcg tac gcg gtt aaa gta ctg aat      288
Leu Gly Val Ala Pro Ser Val Ser Ser Tyr Ala Val Lys Val Leu Asn
                 85                  90                  95 tca agc gga agc gga tca tac agc ggc att gta agc gga atc gag tgg      336
Ser Ser Gly Ser Gly Ser Tyr Ser Gly Ile Val Ser Gly Ile Glu Trp
            100                 105                 110 gcg aca aca aac ggc atg gat gtt atc aat atg agc ctt ggg gga gca      384
Ala Thr Thr Asn Gly Met Asp Val Ile Asn Met Ser Leu Gly Gly Ala
        115                 120                 125 tca ggc tcg aca gcg atg aaa cag gca gtc gac aat gca tat gca aga      432
Ser Gly Ser Thr Ala Met Lys Gln Ala Val Asp Asn Ala Tyr Ala Arg
130                 135                 140 ggg gtc gtc gtt gta gct gca gca ggg aac agc gga tct tca gga aac      480
Gly Val Val Val Ala Ala Gly Asn Ser Gly Ser Ser Gly Asn
145                 150                 155                 160 acg aat aca att ggc tat cct gcg aaa tac gat tct gtc atc gct gtt      528
Thr Asn Thr Ile Gly Tyr Pro Ala Lys Tyr Asp Ser Val Ile Ala Val
                165                 170                 175 ggt gcg gta gac tct aac agc aac aga gct tca ttt tcc agc gtc gga      576
Gly Ala Val Asp Ser Asn Ser Asn Arg Ala Ser Phe Ser Ser Val Gly
            180                 185                 190 gca gag ctt gaa gtc atg gct cct ggc gca ggc gta tac agc act tac      624
Ala Glu Leu Glu Val Met Ala Pro Gly Ala Gly Val Tyr Ser Thr Tyr
        195                 200                 205 cca acg aac act tat gca aca tgg aac gga acg tca atg gct tct cct      672
Pro Thr Asn Thr Tyr Ala Thr Trp Asn Gly Thr Ser Met Ala Ser Pro
210                 215                 220 cat gta gcg gga gca gca gct ttg atc ttg tca aaa cat ccg aac ctt      720
His Val Ala Gly Ala Ala Ala Leu Ile Leu Ser Lys His Pro Asn Leu
225                 230                 235                 240 tca gct tca caa gtc cgc aac cgt ctc tcc agc acg gcg act tat ttg      768
Ser Ala Ser Gln Val Arg Asn Arg Leu Ser Ser Thr Ala Thr Tyr Leu
                245                 250                 255 gga agc tcc ttc tac tat ggg aaa ggt ctg atc aat gtc gaa gct gcc      816
Gly Ser Ser Phe Tyr Tyr Gly Lys Gly Leu Ile Asn Val Glu Ala Ala
            260                 265                 270 gct caa ta                                                            824
Ala Gln <210> SEQ ID NO 18
<211> LENGTH: 274
<212> TYPE: PRT
<213> ORGANISM: Artificial
<220> FEATURE:
<223> OTHER INFORMATION: Synthetic Construct

<400> SEQUENCE: 18

Ala Gln Thr Val Pro Tyr Gly Ile Pro Leu Ile Lys Ala Asp Lys Val
 1               5                  10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
        50                  55                  60

Thr His Val Ala Gly Thr Val Ala Ala Leu Asp Asn Thr Thr Gly Val
```

```
                 65                  70                  75                  80
Leu Gly Val Ala Pro Ser Val Ser Ser Tyr Ala Val Lys Val Leu Asn
                 85                  90                  95
Ser Ser Gly Ser Gly Ser Tyr Ser Gly Ile Val Ser Gly Ile Glu Trp
                100                 105                 110
Ala Thr Thr Asn Gly Met Asp Val Ile Asn Met Ser Leu Gly Gly Ala
                115                 120                 125
Ser Gly Ser Thr Ala Met Lys Gln Ala Val Asp Asn Ala Tyr Ala Arg
        130                 135                 140
Gly Val Val Val Ala Ala Ala Gly Asn Ser Gly Ser Ser Gly Asn
145                 150                 155                 160
Thr Asn Thr Ile Gly Tyr Pro Ala Lys Tyr Asp Ser Val Ile Ala Val
                165                 170                 175
Gly Ala Val Asp Ser Asn Ser Asn Arg Ala Ser Phe Ser Ser Val Gly
                180                 185                 190
Ala Glu Leu Glu Val Met Ala Pro Gly Ala Gly Val Tyr Ser Thr Tyr
                195                 200                 205
Pro Thr Asn Thr Tyr Ala Thr Trp Asn Gly Thr Ser Met Ala Ser Pro
        210                 215                 220
His Val Ala Gly Ala Ala Ala Leu Ile Leu Ser Lys His Pro Asn Leu
225                 230                 235                 240
Ser Ala Ser Gln Val Arg Asn Arg Leu Ser Ser Thr Ala Thr Tyr Leu
                245                 250                 255
Gly Ser Ser Phe Tyr Tyr Gly Lys Gly Leu Ile Asn Val Glu Ala Ala
                260                 265                 270
Ala Gln

<210> SEQ ID NO 19
<211> LENGTH: 21
<212> TYPE: DNA
<213> ORGANISM: Artificial
<220> FEATURE:
<223> OTHER INFORMATION: Primer PSC-s

<400> SEQUENCE: 19
cccgggacct ctttccctgc c                                           21

<210> SEQ ID NO 20
<211> LENGTH: 21
<212> TYPE: DNA
<213> ORGANISM: Artificial
<220> FEATURE:
<223> OTHER INFORMATION: Primer PSC-as

<400> SEQUENCE: 20
ctcgagtatg ttattgagcg g                                           21

<210> SEQ ID NO 21
<211> LENGTH: 27
<212> TYPE: DNA
<213> ORGANISM: Artificial
<220> FEATURE:
<223> OTHER INFORMATION: Primer P300-s

<400> SEQUENCE: 21
gcgcttaagg aagtcaaaaa tgatccg                                     27

<210> SEQ ID NO 22
<211> LENGTH: 1140
```

```
<212> TYPE: DNA
<213> ORGANISM: Bacillus licheniformis
<220> FEATURE:
<221> NAME/KEY: CDS
<222> LOCATION: (1)..(1137)
<220> FEATURE:
<221> NAME/KEY: mat_peptide
<222> LOCATION: (316)..(1140)

<400> SEQUENCE: 22 atg atg agg aaa aag agt ttt tgg ctt ggg atg ctg acg gcc ttc atg         48
Met Met Arg Lys Lys Ser Phe Trp Leu Gly Met Leu Thr Ala Phe Met
-105            -100                -95                 -90 ctc gtg ttc acg atg gca ttc agc gat tcc gct tct gct gct caa ccg         96
Leu Val Phe Thr Met Ala Phe Ser Asp Ser Ala Ser Ala Ala Gln Pro
        -85                 -80                 -75 gcg aaa aat gtt gaa aag gat tat att gtc gga ttt aag tca gga gtg        144
Ala Lys Asn Val Glu Lys Asp Tyr Ile Val Gly Phe Lys Ser Gly Val
            -70                 -65                 -60 aaa acc gca tct gtc aaa aag gac atc atc aaa gag agc ggc gga aaa        192
Lys Thr Ala Ser Val Lys Lys Asp Ile Ile Lys Glu Ser Gly Gly Lys
        -55                 -50                 -45 gtg gac aag cag ttt aga atc atc aac gcg gca aaa gcg aag cta gac        240
Val Asp Lys Gln Phe Arg Ile Ile Asn Ala Ala Lys Ala Lys Leu Asp
-40                 -35                 -30 aaa gaa gcg ctt aag gaa gtc aaa aat gat ccg gat gtc gct tat gtg        288
Lys Glu Ala Leu Lys Glu Val Lys Asn Asp Pro Asp Val Ala Tyr Val
-25                 -20                 -15                 -10 gaa gag gat cat gtg gcc cat gcg cta gcg caa acc gtt cct tac ggc        336
Glu Glu Asp His Val Ala His Ala Leu Ala Gln Thr Val Pro Tyr Gly
            -5                  -1  1               5 att cct ctc att aaa gcg gac aaa gtg cag gct caa ggc ttt aag gga        384
Ile Pro Leu Ile Lys Ala Asp Lys Val Gln Ala Gln Gly Phe Lys Gly
        10                  15                  20 gcg aat gta aaa gta gcc gtc ctg gat aca gga atc caa gct tct cat        432
Ala Asn Val Lys Val Ala Val Leu Asp Thr Gly Ile Gln Ala Ser His
    25                  30                  35 ccg gac ttg aac gta gtc ggc gga gca agc ttt gtg gct ggc gaa gct        480
Pro Asp Leu Asn Val Val Gly Gly Ala Ser Phe Val Ala Gly Glu Ala
40                  45                  50                  55 tat aac acc gac ggc aac gga cac ggc aca cat gtt gcc ggt aca gta        528
Tyr Asn Thr Asp Gly Asn Gly His Gly Thr His Val Ala Gly Thr Val
                60                  65                  70 gct gcg ctt gac aat aca acg ggt gta tta ggc gtt gcg cca agc gta        576
Ala Ala Leu Asp Asn Thr Thr Gly Val Leu Gly Val Ala Pro Ser Val
            75                  80                  85 tcc ttg tac gcg gtt aaa gta ctg aat tca agc gga agc gga tca tac        624
Ser Leu Tyr Ala Val Lys Val Leu Asn Ser Ser Gly Ser Gly Ser Tyr
        90                  95                  100 agc ggc att gta agc gga atc gag tgg gcg aca aca aac ggc atg gat        672
Ser Gly Ile Val Ser Gly Ile Glu Trp Ala Thr Thr Asn Gly Met Asp
    105                 110                 115 gtt atc aat atg agc ctt ggg gga gca tca ggc tcg aca gcg atg aaa        720
Val Ile Asn Met Ser Leu Gly Gly Ala Ser Gly Ser Thr Ala Met Lys
120                 125                 130                 135 cag gca gtc gac aat gca tat gca aga ggg gtt gtc gtt gta gct gca        768
Gln Ala Val Asp Asn Ala Tyr Ala Arg Gly Val Val Val Val Ala Ala
                140                 145                 150 gca ggg aac agc gga tct tca gga aac acg aat aca ata ggc tat cct        816
Ala Gly Asn Ser Gly Ser Ser Gly Asn Thr Asn Thr Ile Gly Tyr Pro
            155                 160                 165
```

```
gcg aaa tac gat tct gtc atc gct gtt ggt gcg gta gac tct aac agc      864
Ala Lys Tyr Asp Ser Val Ile Ala Val Gly Ala Val Asp Ser Asn Ser
        170                 175                 180 aac aga gct tca ttt tcc agc gtc gga gca gag ctt gaa gtc atg gct      912
Asn Arg Ala Ser Phe Ser Ser Val Gly Ala Glu Leu Glu Val Met Ala
185                 190                 195 cct ggc gca ggc gta tac agc act tac cca acg aac act tat gca aca      960
Pro Gly Ala Gly Val Tyr Ser Thr Tyr Pro Thr Asn Thr Tyr Ala Thr
200                 205                 210                 215 ttg aac gga acg tca atg gct tct cct cat gta gcg gga gca gca gct     1008
Leu Asn Gly Thr Ser Met Ala Ser Pro His Val Ala Gly Ala Ala Ala
                220                 225                 230 ttg atc ttg tca aaa cat ccg aac ctt tca gct tca caa gtc cgc aac     1056
Leu Ile Leu Ser Lys His Pro Asn Leu Ser Ala Ser Gln Val Arg Asn
            235                 240                 245 cgt ctc tcc agc acg gcg act tat ttg gga agc tcc ttc tac tat ggg     1104
Arg Leu Ser Ser Thr Ala Thr Tyr Leu Gly Ser Ser Phe Tyr Tyr Gly
        250                 255                 260 aaa ggt ctg atc aat gtc gaa gct gcc gct caa tga                     1140
Lys Gly Leu Ile Asn Val Glu Ala Ala Ala Gln
265                 270
```

<210> SEQ ID NO 23
<211> LENGTH: 379
<212> TYPE: PRT
<213> ORGANISM: Bacillus licheniformis

<400> SEQUENCE: 23

```
Met  Met Arg Lys Lys Ser  Phe Trp Leu Gly Met  Leu Thr Ala Phe Met
-105                -100                -95                 -90

Leu Val Phe Thr Met Ala Phe Ser Asp Ser Ala Ser Ala Ala Gln Pro
                -85                 -80                 -75

Ala Lys Asn Val Glu Lys Asp Tyr Ile Val Gly Phe Lys Ser Gly Val
                -70                 -65                 -60

Lys Thr Ala Ser Val Lys Lys Asp Ile Ile Lys Glu Ser Gly Gly Lys
        -55                 -50                 -45

Val Asp Lys Gln Phe Arg Ile Ile Asn Ala Ala Lys Ala Lys Leu Asp
    -40                 -35                 -30

Lys Glu Ala Leu Lys Glu Val Lys Asn Asp Pro Asp Val Ala Tyr Val
-25                 -20                 -15                 -10

Glu Glu Asp His Val Ala His Ala Leu Ala Gln Thr Val Pro Tyr Gly
                -5                  -1  1               5

Ile Pro Leu Ile Lys Ala Asp Lys Val Gln Ala Gln Gly Phe Lys Gly
            10                  15                  20

Ala Asn Val Lys Val Ala Val Leu Asp Thr Gly Ile Gln Ala Ser His
25                  30                  35

Pro Asp Leu Asn Val Val Gly Gly Ala Ser Phe Val Ala Gly Glu Ala
40                  45                  50                  55

Tyr Asn Thr Asp Gly Asn Gly His Gly Thr His Val Ala Gly Thr Val
                60                  65                  70

Ala Ala Leu Asp Asn Thr Thr Gly Val Leu Gly Val Ala Pro Ser Val
            75                  80                  85

Ser Leu Tyr Ala Val Lys Val Leu Asn Ser Ser Gly Ser Gly Ser Tyr
        90                  95                  100

Ser Gly Ile Val Ser Gly Ile Glu Trp Ala Thr Thr Asn Gly Met Asp
    105                 110                 115

Val Ile Asn Met Ser Leu Gly Gly Ala Ser Gly Ser Thr Ala Met Lys
```

```
                        -continued
120                 125             130                 135
Gln Ala Val Asp Asn Ala Tyr Ala Arg Gly Val Val Val Ala Ala
                140             145                 150

Ala Gly Asn Ser Gly Ser Ser Gly Asn Thr Asn Thr Ile Gly Tyr Pro
            155                 160                 165

Ala Lys Tyr Asp Ser Val Ile Ala Val Gly Ala Val Asp Ser Asn Ser
        170                 175                 180

Asn Arg Ala Ser Phe Ser Ser Val Gly Ala Glu Leu Glu Val Met Ala
        185                 190                 195

Pro Gly Ala Gly Val Tyr Ser Thr Tyr Pro Thr Asn Thr Tyr Ala Thr
200                 205                 210                 215

Leu Asn Gly Thr Ser Met Ala Ser Pro His Val Ala Gly Ala Ala Ala
            220                 225                 230

Leu Ile Leu Ser Lys His Pro Asn Leu Ser Ala Ser Gln Val Arg Asn
            235                 240                 245

Arg Leu Ser Ser Thr Ala Thr Tyr Leu Gly Ser Ser Phe Tyr Tyr Gly
        250                 255                 260

Lys Gly Leu Ile Asn Val Glu Ala Ala Ala Gln
    265                 270

<210> SEQ ID NO 24
<211> LENGTH: 4
<212> TYPE: PRT
<213> ORGANISM: Artificial
<220> FEATURE:
<223> OTHER INFORMATION: Synthetic Construct

<400> SEQUENCE: 24

Ala Ala Pro Phe
1
```

SUBTILISIN VARIANTS WITH IMPROVED PERHYDROLASE ACTIVITY

CROSS REFERENCE TO RELATED APPLICATIONS

This application is a continuation of PCT/EP2003/014127, filed Dec. 12, 2003, which claims priority to DE 102 60 903.9, filed Dec. 20, 2002, the disclosures of which are incorporated herein in their entireties.

DETAILED DESCRIPTION OF ILLUSTRATIVE EMBODIMENTS

The present invention relates to novel perhydrolases, which can be derived from the protease Carlsberg by amino acid exchange in certain positions. It further relates to procedures for producing these novel perhydrolases, substances which contain these novel perhydrolases, especially cosmetics and beauty products, therapeutics, washing and cleaning agents, and corresponding applications of these novel perhydrolases.

Usually inorganic, highly alkaline hydrogen peroxide suppliers such as percarbonate and perborate combined with bleach boosters (TAED or NOBS) are used to produce conventional chemical laundry bleaches. However, this standard bleaching system is only fully effective at temperatures of 60° C. and above. There is no optimum bleaching system available for the low temperature range. In addition, localized "spotting" frequently occurs in colored textiles. The bleach component hydrogen peroxide is formed from the spontaneous decomposition of the salt, which rapidly results in high concentrations of short duration. Thus, it is generally not possible to produce a gentle, controlled release bleach at milder pH in this way.

Likewise, there is no optimum bleaching system available for use in weakly alkaline detergent matrices such as liquid formulations.

In conventional hair dyes, a bleach is applied to balance out the gray tones prior to coloring with hydrogen peroxide and ammonia. The short-term high concentrations of hydrogen peroxide combined with the alkaline pH lead to marked hair damage. A pre-treatment without the unpleasant odor of ammonia, but which continuously releases hydrogen peroxide at a neutral or weakly alkaline pH is not currently available.

With the help of hydrogen peroxide, proteases can release percarboxylic acid as a bleaching agent from esters of percarboxylic acid:

Up until now this secondary protease reaction has been inadequate for a commercial use of proteases as bleaching enzymes in washing and cleaning agents.

Proteases, in particular the subtilisins, have hitherto been used as active substances in washing and cleaning agents due to their proteolytic activity. This also includes the protease subtilisin Carlsberg, which is presented in the publications of E. L. Smith et al. (1968) in *J. Biol. Chem.*, Volume 243, pp. 2184-2191, and Jacobs et al. (1985) in *Nucl. Acids Res.*, Volume 13, pp. 8913-8926. This is produced naturally from *Bacillus licheniformis* and was and is available under the trade name Maxatase® from Genencor International Inc., Rochester, N.Y., USA, and under the trade name Alcalase® from Novozymes A/S, Bagsvaerd, Denmark.

Variants resulting from point mutations of this enzyme are also described, aimed purely at optimizing the proteolytic activity, which is relevant to their use in washing and cleaning agents. Thus, for example, Carlsberg variants are known from the application WO 96/28566 A2, which have reduced bonding to the substrate with a simultaneous increased hydrolysis rate.

Surprisingly, as a result of a random mutagenesis, it has now been discovered that the modification of the special protease subtilisin Carlsberg (described in SEQ ID NO. 23 of the present application) by point mutagenesis can generate perhydrolases that can be used in bleach systems whilst generally avoiding the disadvantages associated with the relevant prior art. This is of particular relevance to the technical fields outlined in the introduction, namely washing and cleaning agents, cosmetics and beauty products, especially hair care products.

Thus, the subject of the present invention is a perhydrolase, whose amino acid sequence corresponds to that indicated in SEQ ID NO. 23, yet with one or more amino acid exchanges in positions 11, 15, 21, 38, 50, 54, 58, 77, 83, 89, 93, 96, 107, 117, 120, 134, 135, 136, 140, 147, 150, 154, 155, 160, 161, 171, 179, 180, 181, 194, 205, 208, 213, 216, 217, 238, 239, 251, 253, 257, 261.

The starting point of the present invention is therefore the protease subtilisin Carlsberg described in SEQ ID NO. 23 of the present application. On the basis of these indications, this enzyme can be produced using established molecular biological and biotechnological methods. Following the description in example 1 of the present application, it is possible either to amplify the relevant nucleic acid region from the chromosomal DNA of a *Bacillus licheniformis* strain (e.g. *B. licheniformis* DSM 461, available from the German Collection of Microorganisms and Cell Cultures, Mascheroder Weg 1b, D-38124 Braunschweig), via PCR or via the two oligonucleotides PSC-s and PSC-as (SEQ ID NO. 19 or 20) as primers.

Although a random mutagenesis is described in example 2 to produce inventive variants, targeted point mutations can now be conducted by using the present invention at the positions described here in the sequences disclosed in the sequence protocol.

In this manner, the perhydrolytic properties of the subtilisin Carlsberg on the substrates required for perhydrolysis—esters of percarboxylic acid and hydrogen peroxide—are improved. Therefore, the ability of the enzyme to perhydrolyze esters of percarboxylic acid using hydrogen peroxide to peracid is increased and so a commercially viable bleach enzyme is obtained.

The actual main reaction, which has hitherto been at the forefront of the use of this enzyme, is not necessarily diminished by these mutations. This invention, however, focuses on the improved perhydrolytic properties. Example 4 in particular demonstrates that for some variants, the protease activity in many cases is not lost. In the context of the present invention, the particularly preferred variants are those, which with increased perhydrolysis activity still possess a high proteolysis activity, since the relevant enzyme in the corresponding agent then performs a dual function.

In example 4 measurements under the conditions described there reveal a proteolytic activity of 0.8 U (AAPF) per μg for the unaltered subtilisin Carlsberg (control). According to this measurement, this wild-type enzyme has a perhydrolytic secondary activity of 0.33 ppm AO per μg enzyme.

The perhydrolases tested in example 4, i.e. each of the indicated special variants of the subtilisin Carsberg, show reduced protease activity. On the other hand, the amino acid substitutions have led to an increase in the perhydrolytic secondary activity, giving values of at least 0.57 and in the best case 0.98 ppm AO per μg enzyme for this reaction batch. Compared with 0.33 ppm AO per μg for the wild-type enzyme, this represents at least a 1.7 fold increase.

Thus, in the context of the present application "perhydrolase" means an enzyme, which demonstrates a perhydrolytic activity increased by a factor of at least 1.7 compared with the unaltered subtilisin Carlsberg. Advantageously, this is determined using the method described in Example 3.

The amino acid exchanges at the said positions can be conducted using molecular biological methods known per se, preferably at the level of the associated nucleotide sequence (as indicated in SEQ ID NO. 22 for example) in the form of point mutations. Commercially available kits for site directed mutaganesis via mismatch primers are suitable for this, for example the QuickChange® Kit from Stratagene, La Jolla, USA. The numbering of the positions refers to the mature Carlsberg protein, where position +1 corresponds to the codon GCG in positions 316-318 in accordance with SEQ ID NO. 22. This is position 106 in the numbering of the unprocessed protein described in SEQ ID NO. 23. Accordingly, genes, which already have a mutation, especially one according to the invention, can also be provided with one or more additional mutations according to the invention, affording a plurality of variants according to the invention.

In the context of the present application "protein" means a polymer with an essentially linear structure, composed of natural amino acids, and which generally assumes a three-dimensional structure to perform its function. In the present application, the 19 naturally occurring proteinogenic L-amino acids are designated by the standard international 1 and 3 letter codes.

In the context of the present application "enzyme" means a protein, which performs a particular biocatalytic function.

Numerous proteins are produced as inactive precursors, so-called "preproteins" or "preproproteins", i.e. combined with a signal peptide and/or propeptide. A signal peptide means the N-terminal part of the protein, whose function is to ensure the transfer of the produced protein from the producing cell into the periplasma or the surrounding medium. The signal peptide is then cleaved off the remaining proprotein under natural conditions by a signal peptidase. The propeptide ensures the correct folding of the protein and is autocatalytically cleaved from the mature, catalytically active protein. For technical applications, mature peptides, i.e. the enzymes that are processed after manufacturing, are preferred to the preproteins because of their enzymatic activity.

In the context of the present application "nucleic acids" mean naturally occurring molecules composed of nucleotides, which transmit information and which code for the linear amino acid sequence in proteins or enzymes. They may be present in a single strand, a single strand complementary to this single strand, or a double strand. For molecular biological procedures the nucleic acid DNA is preferred as the natural, more durable information carrier. In contrast, to implement the invention in natural conditions, such as in an expressing cell for example, an RNA is produced, which is why RNA molecules essential to the invention also represent embodiments of the present invention.

In the case of DNA, the sequences of both complementary strings in each of the three possible open reading frames must be taken into account. It must also be considered that different codon triplets can code the same amino acids, thus a specific amino acid sequence can be derived from several different nucleotide sequences, possibly with low identity (degeneration of the genetic code). In addition, different organisms use these codons in different ways. For this reason both amino acid sequences and nucleotide sequences must be included within the scope of the patent and indicated nucleotide sequences are to be regarded in each case simply as exemplary coding for a specific amino acid.

In the context of the present application the information unit corresponding to one protein is also referred to as a "gene".

The present invention comprises the production of "recombinant proteins". According to the invention this includes all genetic and microbiological procedures relating to the insertion of genes for the relevant proteins in a suitable host organism and their subsequent transcription and translation. Suitably, the insertion of the relevant gene is carried out via vectors, expression vectors in particular, or alternatively via those that enable the relevant gene in the host organism to be inserted into a pre-existing genetic element such as a chromosome or other vector. According to the invention, the functional unit consisting of the gene, promoter and possibly additional genetic elements is referred to as an expression cassette. However it does not necessarily also have to be a physical unit.

Using methods which are generally known nowadays, such as chemical synthesis or polymerase chain reaction (PCR) combined with standard methods of molecular biology and/or protein chemistry, it is possible for a skilled person to produce the corresponding nucleic acids right through to complete genes from known DNA and/or amino acid sequences. The methods are described in full in the prior art.

Changes to the nucleotide sequence, such as those caused by known molecular biological methods, are described as "mutations". Depending on the nature of the change, these are called deletion, insertion or substitution mutations. Where different genes or parts of genes have been fused together or recombined, they are called gene mutations. The associated organisms are referred to as "mutants". Proteins derived from mutated nucleic acids are referred to as "variants". Thus deletion, insertion or substitution mutations or fusions lead to deletion-, insertion- or substitution-mutated genes or fusion genes and, at protein level, to corresponding deletion, insertion or substitution variants or fusion proteins.

The following convention is used to describe "point mutations" relating to an exact amino acid position: first the naturally occurring amino acid is described using the standard international one letter code, then comes the associated sequence position and finally the inserted amino acid. Therefore L89S means that in position 89 the original amino acid leucin has been replaced with serin. Several exchanges within the same polypeptide chain are separated from one another by oblique slashes.

"Fragments" refer to all proteins or peptides, which are smaller than natural proteins, or those, which correspond to fully translated genes and which can for example also be obtained synthetically. They can be assigned to the relevant whole proteins on the basis of their amino acid sequences. They can, for example, adopt the same structures or perform enzymatic activities or partial activities such as the complexation of a substrate. Fragments and "deletion variants" of starting proteins are essentially the same; whereas fragments tend to be smaller, only short sections and therefore only individual partial functions are missing from the deletion mutants.

At nucleic acid level the "partial sequences" correspond to the fragments.

In the context of the present application, "chimeric" or "hybrid proteins" refer to those proteins, which are encoded from nucleic acid chains originating naturally from different organisms or from different chromosomal positions in the same organism. This procedure is also known as "recombinant mutagenesis", the aim of which is to cause or to modify a specific enzymatic function with the aid of the fused protein part, for example. Thus in the context of the present invention it is irrelevant whether such a chimeric protein consists of a single polypeptide chain or several subunits, on which different functions can be distributed.

Proteins obtained by "insertion mutation" are those variants, which are obtained by inserting a nucleic acid or protein fragment into the starting sequences using methods known per se. On account of their fundamental similarity they correspond to the chimeric proteins. They differ from these merely in terms of the ratio of the size of the unaltered protein part to the size of the whole protein. In such proteins obtained through insertion mutation the proportion of foreign protein is lower than in chimeric proteins.

"Inversions mutagenesis", i.e. a partial inversion of the sequence, can be regarded as a special form of either deletion or inversion. The same applies to regrouping of different molecular parts, which differs from the original amino acid sequence. It can be regarded as a deletion variant, an insertion variant or also as a shuffling variant of the original protein.

In the context of the present application "derivatives" means proteins whose pure amino acid chain has been chemically modified. Such derivatizations can occur, for example, biologically in connection with the protein biosynthesis by the host organism. This can be achieved using molecular biological methods. Chemical methods can also be used, for example, the chemical transformation of a side chain of an amino acid or by covalent bonding of another compound to the protein. This compound may also consist of other proteins, for example, which are bonded to the proteins according to the invention with bifunctional chemical bonds. These kinds of modifications can, for example, influence the substrate specificity or the bond strength to the substrate, or temporarily block the enzymatic activity, if the bonded substance is an inhibitor. This can make sense for the storage period. Derivatization is also understood to mean covalent bonding to a macromolecular carrier.

Proteins can also be combined to form "groups of immunologically related proteins" by reacting with an antiserum or a specific antibody. Those belonging to a group are characterized by having the same antigenic determinant, recognized by one antibody.

In the context of the present invention, all enzymes, proteins, fragments and derivatives, unless they need to be explicitly referred to as such, will be combined under the generic term "proteins".

In the context of the present invention "vectors" are elements consisting of nucleic acids, which comprise a relevant gene as the characteristic nucleic acid region. They enable this to become established as a stable genetic element in a species or a cell line over several generations or cell divisions. Vectors, especially when used in bacteria, are special plasmids, i.e. circular genetic elements. In genetic engineering a distinction is made between vectors responsible for storage and genetic work, which are called "cloning vectors", and those responsible for establishing the gene in question in the host cell, i.e. enabling the expression of the relevant protein. These vectors are called "expression vectors". There are also other vectors, which can be used for both purposes.

The enzymatic activity of the enzyme under consideration can be deduced from the amino acid or nucleotide sequence by comparison with known enzymes, which are deposited in generally accessible data banks. This activity can be qualitatively or quantitatively modified by other regions of the protein, which are not involved with the actual reaction. This could affect the enzyme stability, the activity, the reaction conditions or the substrate specificity, for example. A comparison is made by correlating similar sequences in the nucleotide or amino acid sequences of the proteins under consideration. This is called "homologization". A tabular classification of the relevant positions is called alignment. When analyzing the nucleotide sequences the two complementary strands as well as each of the three possible open reading frames must be taken into account, likewise the degeneracy of the genetic code and the organism-specific codon usage. Alignments are now produced with the aid of computer programmes such as the algorithms FASTA or BLAST; this procedure is described by D. J. Lipman and W. R. Pearson (1985) in *Science*, Volume 227, pp. 1435-1441. The preferred method is using algorithms, which are now used by commercially available computer programmes. This includes for example the programme Vector NTI® Suite 7.0, available from InforMax, Inc., Bethesda, USA, preferably with the given default parameters.

A compilation of all the matching positions in the compared sequences is called a "consensus sequence".

Such a comparison also enables a statement to be made regarding the similarity or homology between the compared sequences. This is expressed in percent identity, i.e. the proportion of identical nucleotide or amino acid residues in the same positions. Another definition of homology includes the conserved amino acid exchanges in this value. It is then called percent similarity. Statements like these can be made about complete proteins and genes or just individual regions.

Constructing an "alignment" is the first step in defining a sequence space. This hypothetical space comprises all sequences derived by permutations in individual positions, which occur in consideration of all variations occurring in the relevant individual positions of the alignment. Each hypothetically possible protein molecule forms a point in this sequence space. For example two amino acid sequences, which, while being largely identical, have two different amino acids each in just two different places, thus justify a sequence space of four different amino acid sequences. A very large sequence space is obtained, when additional homologous sequences are found for each individual sequence in a space. Sequences of very low homology can also be recognized as belonging to a sequence space via such high homologies existing pairwise in each case.

"Homologous regions" of different proteins are described by correlations in the amino acid sequence. This goes as far as full identity in the smallest regions, known as boxes, which comprise only a few amino acids and perform functions essential mostly to the overall activity. The functions of the homologous regions refer to the smallest partial functions of the function performed by the whole protein, such as, for example, the formation of individual hydrogen bonding-type bonds for the complexation of a substrate or a transition complex.

The perhydrolases according to the invention preferably have a high specific rate of percarboxylic acid formation. It is preferably determined as in example 3 and indicated in ppm AO per µg enzyme.

The pH profile of the enzyme according to the invention is preferably compatible with the required pH for technical use, and also with typical ingredients in, for example, washing and cleaning agents and hair dyes. In most cases this is an alkaline environment; the starting enzyme, the subtilisin Carlsberg, is preferably also an alkaline protease. Thus, depending on the intended technical field of application, preferred inventive perhydrolases preferably have a pH optimum in the alkaline range from approximately pH 7 to pH 12, with pH 8 to pH 10 being especially preferred.

The temperature optimum of the preferred inventive perhydrolases ranges from 20 to 60° C., especially at around 30 to 50° C., likewise depending on the intended technical field of application.

The preferred inventive perhydrolases are those, whose amino acid sequence corresponds to the amino acid sequence indicated in SEQ ID NO. 23, yet has one or more amino acid exchanges at the sequence positions chosen from 11, 58, 77, 89, 96, 117, 120, 134, 135, 136, 140, 147, 150, 161, 208, 216, 217, 238.

Further preferred inventive perhydrolases are those, whose amino acid sequence corresponds to the amino acid sequence indicated in SEQ ID NO. 23, yet has one or more amino acid exchanges at the sequence positions chosen from 58, 89, 96, 117, 216, 217. This is because variants with exchanges in these positions have been successfully tested in the examples for the present application.

In addition, the preferred inventive perhydrolases are those, which are characterized by one or more of the amino acid exchanges T58A or T58Q, L89S, N96D, G117D, L216W and N217D. This is because variants with these exchanges have been successfully tested in the examples for the present application.

In addition the preferred inventive perhydrolases are those with one of the amino acid sequences indicated by SEQ ID NO. 2 (L89S/L216W/N217D), SEQ ID NO. 4 (L216W/N217D), SEQ ID NO. 6 (T58A/L89S/L216W/N217D), SEQ ID NO. 8 (T58A/G117D/L216W/N217D), SEQ ID NO. 10 (T58A/L89S/L216W), SEQ ID NO. 12 (T58A/L89S/N96D/L216W), SEQ ID NO. 14 (T58A/L216W), SEQ ID NO. 16 (T58Q/L89S/L216W) and SEQ ID NO. 18 (L89S/L216W). This is because these variants have been successfully tested in examples 3 and 4 of the present application. As shown there, they have a perhydrolase activity indicated in ppm AO pro μg enzyme, which is at least 1.7 times above the value indicated for the wild-type enzyme of the protease Carlsberg.

In addition, the increasingly preferred embodiments of the present invention are perhydrolases, whose amino acid sequence agrees increasingly preferably in each case at least 70%, 72.5%, 75%, 77.5%, 80%, 82.5%, 85%, 87.5%, 90%, 92.5%, 95%, 97.5% and particularly preferably 100% with one of the amino acid sequences indicated in the SEQ ID NO. 2, 4, 6, 8, 10, 12, 14, 16 or 18. In this example and below the term "at least X %" means "X % to 100% (including the bench mark figures X and 100 and all whole and non-whole percentage values in between)".

Likewise a particularly preferred nucleic acid, which codes for a perhydrolase is one, whose nucleotide sequence comprises a part, which is increasingly preferably at least 60%, 62.5%, 65%, 67.5%, 70%, 72.5%, 75%, 77.5%, 80%, 82.5%, 85%, 87.5%, 90%, 92.5%, 95%, 97.5% and quite particularly preferably 100% identical to one of the nucleotide sequences indicated in the SEQ ID NO. 1, 3, 5, 7, 9, 11, 13, 15 or 17 in each case. This is because, particularly through cloning and expression of the associated nucleic acids, the perhydrolases according to the invention are made available in the required quantity for the technical application as indicated below.

Further embodiments of the present invention are perhydrolases, which are obtained through one or more conservative amino acid exchanges from one of the perhydrolases described above, preferably within the homology values indicated here for the amino acid and nucleotide sequences. Conservative amino acid exchanges refer to those within the following amino acid groups:

aliphatic amino acids: G, A, V, L, I;
sulfur containing amino acids: C, M;
aromatic amino acids: F, Y, W;
hydroxyl group amino acids: S, T;
acid amide group amino acids: N, Q;
acid amino acids: D, E;
alkaline amino acids: H, K, R, P.

Further embodiments of the present invention are those perhydrolases, which are obtained from one of the perhydrolases described above by means of derivatization, fragmentation, deletion mutation or insertion mutation, preferably within the homology values indicated above for the amino acid and nucleotide sequences.

The oligonucleotides with the sequences indicated in SEQ ID NO. 19 to 21 represent a further subject of the invention. With the aid of these oligonucleotides, as shown in examples 1 and 2 of the present application, the nucleotide sequence which codes for the wild-type subtilisin Carlsberg, and also the nucleotide sequences, which code for point variants can be detected in corresponding genetic elements and, in particular, amplified by PCR and mutagened. Thus they are available for molecular biological processing and in particular for possible further point mutagensis.

Also included in the subject of this invention is the use of one or more of the oligonucleotides indicated in SEQ ID NO. 19 to 21 as a PCR primer, especially for identifying and/or producing a novel perhydrolase. Preferably they are used in pairs PSC-s and PSC-as (SEQ ID NO. 19 and 20 respectively) and pairs P300-s and PSC-as (SEQ ID NO. 21 and 20 respectively), as described in the examples.

A further subject of the invention is the use of one of the perhydrolases described above to fuse or couple with another protein, especially for the purpose of developing a new enzyme. Thus, for example, it is possible to obtain bifunctional molecules via direct fusion of the polypeptide chains or via chemical coupling, such as those from a Carlsberg variant according to the invention as perhydrolases and from another protease (for example Carlsberg) variant as proteolytic components, for example. Another option would be coupling to a cellulose-binding domain to improve the interaction of the perhydrolases with, for example, textiles containing cotton.

A further subject of the invention is the use of a nucleic acid, which codes for one of the perhydrolases described above, to fuse with another nucleic acid, especially for the purpose of developing a new enzyme. As stated above, bifunctional proteins can be obtained in this way.

Vectors, especially cloning or expression vectors, which contain one of the nucleic acid regions described above which code for perhydrolases according to the invention, represent a further subject of the invention. This includes, for example, those derived from bacterial plasmids, viruses or bacteriophages, or predominantly synthetic vectors or plasmids containing elements of different origin. With the other existing genetic elements in each case, the vectors are able to establish themselves as stable units in the respective host cells over several generations. Thus in the context of the invention it is irrelevant, whether they establish themselves as single extra-chromosomal units or whether they integrate in a chromosome. Which of the numerous systems known from the prior background is chosen, depends on the individual case. The decisive factor could be, for example, the number of copies achievable, the selection systems available, including in particular antibiotic resistance, or the cultivability of the host cells capable of accepting vectors.

The vectors make suitable starting points for molecular biological and biochemical investigations of the gene in question and the associated proteins, for further inventive developments and for the amplification and production of proteins according to the invention.

Cloning vectors are the preferred embodiments of the present invention. In addition to their suitability in terms of storage, biological amplification or selection of the gene in question, they are also suitable for characterizing the gene in question, for example by producing a restriction map or by sequencing. Cloning vectors are therefore also the preferred embodiments of the present invention, because they represent a transportable and storable form of the required DNA. They are also preferred starting points for molecular biological techniques, which are not involved with cells, such as polymerase chain reaction.

Expression vectors are chemically similar to cloning vectors, but can be distinguished by their partial sequences, which enable them to replicate in host organisms optimized for protein production, and to express the contained gene in them. Preferred embodiments of the expression vectors are those, which carry the genetic elements required for expression. Expression is, for example, influenced by promoters, which regulate the transcription of the gene. Thus expression can be carried out by the natural promoter originally located outside this gene, and also via genetically engineered fusion both by a host cell promoter on the expression vector and also by a modified or completely different promoter from another organism.

Preferred embodiments are those expression vectors, which can be regulated by changes to the cultural conditions or addition of certain compounds, such as cell density or special factors. Expression vectors enable the associated protein to be produced heterologously, i.e. in an organism other than the one from which it can be naturally produced. Even a homologous production of a protein from a host organism, which naturally expresses the gene, via a suitable vector lies within the scope of the present invention. This can have the advantage of enabling natural modification reactions relating to the translation to be conducted on the developing protein exactly as they would occur naturally.

Host cells, which express or can be activated to express one of the previously described inventive proteins or derivatives, preferably using one of the previously described expression vectors, represent a further subject of the invention.

Embodiments of the present invention can also be cell-free expression systems, where protein biosynthesis is conducted in vitro. Expression systems of this type are already established in the prior art. However, the in vivo synthesis of an enzyme according to the invention, in other words synthesis by living cells, is preferred. It requires the transfer of the associated gene into a host cell, which is known as transformation. In principle all organisms make suitable host cells, i.e. prokaryotic, eukaryotic or archea. Preferred host cells are those, which are genetically easily handled with regard to the transformation and stable establishment of the expression vector, for example, such as single-celled fungi or bacteria. Preferred host cells are further characterized by good microbiological and biotechnological handlability. This, for example, relates to ease of cultivation, high growth rates, low requirements in terms of fermentation media and good production and secretion rates for foreign proteins. It is often necessary to experiment with the range of different systems available according to the prior art to find the optimal expression system for an individual case. Each protein according to the invention can be produced in this way from a multitude of host organisms.

Preferred embodiments of host cells are those whose activity can be regulated by genetic regulating elements, which are present for example on the expression vector, but which can also be present in these cells from the outset. For example expression can be activated in these cells by the controlled addition of chemical compounds, which serve as activators, by changing the cultural conditions or when a certain cell density is achieved. This enables the proteins in question to be produced very economically. Preferred host cells are corresponding prokaryotic or bacterial cells.

Preferred host cells are therefore characterized by the fact that they are bacteria, in particular those, which secrete the produced protein or derivative into the surrounding medium. This is because bacteria can be distinguished from eukaryotes generally by shorter generation times and less exacting requirements in terms of cultural conditions. Thus economical procedures for producing proteins according to the invention can be established. Gram-negative bacteria such as *E. coli* secrete a range of proteins into the periplasmatic space, that is the compartment between the two membranes enclosing the cells. This can be beneficial for special applications. In contrast Gram-positive bacteria such as *Bacilli* or Actinomycetes or others belonging to the actinomycetal group have no external membrane, thus the secreted proteins are released straight into the nutritive medium surrounding the cells. The expressed proteins according to the invention are cleaned up straight form there in accordance with another preferred embodiment.

Expression systems whereby additional genes, for example those present on other vectors, influence the production of the inventive proteins represent a variation of this experimental principle. These may be modified genetic products or ones, which have been cleaned up together with the inventive protein, in order to influence their enzymatic function, for example. They may be other proteins or enzymes, inhibitors or other elements, which influence the interaction with different substrates.

Preferred host cells are those belonging to the genus, preferably also to the species *Bacillus licheniformis, Bacillus amyloliquefaciens, Bacillus subtilis* or *Bacillus alcalophilus*. This is because there is a wealth of knowledge relating to the fermentive protein production for this genus and/or species and they are alkaliphile, like *B. licheniformis* itself, from which subtilisin Carlsberg originates.

Eukaryontic cells represent another embodiment of host cells, preferably of the genus *Saccharomyces*, especially those that modify the produced protein after translation. This is because eukaryontic cells are also suitable for the production of proteins according to the invention. Examples of this apart from yeasts such as *Saccharomyces* or *Kluyveromyces* are fungi such as actinomycetes for example. This can be particularly advantageous if the proteins are to undergo special modifications relating to their synthesis. This includes, for example, the bonding of low-molecular compounds such as membrane anchors or oligosaccharides.

The host cells of the inventive procedure are cultivated and fermented in a way known per se, for example in discontinuous or continuous systems. In the former case a suitable nutritive medium is inoculated with the organisms and the product is then harvested from the medium after a period of time to be determined. With continuous fermentations, on the other hand, a steady state is reached, whereby over a comparatively long period of time some cells die, but also regrow and the product can be harvested from the medium at the same time.

Fermentation techniques are well known per se from the prior art and represent the actual large-scale production step, followed by a suitable cleaning up method.

All fermentation techniques based on one of the procedures outlined above to produce the recombinant proteins are therefore preferred embodiments of the subject of this invention.

In each case the optimum conditions for the appointed production methods and for the host cells and/or proteins to be produced must be determined by experimentation on the basis of both the previously optimized cultural conditions of the relevant strains and the skilled person's knowledge relating to, for example, fermentation volumes, media composition, oxygen supply or agitator speed.

Fermentation techniques, which are conducted using a feed strategy, can also be considered. This involves feeding or charging the media components, which are consumed by continual cultivation, also called feeding strategy. Considerable increases in cell density, dry weight of biomass and/or especially activity of the protein in question can be achieved using this method.

Likewise the fermentation can be structured in such a way that undesirable metabolic products are filtered out or neutralized by the addition of buffers or suitable counterions.

The produced protein can then be harvested from the fermentation medium. This fermentation technique is preferred to processing the product from the dry weight, but does however require suitable secretion markers and transport systems to be in place.

Without secretion it is sometimes necessary to clean up the protein from the cell mass. There are several known techniques for doing this, such as precipitation with ammonium sulfate or ethanol, for example, or chromatographic purification, to homogeneity if required. However, the majority of the techniques described require an enriched, stabilized preparation.

All the elements mentioned above can be combined with the process to produce inventive proteins. Thus for each inventive protein there is a range of possible combinations of production steps. The optimum process for each individual case must be determined by experiment.

The use of one of the previously described inventive perhydrolases as an agent producing percarboxylic acid in situ is an actual subject of the invention. Since although subtilisin Carlsberg itself and variants of this enzyme have hitherto been used in particular as proteolytic components, the increased perhydrolase activity resulting from the described amino acid exchanges reveals a new application for the inventive variants. Preferably this application will be effected with appropriately designed agents formulated for the respective purpose.

This application can be used in bleaches and disinfectants, especially in disinfectants or agents for bleaching and disinfecting filter media, textiles, furs, paper, hides and leather.

This application can also be used in washing or cleaning agents, especially laundry detergents, cleaning agents, rinsing agents, hand-washing agents, washing-up liquids or dishwasher agents, most especially as a color transfer inhibitor for laundry detergents. In the latter case the perhydrolases bleach the colored particles in the washing liquor, preventing them from recoloring the textiles in the liquor as strongly.

This application can also be used in cosmetics and beauty preparations, especially in body care products, shampoos, hair care products, hair dying or bleaching agents, mouth, teeth and denture care products.

An inventive perhydrolase is preferably used in quantities, whereby the total amount has a perhydrolase activity of 0.05 to 5 ppm AO/µg, preferably 0.2 to 1.2 ppm AO/µg. For example, detergents with perhydrolase activities in the said areas release percarboxylic acid sufficiently quickly for standard European machine washing procedures; increasing the quantity of perhydrolase to achieve increased activity generally does not bring about a corresponding increase in bleach performance. The quantity of substrate for the perhydrolases in the relevant agents corresponds to the quantity of percarboxylic acid required to achieve the desired bleaching result and can be adjusted as required by the skilled person.

Agents, which contain one of the previously mentioned inventive perhydrolases, represent a further subject of the invention. In particular these include body care products, shampoos, hair care products, hair dying or bleaching agents, mouth, teeth and denture care products, cosmetics and beauty products, laundry detergents, cleaning agents, rinsing agents, hand-washing agents, washing-up liquids, dishwasher detergents, disinfectants and agents for bleaching and disinfecting filter media, textiles, furs, paper, hides and leather which contain such a perhydrolase.

Amongst these, preference is given to detergents or bleaches containing a bleaching system capable of producing percarboxylic acid under the conditions of application of the agent and optionally, synthetic surfactants, organic and/or inorganic builders and other standard components of bleaches or detergents. The bleaching system characteristically comprises one of the previously described inventive perhydrolases, a hydrogen peroxide source and a substrate for the perhydrolase.

Preferred detergents or bleaches are those, where the substrate is derived from methyl, ethyl and glycerol esters of butanoic acid, hexanoic acid or octanedioic acid, preferably methyl butyrate, methyl hexanoate, methyl octanoate and trioctanoin and particularly preferably methyl butyrate. Thus, a methyl butyrate is also used in the reaction batch to determine the perhydrolase activity in accordance with examples 3 and 4 and the same ester is present in the applied measurements for examples 5 and 6.

Other preferred detergents and bleaches are those where the hydrogen peroxide source is selected from sodium percarbonate, sodium perborate or potassium monopersulfate-triple salt, salt mixtures of percarbonate/potassium persulfate in a ratio of 1 to 3 (pH 5.5); percarbonate/potassium persulfate in a ratio of 1 to 1 (pH 7.5); percarbonate/potassium persulfate in a ratio of 3 to 1 (>pH 9) and especially preferred $H_2O_2$. So $H_2O_2$ is also used as the source of hydrogen peroxide in the corresponding reaction batches in examples 3, 4, 5 and 6.

According to the statements above a preferred inventive detergent or bleach has a perhydrolytic activity ranging from 0.05 to 5 ppm AO/µg, preferably 0.2 to 1.2 ppm AO/µg.

According to the statements above a preferred inventive detergent or bleach is in the form of tablets, granules or free flowing powder with a bulk density ranging from 300 µl to 1200 g/l, especially 500 g/l to 900 g/l. This particularly applies to dishwasher and laundry detergents.

Other equally preferred detergents or bleaches are in the form of pastes or liquids.

Below, the preferred embodiments are characterized as non-aqueous.

Additionally preferred embodiments are all inventive agents described so far, where the perhydrolase and/or the substrate for this enzyme and/or the hydrogen peroxide source is enveloped in a substance impermeable to the enzyme and/or its substrate at room temperature or in the absence of water, but which becomes permeable to the enzyme and/or its substrate under the application conditions of the agent. This aims to protect the constituents from premature deactivation, by reacting with atmospheric oxygen or humidity, for example, on the one hand, whilst on the other hand protecting the other constituents of the agents in question from oxidition by these aggressive constituents. In addition or alternatively, the agent can also be packed in a receptacle, from where it can be released just before or during application of the washing procedure for instance.

Additionally preferred embodiments of all inventive detergents or bleaches described so far are those, which contain in addition to the bleaching system:

5-70 wt. %, especially 10-50 wt. % of surfactants
10-65 wt. %, especially 12-60 wt. % of water-soluble, water-dispersible, inorganic builder material
1-10 wt. %, especially 2-8 wt. % of water-soluble inorganic builder substances
no more than 15 wt. % of solid, inorganic and/or organic acids or acid salts
no more than 5 wt. % of complexing agents for heavy metals
no more than 5 wt. % of graying inhibitors
no more than 5 wt. % of colour transfer inhibitors
no more than 5 wt. % of foam inhibitors and
other optional ingredients.

In view of their considerable technical significance, the different aspects and other ingredients of the inventive washing and cleaning agents, i.e. those characterized by the perhydrolases described above, will now be described in detail to supplement the especially preferred embodiments described previously.

Throughout the world a distinction is made in cleaning terms between textiles and solid surfaces. The conditions to select, especially those to be controlled by other ingredients, such as temperature, pH value, ionic strength, redox ratios or mechanical factors should be optimized for each individual cleaning problem. Thus standard temperatures for washing and cleaning agents lie in the region of 110C to 40° C. for hand washing, and 60° C. right up to 95° for machine washing or for technical applications. Since the temperature can generally be progressively adjusted in modern washing machines and dishwashers, all intermediate levels of temperature are also included. The constituents of the agents in question are preferably compatible with one another. Preferably there are synergies relating to the cleaning performance.

An inventive perhydrolase may be applied both to products for bulk consumers or technical users and to products for private consumers, including all types of cleaning agent established in the prior art including embodiments of the present invention. This comprises for example (a) concentrates and agents, which are used in undiluted form on a commercial scale in washing machines or for hand washing and cleaning, (b) detergents for textiles, carpets or natural fibers, for which the term "detergent" is used in accordance with the present invention, and (c) dishwasher detergents, washing-up liquids and cleaners for hard surfaces like metal, glass, porcelain, ceramics, tiles, stone, painted surfaces, plastics, wood or leather, for which the term "cleaning agent" is used in accordance with the present invention.

Embodiments of the present invention comprise all established and/or all suitable packaging formats. This includes for example solids, powders, liquids, gels and pastes, optionally also in several phases, either compressed or uncompressed. In addition it also includes extrudates, granules, tablets and sachets, packed individually or in bulk.

The inventive perhydrolases are combined in the agent according to the invention with one or several of the following ingredients: nonionic, anionic or cationic surfactants, (possible additional) bleaches, bleach activators, bleach catalysts, builders and/or cobuilders, solvents, thickeners, sequestrants, electrolytes, optical brighteners, graying inhibitors, corrosion inhibitors, especially silver protectants, soil-release agents, colour transfer inhibitors, foam inhibitors, abrasives, colorants, perfumes, anti-microbial agents, UV protectants, enzymes, such as proteases, amylases, lipases, cellulases, hemicellulases and oxidases, stabilizers, especially enzyme stabilizers, and other components, which are known from the prior art.

Preferred non-ionic surfactants are alkoxylated, ideally ethoxylated, especially primary alcohols with preferably 8 to 18 carbon atoms and on average 1 to 12 mol ethylenoxide (EO) per mol alcohol, in which the alcohol residue can be linear or preferably methyl-branched in the 2-position, or can contain linear and methyl-branched residues in the mixture, as are usually present in oxoalcohol residues. However, especially preferred are alcohol ethoxylates with linear residues of natural alcohols with 12 to 18 carbon atoms, for example from cocoa, palm, tallow or oleyl alcohol, and on average 2 to 8 EO per mol alcohol. The preferred ethoxylated alcohols include for example $C_{12-14}$ alcohols with 3 EO or 4 EO, $C_{9-11}$ alcohol with 7 EO, $C_{3-15}$ alcohols with 3 EO, 5 EO, 7 EO or 8 EO, $C_{12-18}$ alcohols with 3 EO, 5 EO or 7 EO and combinations of these, such as $C_{12-14}$ alcohol with 3 EO and $C_{12-18}$ alcohol with 5 EO. The indicated degrees of ethoxylation represent statistical mean values, which for a specific product can be a whole or fractional number. The preferred alcohol ethoxylates are narrow range ethoxylates (NRE). In addition to these nonionic surfactants, fatty alcohols with more than 12 EO can also be used. Examples of these include tallow alcohols with 14 EO, 25 EO, 30 EO or 40 EO.

A further class of preferred nonionic surfactants, which can either be used individually or in combination with other non-ionic surfactants, are alkoxylated, preferably ethoxylated or ethoxylated and propoxylated fatty acid alkyl esters, preferably with 1 to 4 carbon atoms in the alkyl chain, especially fatty acid methyl esters.

A further class of preferred nonionic surfactants are alkyl polyglycosides (APG). Suitable alkyl polyglycosides correspond to the general formula $RO(G)_z$, where R denotes a linear or branched, especially methyl-branched in the 2-position, saturated or unsaturated aliphatic residue with 8 to 22, preferably 12 to 18 carbon atoms and G is the symbol for a glycose unit with 5 or 6 carbon atoms, preferably glucose. The degree of glycosylation z lies between 1.0 and 4.0, preferably between 1.0 and 2.0 and especially between 1.1 and 1.4. Linear alkyl polyglycosides, that is those where the polyglycoside residue is a glucose residue and the alkyl residue is an n-alkyl residue, are preferred.

Non-ionic surfactants of the amine oxide type, for example N-cocoalkyl-N,N-dimethylamine oxide and N-tallow-alkyl-N,N-dihydroxyethylamine oxide, and of the fatty acid alkanolamides can also be suitable. The proportion of these non-ionic surfactants is preferably below that of the ethoxylated fatty alcohols, especially less than half.

Further suitable surfactants are polyhydroxy fatty acid amides corresponding to formula (II),

where RCO is an aliphatic acyl residue with 6 to 22 carbon atoms, $R^1$ is hydrogen, an alkyl or hydroxyalkyl residue with 1 to 4 carbon atoms and [Z] is a linear or branched polyhydroxyl alkyl residue with 3 to 10 carbon atoms and 3 to 10 hydroxyl groups. The polyhydroxy fatty acid amides are known substances, which are normally obtained by reductive amination of a reducing sugar with ammonia, an alkyl amine or an alkanolamine and subsequent acylation with a fatty acid, a fatty alkyl ester or a fatty acid chloride.

The polyhydroxy fatty acid amides group also includes compounds corresponding to formula (III),

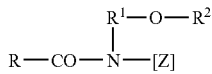
(III)

where R is a linear or branched alkyl or alkenyl residue with 7 to 12 carbon atoms, $R^1$ is a linear, branched or cyclic alkyl or aryl residue with 2 to 8 carbon atoms and $R^2$ is a linear, branched or cyclic alkyl, aryl or oxyalkyl residue with 1 to 8 carbon atoms, where $C_{1-4}$ alkyl or phenyl residues are preferred and [Z] is a linear polyhydroxyl alkyl residue, whose alkyl chain is substituted with at least two hydroxyl groups, or alkoxylated, preferably ethoxylated and propoxylated derivatives of this residue.

[Z] is preferably obtained by reductive amination of a reducing sugar such as glucose, fructose, maltose, lactose, galactose, mannose or xylose. The N-alkoxy or N-aryloxy substituted compounds can be converted to the required polyhydroxy fatty acid amides by reaction with fatty acid methyl esters in the presence of an alkoxide as catalyst.

Anionic surfactants of the sulfonate or sulfate type, for example, are used. Sulfonate surfactants to consider are preferably $C_{9-13}$ alkylbenzene sulfonates, olefin sulfonates, that is mixtures of alkene and hydroxyalkane sulfonates and disulfonates, as are obtained, for example, from $C_{12-18}$ mono olefins with terminal or internal double bonds by sulfonation with gaseous sulfur trioxide and subsequent alkaline or acidic hydrolysis of the sulfonation product. Also suitable are alkane sulfonates, which can for example be obtained from $C_{12-18}$ alkanes by sulfochlorination or sulfoxidation with subsequent hydrolysis or neutralization. Esters of α-sulfo fatty acids (sulfonate esters) are also suitable, for example the α-sulfonated methylester of hydrogenated coco, palm kernel or tallow fatty acids.

Sulfated fatty acid esters of glycerol are further suitable anionic surfactants. They include the mono-, di- and triesters and also mixtures of them, such as those obtained by the esterification of a monoglycerol with 1 to 3 mols fatty acid or the transesterification of triglycerides with 0.3 to 2 mols glycerol. Preferred sulfated fatty acid esters of glycerol in this case are the sulfated products of saturated fatty acids with 6 to 22 carbon atoms, for example hexanoic acid, octanoic acid, decanoic acid, myristic acid, lauric acid, palmitic acid, stearic acid or behenic acid.

Preferred alk(en)yl sulfates are the alkaline and especially sodium salts of the sulfuric acid half-ester derived from the $C_{12}$-$C_{18}$ fatty alcohols, for example from coconut butter alcohol, tallow alcohol, lauryl, myristyl, cetyl or stearyl alcohol or from $C_{10}$-$C_{20}$ oxo alcohols and those half-esters of secondary alcohols with these chain lengths. Further preferred are alk(en)yl sulfates of the said chain lengths, which contain a synthetic, straight-chained alkyl residue produced on a petrochemical basis, which shows similar degradation behaviour to the suitable compounds on the basis of fatty chemical raw materials. The $C_{12}$-$C_{16}$, $C_{12}$-$C_{15}$ and $C_{14}$-$C_{15}$ alkyl sulfates are preferred on the grounds of laundry performance. The 2,3-alkyl sulfates are also suitable anionic surfactants.

Sulfuric acid mono-esters derived from straight-chained or branched $C_{7-21}$ alcohols ethoxylated with 1 to 6 mols ethylene oxide are also suitable, for example 2-methyl-branched $C_{9-11}$ alcohols with an average of 3.5 mol ethylene oxide (EO) or $C_{12-18}$ fatty alcohols with 1 to 4 EO. They are only used in fairly small quantities in cleaning agents due to their high foaming performance, for example up to 5% by weight, generally from 1 to 5% by weight.

Other suitable anionic surfactants are the salts of alkylsulfosuccinic acid, which are also referred to as sulfosuccinates or esters of sulfosuccinic acid and the mono-esters and/or di-esters of sulfosuccinic acid with alcohols, preferably fatty alcohols and especially ethoxylated fatty alcohols. Preferred sulfosuccinates contain $C_{8-18}$ fatty alcohol residues or mixtures thereof. Especially preferred sulfosuccinates contain a fatty alcohol residue derived from the ethoxylated fatty alcohols that are under consideration as nonionic surfactants (see description below). Once again the especially preferred sulfosuccinates are those, whose fatty alcohol residues are derived from ethoxylated fatty alcohols with narrowed homolog distribution. It is also possible to use alk(en)ylsuccinic acid with preferably 8 to 18 carbon atoms in the alk(en)y chain or salts thereof.

Soaps in particular can be considered as further anionic surfactants. Saturated fatty acid soaps are suitable, such as the salts of lauric acid, myristic acid, palmitic acid, stearic acid, hydrogenated erucic acid and behenic acid, and especially soap mixtures derived from natural fatty acids such as coconut oil fatty acid, palm kernel oil fatty acid or tallow fatty acid.

Anionic surfactants, including soaps, may be in the form of their sodium, potassium or ammonium salts or as soluble salts of organic bases, such as mono-, di- or triethanolamine. Preferably, anionic surfactants are in the form of their sodium or potassium salts, especially sodium salts.

The surfactants may be contained in the inventive washing and cleaning agents in a total quantity of preferably 5%-50% by weight, especially 8% to 30% by weight, depending on the finished product.

Inventive agents may contain additional bleaching agents. Among the compounds, which serve as bleaches and liberate $H_2O_2$ in water, sodium percarbonate, sodium perborate tetrahydrate and sodium perborate monohydrate are of particular importance. Other suitable bleaches are, for example, peroxypyrophosphates, citrate perhydrates and $H_2O_2$— supplying peracid salts or peracids, such as persulfates or persulfuric acids. Also useful is the urea peroxohydrate percarbamide, which can be described by the formula $H_2N$—CO—$NH_2.H_2O_2$. The agents may also contain bleaches from the organic group, especially when used for cleaning hard surfaces, as in dishwashers for example, although they are principally used in laundry products. Typical organic bleaches are the diacyl peroxides, such as dibenzoyl peroxide. Further typical organic bleaches are the peroxy acids, especially the alkylperoxy acids and arylperoxy acids. Preferred representatives that can be used here are (a) peroxybenzoic acid and their ring-substituted derivates, such as alkylperoxybenzoic acid, and also peroxy-α-naphthoic acid and magnesium monoperphthalate, (b) the aliphatic or substituted aliphatic peroxy acids, such as peroxylauric acid, peroxystearic acid, ε-phthalimideoperoxycaproic acid (phthaloiminoperoxyhexanoic acid, PAP), o-carboxybenzamido peroxycaproic acid, N-nonenylamidoperadipic acid and N-nonenylamido persuccinates, and (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyl-di(6-aminopercaproic acid).

The bleach content of the agent may be 1 to 40% by weight and especially 10 to 20% by weight, with perborate monohydrate or percarbonate being preferably used. Applications WO 99/63036 and WO 99/63037 disclose a synergistic use of amylase with percarbonate or amylase with percarboxylic acid.

For washing at temperatures of 60° C. and below, and especially in laundry pre-treatments, the agent may also comprise bleach activators in order to achieve an improved bleaching action. Suitable bleach activators are compounds which, under perhydrolysis conditions, produce aliphatic peroxycarboxylic acids having preferably 1 to 10 carbon atoms, in particular 2 to 4 carbon atoms, and/or optionally substituted perbenzoic acid. Substances, which carry O-acyl and/or N-acyl groups of said number of carbon atoms and/or optionally substituted benzoyl groups, are suitable. Preference is given to polyacylated alkylenediamines, in particular tetraacetyl ethylenediamine (TAED), acylated triazine derivatives, in particular 1,5-diacetyl-2,4-dioxohexahydro-1,3,5-triazine (DADHT), acylated glycolurils, in particular 1,3,4, 6-tetraacetyl glycoluril (TAGU), N-acylimides, in particular N-nonanoyl succinimide (NOSI), acylated phenolsulfonates, in particular n-nonanoyl- or isononanoyloxybenzenesulfonate (n- or iso-NOBS), acylated hydroxycarboxylic acids, such as triethyl-O-acetyl citrate (TEOC), carboxylic acid anhydrides, in particular phthalic anhydride, isatinic acid anhydride and/or succinic acid anhydride, carboxylic acid amides, such as N-methyldiacetamide, glycolids, acylated polyhydric alcohols, in particular triacetin, ethylene glycol diacetate, isopropenyl acetate, 2,5-diacetoxy-2,5-dihydrofuran and the enol esters disclosed in German patent applications DE 196 16 693 and DE 196 16 767 such as acylated sorbitol and mannitol or mixtures of them (SORMAN) as described in European patent application EP 0 525 239, acylated sugar derivatives, especially pentaacetylglucose (PAG), pentaacetylfructose, tetraacetylxylose and octaacetyllactose and acylated, optionally N-alkylated glucamine or gluconolactone, triazole or triazole derivatives and/or particle-shaped caprolactam and/or caprolactam derivatives, especially N-acylated lactam, for example N-benzoylcaprolactam and N-acetylcaprolactam, which are disclosed in international patent applications WO 94/27970, WO 94/28102, WO 94/28103, WO 95/00626, WO 95/14759 and WO 95/17498. The hydrophilically substituted acyl acetals disclosed in German patent application DE 196 16 769 and the acyl lactams disclosed in German patent application DE 196 16 770 and international patent application WO 95/14075 are likewise preferably used. The combination of conventional bleach activators disclosed in German patent application DE 44 43 177 may also be used. Likewise nitrile derivatives such as cyanopyridine, nitrile quats, for example N-alkylammonium acetonitrile, and/or cyanamide derivatives may be used. Preferred bleach activators are sodium-4-(octanoyloxy)-benzene sulfonate, n-nonanoyl or iso-nonanoyloxybenzene sulfonate (n- or iso-NOBS), undecanoyloxybenzene sulfonate (UDOBS), sodium dodecanoyloxybenzene sulfonate (DOBS), decanoyloxybenzoic acid (DOBA, OBC 10) and/or dodecanoyloxybenzene sulfonate (OBS 12), and N-methyl-morpholine-acetonitrile (MMA). Typically these bleach activators are present in amounts of 0.01 to 20% by weight, preferably 0.1 to 15% by weight and especially 1-10% by weight, based on the total formulation.

The formulation may also comprise bleach catalysts in addition to, or instead of conventional bleach activators. These are bleach-enhancing transition metal salts and complexes, for example Mn, Fe, Co, Ru or Mo salt complexes or carbonyl complexes. Other suitable bleach catalysts are Mn, Fe, Co, Ru, Mo, Ti, V and Cu complexes with N-containing tripod ligands and Co, Fe, Cu and Ru amine complexes, with those compounds disclosed in DE 197 09 284 A1 especially preferred. Acetone nitrile derivatives and bleach-activating transition metal complex compounds with amylases may also serve as bleach activators according to WO 99/63038 and WO 99/63041 respectively.

Inventive agents generally contain one or several builders, especially zeolites, silicates, carbonates, organic cobuilders and—where there are no ecological reasons preventing their use—phosphates. The latter are especially preferred in dishwasher detergents.

Suitable silicate builders are the crystalline, layered sodium silicates corresponding to the general formula $NaMSi_xO2_{x+1}.yH_2O$, wherein M is sodium or hydrogen, x is a number from 1.6 to 4, preferably 1.9 to 4.0 and y is a number from 0 to 20, preferred values for x being 2, 3 or 4. These types of crystalline layered silicates are described, for example, in the European Patent application EP 0 164 514. Preferred crystalline, layered silicates of the given formula are those in which M stands for sodium and x assumes the values 2 or 3. Both β- and δ-sodium disilicates, $Na_2Si_2O_5.yH_2O$, are particularly preferred. These types of compounds are commercially available, for example, under the designation SKS® (Clariant). SKS-6® is predominantly a δ-sodium disilicate with the formula $Na_2Si_2O_5.yH_2O$, SKS-7® is predominantly a β-sodium silicate. On reaction with acids (e.g. citric acid or carbonic acid), δ-sodium disilicate yields Kanemite $NaHSi_2O_5.yH_2O$, which is commercially available under the designations SKS-9® and SKS-0® from Clariant. It can also be advantageous to initiate chemical modifications of these layered silicates. Thus, the alkalinity, for example, of the layered silicates can be suitably influenced. Layered silicates modified with phosphate or with carbonate have a modified crystal morphology in comparison to 8-sodium disilicate, dissolve faster and in comparison to 6-sodium disilicate show a higher calcium binding potential. Thus, layered silicates of the general formula $x\ Na_2O.ySiO_2.P_2O_5$, in which the ratio x to y corresponds to a number 0.35 to 0.6, the ratio x to z corresponds to a number from 1.75 to 1200 and the ratio y to z a number from 4 to 2800, are described in the Patent application DE 196 01 063. The solubility of the layered silicates can also be increased by the use of particularly finely dispersed layered silicates. Compounds of crystalline, layered silicates with other ingredients can also be used. Compounds with cellulose derivatives, which possess advantages in the disintegration action, and which are particularly used in washing agent tablets, as well as compounds with polycarboxylates, for example citric acid or polymeric polycarboxylates, for example copolymers of acrylic acid can be particularly cited in this context.

Other useful builders are amorphous sodium silicates with a modulus ($Na_2O:SiO2$ ratio) of 1:2 to 1:3.3, preferably 1:2 to 1:2.8 and more preferably 1:2 to 1:2,6 which dissolve with a delay and exhibit multiple wash cycle properties. The delay in dissolution compared with conventional amorphous sodium silicates can have been obtained in various ways, for example by surface treatment, compounding, compressing/compacting or by over-drying. In the context of the invention, the term "amorphous" is also understood to encompass "X-ray amorphous". In other words, the silicates do not produce any of the sharp X-ray reflexes typical of crystalline substances in X-ray diffraction experiments, but at best one or more maxima of the scattered X-radiation, which have a width of several degrees of the diffraction angle. However, particularly good builder properties may even be achieved where the silicate particles produce indistinct or even sharp diffraction maxima in electron diffraction experiments. This can be interpreted to mean that the products have microcrystalline regions between 10 and a few hundred nm in size, values of up to at most 50 nm and especially up to at most 20 nm being preferred. Compacted/densified amorphous silicates, compounded amorphous silicates and over dried X-ray-amorphous silicates are particularly preferred.

Of the optionally suitable fine crystalline, synthetic zeolites containing bound water, zeolite A and/or P are preferred. A particularly preferred zeolite P is zeolite MAPS (a commercial product of Crosfield). However, the zeolites X as well as mixtures of A, X and/or P are also suitable. Commercially available and preferred in the context of the present invention is, for example, also a co-crystallizate of zeolite X and zeolite A (ca. 80 wt. % zeolite X), which is marketed under the name of VEGOBOND AX® by Condea Augusta S.p.A. and which can be described by the Formula

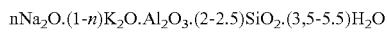

$nNa_2O.(1-n)K_2O.Al_2O_3.(2-2.5)SiO_2.(3,5-5.5)H_2O$

Suitable zeolites have a mean particle size of less than 10 μm (volume distribution, as measured by the Coulter Counter Method) and contain preferably 18 to 22% by weight and more preferably 20 to 22% by weight of bound water.

Naturally, the generally known phosphates can also be added as builders, in so far that their use should not be avoided on ecological grounds. In the washing and cleaning agent industry, among the many commercially available phosphates, the alkali metal phosphates are the most important and pentasodium or pentaalkalium triphosphates (sodium or potassium tripolyphosphate) are particularly preferred.

"Alkali metal phosphates" is the collective term for the alkali metal (more particularly sodium and potassium) salts of the various phosphoric acids, including metaphosphoric acids $(HPO_3)_n$ and orthophosphoric acid $(H_3PO_4)$ and representatives of higher molecular weight. The phosphates combine several advantages: they act as alkalinity sources, prevent lime deposits on machine parts and lime incrustations in fabrics and, in addition, contribute towards the cleaning effect.

Sodium dihydrogen phosphate $NaH_2PO_4$ exists as the dihydrate (density 1.91 $gcm^{-3}$, melting point 60° C.) and as the monohydrate (density 2.04 $gcm^{-3}$). Both salts are white, readily water-soluble powders that on heating, lose the water of crystallization and at 200° C. are converted into the weakly acidic diphosphate (disodium hydrogen diphosphate, $Na_2H_2P_2O_7$) and, at higher temperatures into sodium trimetaphosphate $(Na_3P_3O_9)$ and Maddrell's salt (see below). $NaH_2PO_4$ shows an acidic reaction. It is formed by adjusting phosphoric acid with sodium hydroxide to a pH value of 4.5 and spraying the resulting "mash". Potassium dihydrogen phosphate (primary or monobasic potassium phosphate, potassium biphosphate, KDP), $KH_2PO_4$, is a white salt with a density of 2.33 $gcm^{-3}$, has a melting point of 253° C. [decomposition with formation of potassium polyphosphate $(KPO_3)_x$] and is readily soluble in water.

Disodium hydrogen phosphate (secondary sodium phosphate), $Na_2HPO_4$, is a colorless, readily water-soluble crystalline salt. It exists in anhydrous form and with 2 mol (density 2.066 $gcm^{-3}$, water loss at 95° C.), 7 mol (density 1.68 $gcm^{-3}$, melting point 48° C. with loss of $5H_2O$) and 12 mol of water (density 1.52 $gcm^{-3}$, melting point 35° C. with loss of $5H_2O$), becomes anhydrous at 100° C. and, on fairly intensive heating, is converted into the diphosphate $Na_4P_2O_7$. Disodium hydrogen phosphate is prepared by neutralization of phosphoric acid with soda solution using phenolphthalein as indicator. Dipotassium hydrogen phosphate (secondary or dibasic potassium phosphate), $K_2HPO_4$, is an amorphous white salt, which is readily soluble in water.

Trisodium phosphate, tertiary sodium phosphate, $Na_3PO_4$, consists of colorless crystals with a density of 1.62 $gcm^{-3}$ and a melting point of 73-76° C. (decomposition) as the dodecahydrate, a melting point of 100° C. as the decahydrate (corresponding to 19-20% $P_2O_5$) and a density of 2.536 $gcm^{-3}$ in anhydrous form (corresponding to 39-40% $P_2O_5$). Trisodium phosphate is readily soluble in water through an alkaline reaction and is prepared by concentrating a solution of exactly 1 mole of disodium phosphate and 1 mole of NaOH by evaporation. Tripotassium phosphate (tertiary or tribasic potassium phosphate), $K_3PO_4$, is a white deliquescent granular powder with a density of 2.56 $gcm^{-3}$, has a melting point of 1340° C. and is readily soluble in water through an alkaline reaction. It is formed, for example, when Thomas slag is heated with coal and potassium sulfate. Despite their higher price, the more readily soluble and therefore highly effective potassium phosphates are often preferred to corresponding sodium compounds in the detergent industry.

Tetrasodium diphosphate (sodium pyrophosphate), $Na_4P_2O_7$, exists in anhydrous form (density 2.534 $gcm^{-3}$, melting point 988° C., a figure of 880° C. has also been mentioned) and as the decahydrate (density 1.815-1.836 $gcm^{-3}$, melting point 94° C. with loss of water). Both substances are colorless crystals, which dissolve in water through an alkaline reaction. $Na_4P_2O_7$ is formed when disodium phosphate is heated to more than 200° C. or by reacting phosphoric acid with soda in a stoichiometric ratio and spray drying the solution. The decahydrate complexes heavy metal salts and hardness salts and, hence, reduces the hardness of water. Potassium diphosphate (potassium pyrophosphate), $K_4P_2O_7$, exists in the form of the trihydrate and is a colorless hygroscopic powder with a density of 2.33 $gcm^{-3}$ which is soluble in water, the pH of a 1% solution at 25° C. being 10.4.

Relatively high molecular weight sodium and potassium phosphates are formed by condensation of $NaH_2PO_4$ or $KH_2PO_4$. They may be divided into cyclic types, namely the sodium and potassium metaphosphates, and chain types, the sodium and potassium polyphosphates. The chain types in particular are known by various different names: fused or calcined phosphates, Graham's salt, Kurrol's salt and Maddrell's salt. All higher sodium and potassium phosphates are known collectively as condensed phosphates.

The industrially important pentasodium triphosphate, $Na_5P_3O_{10}$ (sodium tripolyphosphate), is anhydrous or crystallizes with $6H_2O$ to a non-hygroscopic white water-soluble salt which and which has the general formula NaO—[P(O)(ONa)—O]$_n$—Na where n=3. Around 17 g of the salt free from water of crystallization dissolve in 100 g of water at room temperature, around 20 g at 60° C. and around 32 g at 100° C. After heating the solution for 2 hours to 100° C., around 8% orthophosphate and 15% diphosphate are formed by hydrolysis. In the preparation of pentasodium triphosphate, phosphoric acid is reacted with soda solution or sodium hydroxide in a stoichiometric ratio and the solution is spray-dried. Similarly to Graham's salt and sodium diphosphate, pentasodium triphosphate dissolves many insoluble metal compounds (including lime soaps, etc.). Pentapotassium triphosphate, $K_5P_3O_{10}$ (potassium tripolyphosphate), is marketed for example in the form of a 50% by weight solution (>23% $P_2O_5$, 25% $K_2O$). The potassium polyphosphates are widely used in the detergent industry. Sodium potassium tripolyphosphates, which may also be used in accordance with the present invention, also exist. They are formed for example when sodium trimetaphosphate is hydrolyzed with KOH:

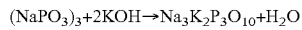

According to the invention, they may be used in exactly the same way as sodium tripolyphosphate, potassium tripolyphosphate or mixtures thereof. Mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate may also be used in accordance with the invention.

Organic co builders, which may be used in the washing and cleaning agents according to the invention, include, in particular, polycarboxylates or polycarboxylic acids, polymeric polycarboxylates, polyaspartic acid, polyacetals, optionally oxidized dextrins, other organic co builders (see below) and phosphonates. These classes of substances are described in the following.

Useful organic builders are, for example, the polycarboxylic acids usable in the form of their sodium salts, polycarboxylic acids in this context being understood to be carboxylic acids that carry more than one acid function. These include, for example, citric acid, adipic acid, succinic acid, glutaric acid, malic acid, tartaric acid, maleic acid, fumaric acid, sugar acids, aminocarboxylic acids, nitrilotriacetic acid (NTA), providing its use is not ecologically unsafe, and mixtures thereof. Preferred salts are the salts of polycarboxylic acids such as citric acid, adipic acid, succinic acid, glutaric acid, tartaric acid, sugar acids and mixtures thereof.

The acids per se may also be used. Besides their building effect, the acids also typically have the property of an acidifying component and, hence also serve to establish a relatively low and mild pH in washing or cleaning agents, when the pH, which results from the mixture of other components, is not wanted. Acids that are system-compatible and environmentally compatible such as citric acid, acetic acid, tartaric acid, malic acid, glycolic acid, succinic acid, glutaric acid, adipic acid, gluconic acid and mixtures thereof are particularly mentioned in this regard. However, mineral acids, particularly sulfuric acid or bases, particularly ammonium or alkali hydroxides can also serve as pH regulators. Such regulators are comprised in the inventive agents in amounts preferably not above 20 wt. %, particularly from 1.2 wt. % to 17 wt. %.

Other suitable builders are polymeric polycarboxylates, i.e. for example the alkali metal salts of polyacrylic or polymethacrylic acid, for example those with a relative molecular weight of 500 to 70 000 g/mol.

The molecular weights mentioned in this specification for polymeric polycarboxylates are weight-average molecular weights $M_w$ of the particular acid form which, fundamentally, were determined by gel permeation chromatography (GPC), equipped with a UV detector. The measurement was carried out against an external polyacrylic acid standard, which provides realistic molecular weight values by virtue of its structural similarity to the polymers investigated. These values differ distinctly from the molecular weights measured against polystyrene sulfonic acids as standard. The molecular weights measured against polystyrene sulfonic acids are generally higher than the molecular weights mentioned in this specification.

Particularly suitable polymers are polyacrylates, which preferably have a molecular weight of 2000 to 20 000 g/mol. By virtue of their superior solubility, preferred representatives of this group are the short-chain polyacrylates, which have molecular weights of 2000 to 10 000 g/mol and, more particularly, 3000 to 5000 g/mol.

Further suitable copolymeric polycarboxylates are particularly those of acrylic acid with methacrylic acid and of acrylic acid or methacrylic acid with maleic acid. Copolymers of acrylic acid with maleic acid, which comprise 50 to 90 wt. % acrylic acid and 50 to 10 wt. % maleic acid, have proven to be particularly suitable. Their relative molecular weight, based on free acids, generally ranges from 2 to 70 000 g/mol, preferably 20 000 to 50 000 g/mol and especially 30 000 to 40 000 g/mol. The (co)polymeric polycarboxylates can be used either as powders or as aqueous solutions. The (co)polymeric polycarboxylate content of the compositions is preferably from 0.5 to 20% by weight, in particular from 1 to 10% by weight.

In order to improve the water solubility, the polymers can also comprise allylsulfonic acids as monomers, such as for example, allyloxybenzenesulfonic acid and methallylsulfonic acid Other particularly preferred polymers are biodegradable polymers of more than two different monomer units, for example those which contain salts of acrylic acid and maleic acid and vinyl alcohol or vinyl alcohol derivatives as monomers or those which contain salts of acrylic acid and 2-alkylallyl sulfonic acid and sugar derivatives as monomers.

Other preferred copolymers are those, which preferably contain acrolein and acrylic acid/acrylic acid salts or acrolein and vinyl acetate as monomers.

Similarly, other preferred builders are polymeric aminodicarboxylic acids, salts or precursors thereof. Polyaspartic acids or salts and derivatives thereof are particularly preferred.

Other suitable builders are polyacetals, which may be obtained by reaction of dialdehydes with polyol carboxylic acids containing 5 to 7 carbon atoms and at least three hydroxyl groups. Preferred polyacetals are obtained from dialdehydes, such as glyoxal, glutaraldehyde, terephthalaldehyde and mixtures thereof and from polyol carboxylic acids, such as gluconic acid and/or glucoheptonic acid.

Other suitable organic builders are dextrins, for example oligomers or polymers of carbohydrates, which may be obtained by partial hydrolysis of starches. The hydrolysis may be carried out by standard methods, for example acid- or enzyme-catalyzed methods. The end products are preferably hydrolysis products with average molecular weights of 400 to 500 000 g/mol. A polysaccharide with a dextrose equivalent (DE) of 0.5 to 40 and, more particularly, 2 to 30 is preferred, the DE being an accepted measure of the reducing effect of a polysaccharide by comparison with dextrose, which has a DE of 100. Both maltodextrins with a DE of 3 to 20 and dry glucose syrups with a DE of 20 to 37 and also so-called yellow dextrins and white dextrins with relatively high molecular weights of 2000 to 30 000 g/mol may be used.

The oxidized derivatives of such dextrins are their reaction products with oxidizing agents that are capable of oxidizing at least one alcohol function of the saccharide ring to the carboxylic acid function. Particularly preferred organic builders for the inventive agents are oxidized starches or their derivatives from the applications EP 472 042, WO 97/25399 and EP 755 944.

Other suitable co-builders are oxydisuccinates and other derivatives of disuccinates, preferably ethylenediamine disuccinate. Ethylenediamine-N,N'-disuccinate (EDDS) is preferably used in the form of its sodium or magnesium salts. Glycerol disuccinates and glycerol trisuccinates are also preferred in this connection. The quantities used in zeolite-containing and/or silicate-containing formulations are from 3 to 15% by weight.

Other useful organic co-builders are, for example, acetylated hydroxycarboxylic acids and salts thereof which may optionally be present in lactone form and which contain at least 4 carbon atoms, at least one hydroxy group and at most two acid groups.

Another class of substances with co-builder properties are the phosphonates, more particularly hydroxyalkane and aminoalkane phosphonates. Among the hydroxyalkane phosphonates, 1-hydroxyethane-1,1-diphosphonate (HEDP) is a particularly important co-builder. It is preferably used in the form of the sodium salt, the disodium salt showing a neutral reaction and the tetrasodium salt an alkaline reaction (pH 9). Preferred aminoalkane phosphonates are ethylenediamine tetramethylene phosphonate (EDTMP), diethylenetriamine pentamethylenephosphonate (DTPMP) and higher homologs thereof. They are preferably used in the form of the neutrally reacting sodium salts, for example as the hexasodium salt of EDTMP or as the hepta- and octasodium salts of DTPMP. Of the phosphonates, HEDP is preferably used as a builder. In addition, the aminoalkane phosphonates have a pronounced heavy metal binding capacity. Accordingly, it can be of advantage, particularly where the agents also contain bleach, to use aminoalkane phosphonates, more particularly DTPMP, or mixtures of the phosphonates mentioned.

In addition, any compounds capable of forming complexes with alkaline earth metal ions may be used as co-builders.

The inventive agents can optionally comprise builders in quantities of up to 90 wt. % and preferably in amounts up to 75 wt. %. Washing agents according to the invention have builder contents particularly from 5 wt. % to 50 wt. %. In inventive agents for the cleaning of hard surfaces, particularly for automatic cleaning of tableware, the content of builder substances ranges from 5 wt. % to 88 wt. %, wherein advantageously, no water-insoluble builder materials are added to such agents. In a preferred embodiment, the inventive agent, particularly for automatic dishwashers, comprises 20 wt. % to 40 wt. % of water-soluble organic builders, particularly alkali citrate, 5 wt. % to 15 wt. % alkali carbonate and 20 wt. % to 40 wt. % alkali disilicate.

Solvents that can be added to the liquid to gel-like compositions of washing and cleaning agents originate, for example, from the group of mono- or polyhydric alcohols, alkanolamines or glycol ethers, in so far that they are miscible with water in the defined concentrations. Preferably, the solvents are selected from ethanol, n- or i-propanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl-, -ethyl- or -propyl ether, dipropylene glycol methyl-, or -ethyl ether, methoxy-, ethoxy- or butoxy triglycol, 1-butoxyethoxy-2-propanol, 3-methyl-3-methoxybutanol, propylene glycol t-butyl ether as well as mixtures of these solvents.

Solvents can be added to the liquid to gel-like washing and cleaning agents in amounts between 0.1 and 20 wt. %, preferably, however below 15 wt. % and particularly below 10 wt. %.

One or more thickeners or thickener systems can be added to the inventive compositions to adjust the viscosity. These high molecular weight substances, which are also called swelling agents, soak up mostly liquids, thereby swelling up and subsequently transform into viscous, real or colloidal solutions.

Suitable thickeners are inorganic or polymeric organic compounds. The inorganic thickeners include, for example, polysilicic acids, clays such as, montmorillonite, zeolites, silicas and bentonite. The organic thickeners are derived from the group of natural polymers, modified natural polymers and synthetic polymers. Those natural polymers are, for example, agar agar, guar gum, gum arabic, alginates, pectins, polyoses, xanthane gum, karaya gum, locust bean flour, starches and celluloses.

Examples can be cited as carboxymethyl cellulose and other cellulose ethers, hydroxyethyl- and hydroxypropyl cellulose as well as flour ether. Totally synthetic thickeners are polymers such as polyacrylics and polymethacrylics, vinyl polymers, polycarboxylic acids, polyethers, polyimines, polyamides and polyurethanes.

The thickeners can be comprised in amounts up to 5 wt. %, preferably from 0.05 to 2 wt. %, and particularly preferably from 0.1 to 1.5 wt. %, based on the finished preparation.

The washing or cleaning agents according to the invention can optionally comprise other ingredients, such as sequestering agents, electrolytes and further auxiliaries.

The washing agents for textiles may contain derivatives of diaminostilbene disulfonic acid or alkali metal salts thereof as optical brighteners. Suitable optical brighteners are, for example, salts of 4,4'-bis-(2-anilino-4-morpholino-1,3,5-triazinyl-6-amino)stilbene-2,2'-disulfonic acid or compounds of similar structure which contain a diethanolamino group, a methylamino group and anilino group or a 2-methoxyethylamino group instead of the morpholino group. Brighteners of the substituted diphenylstyryl type, for example alkali metal salts of 4,4'-bis-(2-sulfostyryl)diphenyl, 4,4'-bis(4-chloro-3-sulfostyryl)diphenyl or 4-(4-chlorostyryl)-4'-(2-sulfostyryl) diphenyl, may also be present. Mixtures of the brighteners mentioned may also be used.

Graying inhibitors have the function of keeping the dirt detached from the fiber in suspension in the liquor. Suitable for this purpose are water-soluble colloids, usually organic in nature, examples being starch, glue, gelatins, salts of ether carboxylic acids or ether sulfuric acids of the starch or the celluloses, or salts of acidic sulfuric acid esters of cellulose or of starch. Water-soluble polyamides containing acidic groups are also suitable for this purpose. In addition, soluble starch preparations and starch products other than those mentioned above may be used, examples being aldehyde starches. Preference, however, is given to the use of cellulose ethers such as carboxymethyl cellulose (Na salt), methyl cellulose, hydroxyalkyl cellulose, and mixed ethers such as methyl hydroxyethyl cellulose, methyl hydroxypropyl cellulose, methyl carboxymethyl cellulose and mixtures thereof, which can be added, for example in amounts of 0.1 to 5 wt. %, based on the agent.

In order to realize a silver corrosion protection, silver protectors can be added to the inventive cleaning agents for tableware. Benzotriazoles, ferric chloride or $CoSO_4$, for example are known from the prior art. As is known from the European Patent EP 0 736 084 B1, for example, particularly suitable silver protectors for general use with enzymes are salts and/or complexes of manganese, titanium, zirconium, hafnium, vanadium, cobalt or cerium, in which the cited metals exist in the valence states II, III, IV, V or VI. Examples of these types of compounds are $MnSO_4$, $V_2O_5$, $V_2O_4$, $VO_2$, $TiOSO_4$, $K_2TiF_6$, $K_2ZrF_6$, $Co(NO_3)_2$, $Co(NO_3)_3$ and mixtures thereof.

"Soil-release" active substances or "soil repellents" are mainly polymers, which on being used in a washing agent furnish dirt-repellent properties to the wash fibers and/or reinforce the dirt release power of the normal washing agent ingredients. A comparable effect can also be observed by their use in cleaning agents for hard surfaces.

Particularly efficient and long-known soil-release agents are copolyesters with dicarboxylic acid, alkylene glycol and polyalkylene glycol units. Examples of these are copolymers or mixed polymers of polyethylene terephthalate and polyoxyethylene glycol (DT 16 17 141 or DT 22 00 911). German Offenlegungsschrift DT 22 53 063 cites acid compositions, which inter alia comprise a copolymer of a dibasic acid and an alkylene or cycloalkylene polyglycol. Polymers of ethylene terephthalate and polyethylene oxide terephthalate and their use in washing agents are described in the German texts DE 28 57 292 and DE 33 24 258 and the European Patent EP 0 253 567. The European Patent EP 066 944 relates to agents, which contain a copolyester of ethylene glycol, polyethylene glycol, aromatic dicarboxylic acids and sulfonated aromatic dicarboxylic acids in defined molar ratios. Polyesters, end-capped with methyl or ethyl groups, with ethylene and/or propylene terephthalate units and polyethylene oxide terephthalate units and washing agents that comprise such a soil-release polymer are known from EP 0 185 427. The European Patent EP 0 241 984 relates to a polyester, which beside oxyethylene groups and terephthalic acid units also comprises substituted ethylene units as well as glycerol units. Polyesters are known from EP 0 241 985 which contain, beside oxyethylene groups and terephthalic acid units, 1,2-propylene, 1,2-butylene and/or 3-methoxy-1,2-propylene groups as well as glycerol, and are end-capped with $C_1$ to $C_4$ alkyl groups. Polyesters with polypropylene terephthalate units and polyoxyethylene terephthalate units, at least partially end-capped with $C_{1-4}$ alkyl or acyl radicals are known from the European Patent application EP 0 272 033. The European Patent EP 0 274 907 describes soil-release polyesters containing terephthalate end-capped with sulfoethyl groups. According to the European Patent application EP 0 357 280, soil-release polyesters with terephthalate units, alkylene glycol units and poly-$C_{2-4}$ glycol units are manufactured by sulfonation of the unsaturated end groups. The international Patent application WO 95/32232 relates to acid, aromatic dirt-repellant polyesters. Non-polymeric soil-repellants with a plurality of functional units are known from the international Patent application WO 97/31085 for cotton materials: a first unit, which can be cationic, for example, is able to be adsorbed onto the cotton surface by electrostatic attraction, and a second unit, which is designed to be hydrophobic, is responsible for the retention of the active agent at the water/cotton interface.

Color transfer inhibitors that can be used in inventive washing agents for textiles particularly include polyvinyl pyrrolidones, polyvinyl imidazoles, polymeric N-oxides such as polyvinyl pyridine-N-oxide and copolymers of vinyl pyrrolidone with vinyl imidazole.

On using the agents in automatic cleaning processes, it can be advantageous to add foam inhibitors. Suitable foam inhibitors include for example, soaps of natural or synthetic origin, which have a high content of $C_{18}$-$C_{24}$ fatty acids. Suitable non-surface-active types of foam inhibitors are, for example, organopolysiloxanes and mixtures thereof with microfine, optionally silanised silica and also paraffins, waxes, microcrystalline waxes and mixtures thereof with silanised silica or bis-stearyl ethylenediamide. Mixtures of various foam inhibitors, for example mixtures of silicones, paraffins or waxes, are also used with advantage. Preferably, the foam inhibitors, particularly silicone and/or paraffin-containing foam inhibitors are loaded onto a granular, water-soluble or dispersible carrier material. Especially in this case, mixtures of paraffins and bis stearylethylene diamides are preferred.

Furthermore, an inventive cleaning agent for hard surfaces can comprise ingredients having an abrasive action, particularly from the group including quartz powder, wood flour, plastic powder, chalk and glass microspheres as well as mixtures thereof. The cleaning agents according to the invention comprise preferably not more than 20 wt. %, particularly from 5 wt. % to 15 wt. % of abrasive materials.

Colorants and fragrances may be added to the washing or cleaning agents in order to improve the aesthetic impression created by the products and to provide the consumer not only with the required performance but also with a visually and sensorially "typical and unmistakable" product. Suitable perfume oils or fragrances include individual perfume compounds, for example synthetic products of the ester, ether, aldehyde, ketone, alcohol and hydrocarbon type. Perfume compounds of the ester type are, for example, benzyl acetate, phenoxyethyl isobutyrate, p-tert.-butylcyclohexyl acetate, linalyl acetate, dimethylbenzyl carbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals containing 8 to 18 carbon atoms, citral, citronellal, citronellyloxyacetaldehyde, cyclamen aldehyde, hydroxycitronellal, lilial and bourgeonal; the ketones include, for example, the ionones, α-isomethyl ionone and methyl cedryl ketone; the alcohols include anethol, citronellol, eugenol, geraniol, linalool, phenylethyl alcohol and terpineol and the hydrocarbons include, above all, the terpenes, such as limonene and pinene. However, mixtures of various perfumes, which together produce an attractive perfume note, are preferably used. Perfume oils such as these may also contain natural perfume mixtures obtainable from vegetal sources, for example pine, citrus, jasmine, patchouli, rose or ylang-ylang oil. Also suitable are muscatel oil, oil of sage, chamomile oil, clove oil, melissa oil, mint oil, cinnamon leaf oil, lime blossom oil, juniper berry oil, vetivert oil, olibanum oil, galbanum oil and ladanum oil and orange blossom oil, neroli oil, orange peel oil and sandalwood oil. Normally the content of dyes lies below 0.01 wt. %, while fragrances can make up to 2 wt. % of the total formulation of the washing and cleaning agents.

The fragrances may be directly incorporated in the washing and cleaning agents, although it can also be of advantage to apply the fragrances on carriers, which reinforce the adsorption of the perfume on the washing and thereby ensuring a long-lasting fragrance on the textiles by decreasing the release of the fragrance, especially for treated textiles. Suitable carrier materials have proved to be for example, cyclodextrins, the cyclodextrin/perfume complexes optionally being coated with other auxiliaries. A further preferred carrier for fragrances is the already described zeolite X, which can also take up fragrances instead of, or in mixtures with surfactants. Accordingly, preferred washing and cleaning agents comprise the described zeolite X and fragrances, which are preferably at least partially absorbed on the zeolite.

Preferred colorants, which are not difficult for the expert to choose, have high storage stability, are not affected by the other ingredients of the detergents or by light and do not have any pronounced substantivity for the textile fibers being treated, so as not to color them.

To control microorganisms, the washing or cleaning agents may contain antimicrobial agents. Depending on the antimicrobial spectrum and the action mechanism, antimicrobial agents are classified as bacteriostatic agents and bactericides, fungistatic agents and fungicides, etc. Important representatives of these groups are, for example, benzalkonium chlorides, alkylaryl sulfonates, halophenols and phenol mercuric acetate. In the present context of the inventive teaching, the expressions "antimicrobial activity" and "antimicrobial agent" have the usual technical meanings as defined, for example, by K. H. Wallhausser in "Praxis der Sterilisation, Desinfektion—Konservierung Keimidentifizierung—Betriebshygiene" (5th Edition, Stuttgart/New York: Thieme, 1995), any of the substances with antimicrobial activity described therein being usable. Suitable antimicrobial agents are preferably selected from the groups of alcohols, amines, aldehydes, antimicrobial acids and salts thereof, carboxylic acid esters, acid amides, phenols, phenol derivatives, diphenyls, diphenylalkanes, urea derivatives, oxygen and nitrogen acetals and formals, benzamidines, isothiazolines, phthalimide derivatives, pyridine derivatives, antimicrobial surface-active compounds, guanidines, antimicrobial amphoteric compounds, quinolines, 1,2-dibromo-2,4-dicyanobutane, iodo-2-propyl butyl carbamate, iodine, iodophores, peroxy compounds, halogen compounds and mixtures of the above.

Consequently, the antimicrobial active substances can be chosen among ethanol, n-propanol, i-propanol, 1,3-butanediol, phenoxyethanol, 1,2-propylenelycol, glycerol, undecylenic acid, benzoic acid, salicylic acid, dihydracetic acid, o-phenylphenol, N-methylmorpholine-acetonitrile (MMA), 2-benzyl-4-chlorophenol, 2,2'-methylene-bis-(6-bromo-4-chlorophenol), 4,4'-dichloro-2'-hydroxydiphenyl ether (dichlosan), 2,4,4'-trichloro-2'-hydroxydiphenyl ether (trichlosan), chlorhexidine, N-(4-chlorophenyl)-N-(3,4-dichlorophenyl)-urea, N,N'-(1,10-decanediyldi-1-pyridinyl-4-ylidene)-bis-(1-octamine) dihydrochloride, N,N'-bis-(4-chlorophenyl)-3,12-diimino-2,4,11,13-tetraaza-tetradecanediimideamide, glucoprotamines, surface-active antimicrobial quaternary compounds, guanidines, including the bi- and polyguanidines, such as for example 1,6-bis(2-ethylhexylbiguanidohexane) dihydrochloride, 1,6-di-($N_1$, $N_1$'-phenyldiguanido-$N_5$,$N_5$')hexane tetrahydrochloride, 1,6-di-($N_1$,$N_1$'-phenyl-$N_1$,$N_1$'-methyldiguanido-$N_5$,$N_5$')hexane dihydrochloride, 1,6-di-($N_1$,$N_1$'-o-chlorophenyldiguanido-$N_5$,$N_5$')hexane dihydrochloride, 1,6-di-($N_1$,$N_1$'-2,6-dichlorophenyldiguanido-$N_5$,$N_5$)hexane dihydrochloride, 1,6-di-[$N_1$,$N_1$'-β-(p-methoxyphenyl) diguanido-$N_5$,$N_5$']hexane dihydrochloride, 1,6-di-($N_1$,$N_1$'-α-methyl-α-phenyl-diguanido-$N_5$,$N_5$')hexane dihydrochloride, 1,6-di-($N_1$,$N_1$'-p-nitrophenyldiguanido-$N_5$,$N_5$')hexane dihydrochloride, ω:ω-di-($N_1$,$N_1$'-phenyldiguanido-$N_5$,$N_5$')di-n-propyl ether dihydrochloride, ω:ω-di-($N_1$,$N_1$'-p-chlorophenyldiguanido-$N_5$,$N_5$')di-n-propyl ether tetrahydrochloride, 1,6-di-($N_1$,$N_1$'-2,4-dichlorophenyldiguanido-$N_5$,$N_5$')hexane tetrahydrochloride, 1,6-di-($N_1$,$N_1$'-p-methylphenyldiguanido-$N_5$,$N_5$') hexane dihydrochloride, 1,6-di-($N_1$,$N_1$'-2,4,5-trichlorophenyldiguanido-$N_5$,$N_5$)hexane tetrahydrochloride, 1,6-di-[$N_1$,$N_1$'-α-(p-chlorophenyl)ethyldiguanido-$N_5$,$N_5$'] hexane dihydrochloride, ω:ω-di-($N_1$,$N_1$'-p-chlorophenyl-diguanido-$N_5$,$N_5$')$_m$-xylene dihydrochloride, 1,12-di-($N_1$, $N_1$'-p-chlorophenyldiguanido-$N_5$,$N_5$')dodecane dihydrochloride, 1,10-di-($N_1$,$N_1$'-phenyldiguanido-$N_5$,$N_5$') decane tetrahydrochloride, 1,12-di-($N_1$,$N_1$'-phenyl-diguanido-$N_5$,$N_5$')dodecane tetrahydrochloride, 1,6-di-($N_1$, $N_1$'-o-chlorophenyldiguanido-$N_5$,$N_5$')hexane dihydrochloride, 1,6-di-($N_1$,$N_1$'-o-chlorophenyldiguanido-$N_5$,$N_5$')hexane tetrahydrochloride, ethylene-bis-(1-tolylphenylbiguanide), ethylene-bis-(p-tolylphenylbiguanide), ethylene-bis-(3,5-dimethylphenylbiguanide), ethylene-bis-(p-tert-amylphenylbiguanide), ethylene-bis-(nonylphenylbiguanide), ethylene-bis-(phenylbiguanide), ethylene-bis-(N-butylphenylbiguanide), ethylene-bis-(2,5-diethoxyphenylbiguanide), ethylene-bis-(2,4-dimethylphenylbiguanide), ethylene-bis-(o-diphenylbiguanide), ethylene-bis-(mixed amylnaphthylbiguanide), N-butylethylene-bis-(phenylbiguanide), trimethylene bis(o-tolylbiguanide), N-butyltrimethylene-bis-(phenylbiguanide) and the corresponding salts like acetates, gluconates, hydrochlorides, hydrobromides, citrates, bisulfites, fluorides, polymaleates, N-coco alkyl sarcinosates, phosphites, hypophosphites, perfluorooctanoates, silicates, sorbates, salicylates, maleates, tartrates, fumarates, ethylenediaminetetraacetates, iminodiacetates, cinnamates, thiocyanates, arginates, pyromellitates, tetracarboxybutyrates, benzoates, glutarates, monofluorophosphates, perfluoropropionates as well as any mixtures thereof. Furthermore, halogenated xylene- and cresol derivatives are suitable, such as p-chloro-meta-cresol, p-chloro-meta-xylene, as well as natural antimicrobial active agents of plant origin (e.g. from spices or aromatics), animal as well as microbial origin. Preferred antimicrobial agents are antimicrobial surface-active quaternary compounds, a natural antimicrobial agent of vegetal origin and/or a natural antimicrobial agent of animal origin and, most preferably, at least one natural antimicrobial agent of vegetal origin from the group comprising caffeine, theobromine and theophylline and essential oils, such as eugenol, thymol and geraniol, and/or at least one natural antimicrobial agent of animal origin from the group comprising enzymes, such as protein from milk, lysozyme and lactoperoxidase and/or at least one antimicrobial surface-acfive quaternary compound containing an ammonium, sulfonium, phosphonium, iodonium or arsonium group, peroxy compounds and chlorine compounds. Substances of microbial origin, so-called bacteriozines, may also be used.

The quaternary ammonium compounds (QUATS) suitable as antimicrobial agents have the general formula $(R^1)(R^2)(R^3)(R^4)N^+X^-$, in which $R^1$ to $R^4$ may be the same or different and represent $C_{1-22}$ alkyl groups, $C_{7-28}$ aralkyl groups or heterocyclic groups, two or—in the case of an aromatic compound, such as pyridine—even three groups together with the nitrogen atom forming the heterocycle, for example a pyridinium or imidazolinium compound, and $X^-$ represents halide ions, sulfate ions, hydroxide ions or similar anions. In the interests of optimal antimicrobial activity, at least one of the substituents preferably has a chain length of 8 to 18 and, more preferably, 12 to 16 carbon atoms.

QUATS can be obtained by reacting tertiary amines with alkylating agents such as, for example, methyl chloride, benzyl chloride, dimethyl sulfate, dodecyl bromide and also ethylene oxide. The alkylation of tertiary amines having one long alkyl chain and two methyl groups is particularly easy. The quaternization of tertiary amines containing two long chains and one methyl group can also be carried out under mild conditions using methyl chloride. Amines containing three long alkyl chains or hydroxy-substituted alkyl chains lack reactivity and are preferably quaternized with dimethyl sulfate.

Suitable QUATS are, for example, benzalkonium chloride (N-alkyl-N,N-dimethylbenzyl ammonium chloride, CAS No. 8001-54-5), benzalkon B (m,p-dichlorobenzyl dimethyl-$C_{12}$-alkyl ammonium chloride, CAS No. 58390-78-6), benzoxonium chloride (benzyldodecyl-bis-(2-hydroxyethyl) ammonium chloride), cetrimonium bromide (N-hexadecyl-N,N-trimethyl ammonium bromide, CAS No. 57-09-0), benzetonium chloride (N,N-di-methyl-N-[2-[2-[p-(1,1,3,3-tetramethylbutyl)-phenoxy]-ethoxy]-ethyl]-benzyl ammonium chloride, CAS No. 121-54-0), dialkyl dimethyl ammonium chlorides, such as di-n-decyldimethyl ammonium chloride (CAS No. 7173-51-5-5), didecyldimethyl ammonium bromide (CAS No. 2390-68-3), dioctyl dimethyl ammonium chloride, 1-cetylpyridinium chloride (CAS No. 123-03-5) and thiazoline iodide (CAS No. 1576448-1) and mixtures thereof. Particularly preferred QUATS are the benzalkonium chlorides containing $C_{8-18}$ alkyl groups, more particularly $C_{12}$-14 alkyl benzyl dimethyl ammonium chloride.

Benzalkonium halides and/or substituted benzalkonium halides are commercially obtainable, for example, as Barquat® from Lonza, Marquato® from Mason, Variquat® from Witco/Sherex and Hyamine® from Lonza and as Bardac® from Lonza. Other commercially obtainable antimicrobial agents are N-(3-chloroallyl)-hexaminium chloride, such as Dowicide® and Dowicil® from Dow, benzethonium chloride, such as Hyamine® 1622 from Rohm & Haas, methyl benzethonium chloride, such as Hyamine® 10× from Rohm & Haas, cetyl pyridinium chloride, such as cepacolchloride from Merrell Labs.

The antimicrobial agents are used in quantifies of 0.0001% by weight to 1% by weight, preferably 0.001% by weight to 0.8% by weight, particularly preferably 0.005% by weight to 0.3% by weight and most preferably 0.01 to 0.2% by weight.

The compositions may comprise UV absorbers, which attach to the treated textiles and improve the light stability of the fibers and/or the light stability of the various ingredients of the formulation. UV-absorbers are understood to mean organic compounds, which are able to absorb UV radiation and emit the resulting energy in the form of longer wavelength radiation, for example as heat.

Compounds, which possess these desired properties, are for example, the efficient radiationless deactivating derivatives of benzophenone having substituents in position(s) 2 and/or 4. Also suitable are substituted benzotriazoles, acrylates, which are phenyl-substituted in position 3 (cinnamic acid derivatives optionally with cyano groups in position 2), salicylates, organic Ni complexes, as well as natural substances such as umbelliferone and the endogenous urocanic acid. The biphenyl and above all the stilbene derivatives such as, for example those described in EP 0728749 A and commercially available as Tinosorb® FD or Tinosorb® FR from Ciba, are of particular importance. As UV-B absorbers can be cited: 3-benzylidenecamphor or 3-benzylidenenorcamphor and its derivatives, for example 3-(4-methylbenzylidene) camphor, as described in the EP 0693471 B 1; 4-aminobenzoic acid derivatives, preferably 4-(dimethylamino)benzoic acid, 2-ethylhexyl ester, 4-(dimethylamino)benzoic acid, 2-octyl ester and 4-(dimethylamino)benzoic acid, amyl ester; esters of cinnamic acid, preferably 4-methoxycinnamic acid, 2-ethylhexyl ester, 4-methoxycinnamic acid, propyl ester, 4-methoxycinnamic acid, isoamyl ester, 2-cyano-3,3-phenylcinnamic acid, 2-ethylhexyl ester (octocrylene); esters of salicylic acid, preferably salicylic acid, 2-ethylhexyl ester, salicylic acid, 4-isopropylbenzyl ester, salicylic acid, homomenthyl ester; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably 4-methoxybenzmalonic acid, di-2-ethylhexyl ester; triazine derivatives, such as, for example 2,4,6-trianilino-(p-carbo-2'-ethyl-1'-hexyloxy)-1,3,5-triazine and octyl triazone, as described in EP 0818450 A1 or dioctyl butamidotriazone (Uvasorb® HEB); propane-1,3-dione, such as for example 1-(4-tert.-butylphenyl)-3-(4'-methoxyphenyl)propane-1,3-dione; ketotricyclo(5.2.1.0) decane derivatives, as described in EP 0694521 B 1. Further suitable are 2-phenylbenzimidazole-5-sulfonic acid and its alkali-, earth alkali-, ammonium-, alkylammonium-, alkanolammonium- and glucammonium salts; sulfonic acid derivatives of benzophenones, preferably 2-hydroxy4-methoxybenzophenone-5-sulfonic acid and its salts; sulfonic acid derivatives of 3-benzylidenecamphor, as for example 4-(2-oxo-3-bornylidenemethyl)benzene sulfonic acid and 2-methyl-5-(2-oxo-3-bornylidene) sulfonic acid and its salts. Typical UV-A filters particularly include derivatives of benzoylmethane, such as, for example 1-(4'-tert.-butylphenyl)-3-(4'-methoxyphenyl)propane-1,3-dione, 4-tert.-butyl4'-methoxydibenzoylmethane (Parsol 1789), 1-phenyl-3-(4'-isopropylphenyl)-propane-1,3-dione as well as enamine compounds, as described in the DE 19712033 A1 (BASF). Naturally, the UV-A and UV-B filters can also be added as mixtures. Beside the cited soluble materials, insoluble, light protective pigments, namely finely dispersed, preferably, nano metal oxides or salts can also be considered for this task. Exemplary suitable metal oxides are particularly zinc oxide and titanium oxide and also oxides of iron, zirconium, silicon, manganese, aluminum and cerium as well as their mixtures. Silicates (talc), barium sulfate or zinc stearate can be added as salts. The oxides and salts are already used in the form of pigments for skin care and skin protecting emulsions and decorative cosmetics. Here, the particles should have a mean diameter of less than 100 nm, preferably between 5 and 50 nm and especially between 15 and 30 nm. They can be spherical, however elliptical or other shaped particles can also be used. The pigments can also be surface treated, i.e. hydrophilized or hydrophobized. Typical examples are coated titanium dioxides, such as, for example Titandioxid Z 805 (Degussa) or Eusolex® T2000 (Merck); hydrophobic coating agents preferably include trialkoxy octylsilanes or silicones. Micronized zinc oxide is preferably used. Further suitable UV light protection filters may be found in the review by P. Finkel in SoFW-Journal, volume 122 (1996), p. 543.

The UV absorbers are normally used in amounts of 0.01 wt. % to 5 wt. %, preferably from 0.03 wt. % to 1 wt. %.

To increase their washing or cleaning power, agents according to the invention can comprise, in addition to the inventive enzymes, additional enzymes, in principle any enzyme established for these purposes in the prior art being useable. These particularly include proteases, amylases, lipases, hemicellulases, cellulases or oxidoreductases as well as preferably their mixtures. In principle, these enzymes are of natural origin; improved variants based on the natural molecules are available for use in washing and cleaning agents and accordingly they are preferred. The agents according to the invention preferably comprise enzymes in total quantities of $1 \times 10^{-6}$ to 5 weight percent based on active protein. The protein concentration can be determined using known methods, for example the BCA Process (bicinchoninic acid; 2'-bichinolyl-4,4'-dicarboxylic acid) or the biuret process (A. G. Gornall, C. S. Bardawill and M. M. David, J. Biol. Chem., 177 (1948), p. 751-766).

Preferred proteases are those of the subtilisin type. Examples of these are subtilisins BPN' and Carlsberg, the protease PB92, the subtilisins 147 and 309, the alkaline protease from *Bacillus lentus*, subtilisin DY and those enzymes of the subtilases no longer however classified in the stricter sense as subtilisins thermitase, proteinase K and the proteases TW3 und TW7. Subtilisin Carlsberg in further developed form is available under the trade name Alcalase® from Novozymes A/S, Bagsværd, Denmark. Subtilisins 147 and 309 are commercialized under the trade names Esperase® and Savinase® by the Novozymes company. Variants derived from the protease from *Bacillus lentus* DSM 5483 (WO 91/02792 A1) are called BLAP®, described particularly in WO 92/21760 A1, WO 95/23221 A1, WO 02/088340 A2 and WO 03/038082 A2. Further useable proteases from various Bacillus sp. and B. gibsonii emerge from the patent applications WO 03/054185 A1, WO 03/056017 A2, WO 03/055974 A2 and WO 03/054184 A1.

Further useable proteases are, for example, those enzymes available with the trade names Durazym®, Relase®, Everlase®, Nafizym, Natalase®, Kannase® and Ovozymes® from the Novozymes Company, those under the trade names Purafect®, Purafect®OxP and Properase® from Genencor, that under the trade name Protosol® from Advanced Biochemicals Ltd., Thane, India, that under the trade name Wuxi® from Wuxi Snyder Bioproducts Ltd., China, those under the trade names Proleather® and Protease P® from Amano Pharmaceuticals Ltd., Nagoya, Japan, and that under the designation Proteinase K-16 from Kao Corp., Tokyo, Japan.

Examples of further useable amylases according to the invention are the α-amylases from *Bacillus licheniformis*, from *B. amyloliquefaciens* and from *B. stearothermophilus*, as well as their improved further developments for use in washing and cleaning agents. The enzyme from *B. licheniformis* is available from the Company Novozymes under the name Termamyl® and from the Genencor Company under the name Purastar®ST. Further development products of this α-amylase are available from the Company Novozymes under the trade names Duramyl® and Termamyl®ultra, from the Company Genencor under the name Purastar®OxAm and from the Company Daiwa Seiko Inc., Tokyo, Japan as Keistase®. The α-amylase from *B. amyloliquefaciens* is commercialized by the Company Novozymes under the name BAN®, and derived variants from the α-amylase from *B. stearothermophilus* under the names BSG® and Novamyl®, also from the Company Novozymes.

Moreover, for these purposes, attention should be drawn to the α-amylase from *Bacillus* sp. A 7-7 (DSM 12368) disclosed in the application WO 02/10356 A2 and the cyclodextrin-glucanotransferase (CGTase) from *B. agaradherens* (DSM 9948) described in WO 02/44350 A2. Amylolytic enzymes can also be used, which belong to the sequence space of α-amylases, defined in the application WO 03/002711 A2, and those described in the application WO 03/054177 A2. Similarly, fusion products of the cited molecules are applicable, for example those from the application DE 10138753 A1.

Moreover, further developments of a-amylase from *Aspergillus niger* und *A. oryzae* available from the Company Novozymes under the trade name Fungamyl® are suitable. A further suitable commercial product is, for example Amylase-LT®.

The agents according to the invention can comprise lipases or cutinases, particularly due to their triglyceride cleaving activities, but also in order to produce in situ peracids from suitable preliminary steps. These include the available or further developed lipases originating from *Humicola lanuginosa* (*Thermomyces lanuginosus*), particularly those with the amino acid substitution D96L. They are commercialized, for example by the Novozymes Company under the trade names Lipolase®, Lipolase®Ultra, LipoPrime®, Lipozyme® and Lipex®. Moreover, suitable cutinases, for example are those that were originally isolated from *Fusarium solani pisi* and *Humicola insolens*. Likewise useable lipases are available from the Amano Company under the designations Lipase CE®, Lipase P®, Lipase B®, and Lipase CES®, Lipase AKG®, *Bacillis* sp. Lipase®, Lipase AP®, Lipase M-AP® and Lipase AML®. Suitable lipases or cutinases whose starting enzymes were originally isolated from *Pseudomonas mendocina* und *Fusarium* solanii are for example available from Genencor Company. Further important commercial products that may be mentioned are the commercial preparations M1 Lipase® und Lipomax® originally from Gist-Brocades Company, and the commercial enzymes from the Meito Sangyo KK Company, Japan under the names Lipase MY-30®, Lipase OF® and Lipase PL® as well as the product Lumafast® from Genencor Company.

Agents according to the invention, particularly when they are destined for treating textiles, can comprise cellulases, according to their purpose, as pure enzymes, as enzyme preparations, or in the form of mixtures, in which the individual components advantageously complement their various performances. Among these aspects of performance are particular contributions to primary washing performance, to secondary washing performance of the product, (anti-redeposition activity or inhibition of graying) and softening or brightening (effect on the textile), through to practicing a "stone washed" effect.

A usable, fungal endoglucanase(EG)-rich cellulase preparation, or its further developments are offered by the Novozymes Company under the trade name Celluzyme®. The products Endolase® and Carezyme® based on the 50 KD-EG, respectively 43 kD-EG from *H. insolens* DSM 1800 are also obtainable from Novozymes Company. The latter is based on the application WO 96/29397 A1. Cellulase variants with improved performance emerge, for example, from the application WO 98/12307 A1. Similarly, the cellulases disclosed in application WO 97/14804 A1 can be used; for example 20 kD-EG cellulase from Melanocarpus, obtainable from AB Enzymes Company, Finland under the trade names Ecostone® and Biotouch®. Further commercial products from the AB Enzymes Company are Econase® and Ecopulp®. Further suitable cellulases from *Bacillus* sp. CBS 670.93 and CBS 669.93 are disclosed in WO 96/34092 A2, the CBS 670.93 from *Bacillus* sp. being obtainable from the Genencor Company under the trade name Puradax®. Additional commercial products from the Genencor Company are "Genencor detergent cellulase L" and Indiage®Neutra.

The agents according to the invention can comprise additional enzymes especially for removing specific problem stains and which are summarized under the term hemicellulases. These include, for example mannanases, xanthanlyases, pectinlyases (=pectinases), pectinesterases, pectatlyases, xyloglucanases (=xylanases), pullulanases und β-glucanases. Suitable mannanases, for example are available under the names Gamanase® and Pektinex AR® from Novozymes Company, under the names Rohapec® B1L from AB Enzymes and under the names Pyrolase® from Diversa Corp., San Diego, Calif., USA. A suitable β-Glucanase from a *B. alcalophilus* emerges from the application WO 99/06573 A1, for example. β-Glucanase extracted from *B. subtilis* is available under the name Cereflo® from Novozymes Company.

To increase the bleaching action, the washing or cleaning agents according to the invention can comprise oxidoreductases, for example oxidases, oxygenases, katalases, peroxidases, like halo-, chloro-, bromo-, lignin-, glucose- or manganese-peroxidases, dioxygenases or laccases (phenoloxidases, polyphenoloxidases). Suitable commercial products are Denilite® 1 and 2 from the Novozymes Company. Advantageously, additional, preferably organic, particularly preferably aromatic compounds are added that interact with the enzymes to enhance the activity of the relative oxidoreductases or to facilitate the electron flow (mediators) between the oxidizing enzymes and the stains over strongly different redox potentials.

The enzymes used in the inventive agents either stem originally from microorganisms, such as the species *Bacillus*,

*Streptomyces, Humicola*, or *Pseudomonas*, and/or are produced according to known biotechnological processes using suitable microorganisms such as by transgenic expression hosts of the species *Bacillus* or filamentous fungi.

Purification of the relevant enzymes follows conveniently using established processes such as precipitation, sedimentation, concentration, filtration of the liquid phases, microfiltration, ultrafiltration, mixing with chemicals, deodorization or suitable combinations of these steps.

The enzymes can be added to the inventive agents in each established form according to the prior art. Included here, for example, are solid preparations obtained by granulation, extrusion or lyophilization, or particularly for liquid agents or agents in the form of gels, enzyme solutions, advantageously highly concentrated, of low moisture content and/or mixed with stabilizers.

As an alternative application form, the enzymes can also be encapsulated, for example by spray drying or extrusion of the enzyme solution together with a preferably natural polymer or in the form of capsules, for example those in which the enzyme is embedded in a solidified gel, or in those of the core-shell type, in which an enzyme-containing core is covered with a water-, air- and/or chemical-impervious protective layer. Further active principles, for example stabilizers, emulsifiers, pigments, bleaches or colorants can be applied in additional layers. Such capsules are made using known methods, for example by vibratory granulation or roll compaction or by fluid bed processes. Advantageously, these types of granulates, for example with an applied polymeric film former are dust-free and as a result of the coating are storage stable.

In addition, it is possible to formulate two or more enzymes together, so that a single granulate exhibits a plurality of enzymatic activities.

The protein concentration on the comprised enzymes, particularly on the comprised choline oxidases can be determined using known methods, for example the BCA Process (bicinchoninic acid; 2,2'-bichinolyl4,4'-dicarboxylic acid) or the biuret process (A. G. Gornall, C. S. Bardawill and M. M. David, *J. Biol. Chem.*, 177 (1948), p. 751-766).

A protein and/or enzyme in an inventive agent can be protected, particularly in storage, against deterioration such as, for example inactivation, denaturation or decomposition, for example through physical influences, oxidation or proteolytic cleavage. An inhibition of the proteolysis is particularly preferred during microbial preparation of proteins and/or enzymes, particularly when the compositions also contain proteases. Preferred compositions according to the invention comprise stabilizers for this purpose.

One group of stabilizers are reversible protease inhibitors. For this, benzamidine hydrochloride, borax, boric acids, boronic acids or their salts or esters are frequently used, above all derivatives with aromatic groups, for example ortho, meta or para substituted phenyl boronic acids, or their salts or esters. Peptide aldehydes, i.e. oligopeptides with a reduced C-terminus, particularly those from 2 to 50 monomers are also used for this purpose. Ovomucoid and leupeptin, among others, belong to the peptidic reversible protease inhibitors. Specific, reversible peptide inhibitors for the protease subtilisin and fusion proteins from proteases and specific peptide inhibitors are also suitable.

Further enzyme stabilizers are amino alcohols like mono-, di-, triethanol- and -propanolamine and their mixtures, aliphatic carboxylic acids up to $C_{12}$, such as, for example succinic acid, other dicarboxylic acids or salts of the cited acids. End-capped fatty acid amide alkoxylates are also suitable for this purpose. Certain organic acids used as builders can, as disclosed in WO 97/18287 additionally stabilize an included enzyme.

Lower aliphatic alcohols, but above all polyols such as, for example glycerol, ethylene glycol, propylene glycol or sorbitol are further frequently used enzyme stabilizers. Di-glycerol phosphate also protects against denaturation by physical influences. Similarly, calcium and/or magnesium salts are used, such as, for example calcium acetate or calcium formate.

Polyamide oligomers or polymeric compounds like lignin, water-soluble vinyl copolymers or cellulose ethers, acrylic polymers and/or polyamides stabilize enzyme preparations against physical influences or pH variations. Polymers containing polyamine-N-oxide act simultaneously as enzyme stabilizers and color transfer inhibitors. Other polymeric stabilizers are linear $C_8$-$C_{18}$ polyoxyalkylenes. Alkyl polyglycosides can also stabilize the enzymatic components of the inventive agents and are additionally capable of advantageously increasing their performance. Crosslinked nitrogen-containing compounds advantageously perform a dual function as soil release agents and as enzyme stabilizers. A hydrophobic, nonionic polymer stabilizes in particular an optionally present cellulase.

Reducing agents and antioxidants increase the stability of enzymes against oxidative decomposition; sulfur-containing reducing agents are commonly used here. Other examples are sodium sulfite and reducing sugars.

The use of combinations of stabilizers is particularly preferred, for example of polyols, boric acid and/or borax, the combination of boric acid or borate, reducing salts and succinic acid or other dicarboxylic acids or the combination of boric acid or borate with polyols or polyamino compounds and with reducing salts. The effect of peptide-aldehyde stabilizers is conveniently increased by the combination with boric acid and/or boric acid derivatives and polyols and still more by the additional effect of divalent cations, such as, for example, calcium ions.

In a preferred embodiment, inventive agents are characterized in that they consist of more than one phase in order to liberate the comprised active principles separately from one another at different times or from different places, for example. This can concern phases in different aggregates, however it particularly concerns phases in the same aggregates.

Inventive agents, which are composed of more than one solid component, can be easily manufactured by mixing together the various solid components in bulk form, particularly powders, granules or extrudates with various ingredients and/or different release behavior. The manufacture of inventive solid agents with one or more phases can be made by known methods, for example by spray drying or granulation, wherein the enzymes and possible further heat-sensitive ingredients, such as, for example bleaches are optionally added separately. For manufacturing inventive agents with an increased bulk density, particularly in the range of 650 g/l to 950 g/l, a preferred process is one with an extrusion step, known from the European Patent EP 0 486 592. A further preferred manufacturing using a granulation process is described in the European Patent EP 0 642 576.

For solid agents, proteins can be used, for example, in dried, granulated, encapsulated or encapsulated and additionally dried form. They can be added separately, i.e. as one phase, or together with other ingredients in the same phase, with or without compaction. If microencapsulated, solid enzymes are used, then the water can be removed from the aqueous solutions resulting from the process by means of processes known from the prior art, such as spray-drying, centrifugation or by transdissolution. The particles obtained in this manner normally have a particle size between 50 and 200 μm.

The encapsulated form also serves, as previously discussed, to protect the enzymes from other ingredients such as bleaches, or to enable a controlled release. These capsules are differentiated by size as millicapsules, microcapsules and nanocapsules; microcapsules being particularly preferred for enzymes. Such capsules are disclosed, for example, in the Patent applications WO 97/24177 and DE 199 18 267. Another possible encapsulation method consists in the encapsulation of the enzymes, suitable for washing or cleaning agents, in starch or in starch derivatives, starting from a mixture of the enzyme solutions with a solution or suspension of starch or a starch derivative. Such an encapsulation process is described in the German application DE 199 56 382.

At least two solid phases can also be combined with each other. Thus, it is possible to prepare a solid agent according to the invention, by compression or compaction into tablets. Such tablets can be monophase or multiphase tablets. Consequently, this presentation form also offers the possibility of displaying a solid inventive agent having two solid phases. For manufacturing the inventive agents in tablet form, which can be monophasic or multiphasic, single colored or multicolored and/or consisting of one or several layers, all the ingredients—optionally for each layer—are preferably mixed together in a mixer and the mixture is compressed using conventional tablet presses, e.g. exocentric presses or rotating presses with compression forces in the range of about 50 to 100 kN/cm², preferably 60 to 70 kN/cm². Particularly for the case of multilayer tablets, it can be advantageous to precompress at least one layer. This is preferably carried out using compression forces between 5 and 20 kN/cm², particularly 10 to 15 kN/cm². Tablets prepared in this way preferably have a weight of 10 g to 50 g, particularly 15 g to 40 g. The tablets may be any shape—round, oval or angled—intermediate shapes also being possible.

It is particularly advantageous for multiphase agents, that at least one of the phases comprises an amylase-sensitive material, especially starch, or is at least partially encapsulated or coated with this. In this way this phase is mechanically stabilized and/or protected against external influences and simultaneously attacked by an active amylase present in the wash liquor, such that the release of the ingredients is facilitated.

Similarly, preferred agents according to the invention are characterized in that they are all in liquid, gel or paste form. The proteins, preferably a protein according to the invention, are added to such agents and preferably result from a state of the art protein extraction and preparation in concentrated aqueous or non-aqueous solution, for example in liquid form, such as solution, suspension or emulsion, but also in gel form or encapsulated or as dried powder. This type of inventive washing or cleaning agent in the form of solutions in standard solvents are generally prepared by a simple mixing of the ingredients, which can be added in the substance or as a solution into an automatic mixer.

An embodiment of the present invention is such a liquid, gel or paste agent, to which has been added an encapsulated protein essential for the invention and/or one of the other comprised proteins and/or one of the other comprised ingredients in the form of microcapsules. Among these, those encapsulated with amylase-sensitive materials are particularly preferred. The use of a combination of amylase-sensitive materials and an amylolytic enzyme in a washing or cleaning agent can demonstrate synergistic effects in such a way that the starch degrading enzyme supports the breakdown of the microcapsule and thereby controls the release process of the encapsulated ingredients with the result that the release does not happen during storage and/or not at the beginning of the cleaning process, but rather at a defined time. By this mechanism, complex washing and cleaning agent systems can be based on the most varied ingredients and the most varied capsule types, which represent the particularly preferred embodiments of the present invention.

A comparable effect is given when the ingredients of the washing and cleaning agent are distributed in at least two different phases, for example two or more solid associated phases of a tableted washing or cleaning agent, or different granules in the same powdery agent. Two-phase or multiphase cleaners are state of the art for use in both automatic dishwashers as well as washing agents. The activity of an amylolytic enzyme in an earlier activated phase is a prerequisite for the activation of a later phase, when this is surrounded by an amylase-sensitive shell or coating, or the amylase-sensitive material represents an integral part of the solid phase, whose partial or total hydrolysis disintegrates the relevant phase.

The ingredients of washing and cleaning agents are capable of suitably supporting each other's performance. Thus, it is known from the application WO 98/45396, that polymers, which can be added as cobuilders, such as, for example alkyl polyglycosides, can simultaneously stabilize and augment the activity and stability of included enzymes. Accordingly, it is preferred when a Carlsberg variant according to the invention is modified by one of the customary ingredients mentioned above, it is especially stabilized and/or its contribution to the performance of the washing or cleaning agent is increased.

Processes for cleaning textiles or hard surfaces constitute a further subject of the invention and are characterized in that an above-described inventive perhydrolase variant is active in at least one of the process steps.

In this embodiment, the invention is realized in that the improved inventive enzymatic properties are utilized in principal in terms of an improvement in each cleaning process. Each cleaning process is enhanced in the relevant activity when it is present in at least one process step. Such processes are realized in machines such as standard household automatic dishwashers or household washing machines. Preferred processes are correspondingly preferred according to the abovementioned details. Further preferred processes are those wherein the perhydrolase variants are added in an above-described agent.

A further subject of the invention is constituted by a shampoo and/or a hair care agent comprising one of the abovementioned inventive perhydrolases. Ingredients according to the invention that are suitable for agents of this subject of the invention, are described below in detail.

The shampoos and/or hair care products as well as bubble baths, shower baths, creams, gels, lotions, alcoholic and aqueous-alcoholic solutions, emulsions, wax/fatty masses, sticks, powders or salves that include perhydrolases, can contain mild surfactants, oils, emulsifiers, greases, pearlescent waxes, consistence providers, thickeners, polymers, silicone compounds, fats, waxes, stabilizers, biogenetic active principles, deodorants, antiperspirants, anti-dandruff agents, film formers, swelling agents, UV-light protection factors, antioxidants, hydrotropes, conserving agents, insect repellants, sun tans, solubilizers, perfume oils, colorants and the like as auxiliaries and additives.

Typical examples of suitable mild, i.e. particularly skin-compatible surfactants are fatty alcohol polyglycol ether sulfonates, monoglyceride sulfates, mono and/or dialkylsulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein-fatty acid condensates, the last preferably on the basis of wheat proteins.

The following can be considered as oils, for example: Guerbet alcohols based on fatty alcohols with 6 to 18, preferably 8 to 10 carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, such as for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In addition, suitable esters are esters of linear $C_6$-$C_{22}$-fatty acids with branched alcohols, especially 2-ethylhexanol, esters of hydroxycarboxylic acids with linear or branched $C_6$-$C_{22}$-fatty alcohols, especially dioctyl malate, esters of linear and/or branched fatty acids with polyhydroxy alcohols (e.g. propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{18}$-fatty alcohols and/or Guerbet alcohols with aromatic carboxylic acids, especially benzoic acid, esters of $C_2$-$C_{12}$-dicarboxylic acids with linear or branched alcohols with 1 to 22 carbon atoms or polyols with 2 to 10 carbon atoms and 2 to 6 hydroxyl groups, vegetal oils, branched primary alcohols, substituted cyclohexanes, linear and branched $C_6$-$C_{22}$-fatty alcohol carbonates, Guerbet carbonates, esters of benzoic acid with linear and/or branched $C_6$-$C_{22}$-alkohols (e.g. Finsolv® TN), linear or branched, symmetrical or unsymmetrical dialkyl ethers with 6 to 22 carbon atoms per alkyl group, ring opening products of epoxidized fatty acid esters with polyols, silicone oils and/or aliphatic or naphthenic hydrocarbons, such as, for example squalane, squalene or dialkylcyclohexanes.

Emulsifiers can be selected, for example, from nonionic surfactants from at least one of the following groups:
(1) Addition products of 2 to 30 moles ethylene oxide and/or 0 to 5 moles propylene oxide to fatty alcohols with 8 to 22 carbon atoms, to fatty acids with 12 to 22 carbon atoms, to alkyl phenols with 8 to 15 carbon atoms in the alkyl group as well as alkylamines with 8 to 22 carbon atoms in the alkyl radical;
(2) $C_{12/18}$-fatty acid mono and diesters of addition products of 1 to 30 moles ethylene oxide on glycerol;
(3) Glycerol mono and diesters and sorbitol mono and diesters of saturated and unsaturated fatty acids with 6 to 22 carbon atoms and their ethylene oxide addition products;
(4) Alkyl- and/or alkenyl mono and -oligoglycosides with 8 to 22 carbon atoms in the alk(en)yl radical and their ethoxylated analogs;
(5) Addition products of 15 to 60 moles ethylene oxide on castor oil and/or hydrogenated castor oil;
(6) Polyol esters and especially polyglycerol esters;
(7) Addition products of 2 to 15 moles ethylene oxide on castor oil and/or hydrogenated castor oil;
(8) Partial esters based on linear, branched, unsaturated or saturated $C_{6/22}$-fatty acids, ricinoleic acid as well as 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) as well as polyglucosides (e.g. cellulose);
(9) Mono, di and trialkyl phosphates as well as mono, di and/or tri-PEG-alkylphosphates and salts thereof;
(10) Wool wax alcohols;
(11) Polysiloxane-polyalkyl-polyether copolymers or corresponding derivatives;
(12) Mixed esters of pentaerythritol, fatty acids, citric acid and fatty alcohol according to the Patent DE 1165574 and/or mixed esters of fatty acids with 6 to 22 carbon atoms, methyl glucose and polyols, preferably glycerol or polyglycerol,
(13) Polyalkylene glycols and
(14) Glycerol carbonate.

The addition products of ethylene oxide and/or propylene oxide on fatty alcohols, fatty acids, alkyl phenols, glycerol mono and diesters as well as sorbitol mono and diesters of fatty acids or on castor oil represent known, commercially available products. They can be considered as mixtures of homologs, whose mean degree of alkoxylation corresponds to the ratio of amounts of ethylene oxide and/or propylene oxide, used for the addition reaction, and that of the substrate. $C_{12/18}$ fatty acid mono and diesters of addition products of ethylene oxide on glycerol are known from DE 2024051 as greasing agents for cosmetic preparations.

Alkyl and/or alkenyl mono and oligoglycosides, their manufacture and use are known from the prior art. Their manufacture results particularly from the reaction of glucose or oligosaccharides with primary alcohols containing 8 to 18 carbon atoms. As far as the glycoside radicals are concerned, both monoglycosides, in which a cyclic sugar radical is glycosidically linked to the fatty alcohol, and also oligomeric glycosides, with a degree of oligomerization of preferably about 8, are suitable. In this context, the oligomerization degree is a statistical mean value based on the typical homolog distribution of such technical products.

Typical examples of suitable polyglycerol esters are polyglyceryl-2 dipolyhydroxystearate (Dehymuls® PGPH), polyglycerol-3-diisostearate (Lameform® TGI), polyglyceryl-4-isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate and mixtures thereof.

Moreover, zwitterionic surfactants can be used as emulsifiers. Zwitterionic surfactants are designated as those surface-active compounds that carry at least a quaternary ammonium group and at least a carboxylate and a sulfonate group in the molecule. Particularly suitable zwitterionic surfactants are the so-called betaines such as the N-alkyl-N,N-dimethylammonium glycinates, for example the cocoalkyldimethylammonium glycinate, N-acylaminopropyl-N,N-dimethylammonium glycinates, for example the cocoacylaminopropyldimethylammonium glycinate, and 2-alkyl-3-carboxymethyl-3-hydroxyethyl imidazolines with 8 to 18 carbon atoms in each of the alkyl or acyl groups, as well as cocoacylaminoethylhydroxyethylcarboxymethyl glycinate. The known fatty acid derivative known under the CTFA-description Cocamidopropyl Betaine is particularly preferred. Similarly, ampholytic surfactants are suitable emulsifiers. The ampholytic surfactants are understood to include such surface-active compounds that apart from a $C_{8/18}$ alkyl or acyl group, contain at least one free amino group and at least one COOH or $SO_3H$ group in the molecule, and are able to form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycine, N-alkyltaurines, N-alkylsarcosinea, 2-alkyl-aminopropionic acids und alkylaminoacetic acids with about 8 to 18 C-atoms in each alkyl group. Particularly preferred ampholytic surfactants are N-cocoalkylamino propionate, cocoacylaminoethylamino propionate and $C_{12/18}$-acyl sarcosine. Beside the ampholytics, the quaternary emulsifiers can also be considered, wherein the esterquats, preferably methylquaternized difatty acid triethanolamine ester salts are particularly preferred.

As greasing agents, substances such as lanolin and lecithin, as well as polyethoxylated or acylated lanolin and lecithin derivatives, polyol fatty acid esters, monoglycerides and fatty acid alkanolamides can be used, the last ones serving as foam stabilizers at the same time.

Pearlescent waxes include: alkylene glycol esters, especially ethylene glycol distearate; fatty acid alkanolamides, especially cocofatty acid diethanolamide; partial glycerides, especially monoglyceride of stearic acid; esters of polyfunctional, optionally hydroxy-substituted carboxylic acids with fatty alcohols with 6 to 22 carbon atoms, especially long chain esters of tartaric acid; solids, such as, for example fatty alcohols, fatty ketones, fatty aldehydes, fatty ethers and fatty carbonates, which have a total of at least 24 carbon atoms, especially lauron and distearyl ether; fatty acids like stearic acid, hydroxystearic acid or behenic acid, ring opened products of olefin epoxides having 12 to 22 carbon atoms with fatty alcohols with 12 to 22 carbon atoms and/or polyols having 2 to 15 carbon atoms and 2 to 10 hydroxyl groups and mixtures thereof.

Consistence agents primarily include fatty alcohols or hydroxyfatty alcohols having 12 to 22 and preferably 16 to 18 carbon atoms, besides partial glycerides, fatty acids or hydroxyfatty acids. A combination of these materials with alkyl oligoglucosides and/or fatty acid N-methylglucamides of the same chain length and/or polyglycerol poly-12-hydroxystearates is preferred.

Suitable thickeners are for example aerosil types (hydrophilic silicic acids), polysaccharides, especially xanthane gum, guar-guar, agar-agar, alginates and tyloses, carboxymethyl cellulose and hydroxyethyl cellulose, in addition, higher molecular polyethylene glycol mono- and-diesters of fatty acids, polyacrylates, (e.g. Carbopole® from Goodrich or Synthalene® from Sigma), polyacrylamides, Polyvinyl alcohol and polyvinyl pyrrolidone, surfactants such as ethoxylated fatty acid glycerides, esters of fatty acids with polyols such as pentaerythritol or trimethylolpropane, fatty alcohol ethoxylates with narrowed homolog distribution or alkyl oligoglucosides as well as electrolytes like cooking salt and ammonium chloride.

Exemplary suitable cationic polymers are cationic cellulose derivatives, such as a quaternized hydroxyethyl cellulose, available under the trade name Polymer JR 400® from Amerchol, cationic starches, copolymers of diallylammonium salts and acrylamides, quaternized vinyl pyrrolidone/vinyl imidazole polymers, like e.g. Luviquat® (BASF), condensation products of polyglycols with amines, quaternized collagen polypeptides, like for example, lauryldimonium hydroxypropyl hydrolyzed collagen (Lamequat®L/Grünau), quaternized wheat polypeptides, polyethylene imines, cationic silicone polymers, such as amidomethicone, copolymers of adipic acid and dimethylaminohydroxypropyldiethylene triamine (Cartaretine®/Sandoz), copolymers of acrylic acid and dimethyldiallylammonium chloride (Merquat(D 550/Chemviron), polyaminopolyamides, such as e.g. described in FR 2252840 A as well as their crosslinked water-soluble polymers, cationic chitin derivatives such as e.g. quaternized chitosan, optionally microcystallinically dispersed, condensation products of dihaloalkylenes, such as e.g. dibromobutane with bis-dialkylamines, such as e.g. bis-dimethylamino-1,3-propane, cationic guar gum, such as e.g. Jaguar® CBS, Jaguar® C-17, Jaguar® C-16 from Celanese company, quaternized ammonium polymers, such as e.g. Mirapol® A-1 5, Mirapol® AD-1, Mirapol® AZ-I from the Miranol company.

Anionic, zwitterionic, amphoteric and nonionic polymers include, for example, vinyl acetate-crotonic acid copolymers, vinyl pyrrolidone-vinyl acrylate copolymers, vinyl acetate-butyl maleate-isobornyl acrylate copolymers, methyl vinyl ether-maleic anhydride copolymers and their esters, uncrosslinked polyacrylic acids and those crosslinked with polyols, acrylamidopropyltrimethylammonium chloride-acrylate copolymers, octylacylamide-methyl methacrylate-tert.-butylaminoethyl methacrylate-2-hydroxypropyl methacrylate copolymers, polyvinyl pyrrolidone, vinyl pyrrolidone-vinyl acetate copolymers, vinyl pyrrolidone-dimethylaminoethyl methacrylate-vinyl caprolactam terpolymers as well as optionally derivatized cellulose ethers and silicones.

Exemplary suitable silicone compounds are dimethylpolysiloxanes, methylphenylpolysiloxanes, cyclic siloxanes as well as amino-, fatty acid-, alcohol-, polyether-, epoxy-, fluorine-, glycoside- and/or alkyl modified silicone compounds, which may be both liquid or also resinous at room temperature. Simethicones, which are mixtures of dimethicones having an average chain length of 200 to 300 dimethylsiloxane units and hydrated silicates, are also suitable. A detailed review of suitable volatile silicones is found in Todd et al., Cosm. Toil. 91, 27 (1976).

Typical examples of fats are glycerides; waxes include inter alia natural waxes such as e.g. candelilla wax, carnauba wax, japan wax, esparto grass wax, cork wax, guarum wax, rice oilseed wax, raw sugar wax, ouricury wax, montan wax, beeswax, shellac wax, spermaceti, lanolin (wool wax), fowl fat, ceresine, ozokerite, petrolatum, paraffin waxes microwaxes; chemically modified waxes (hard waxes), such as e.g. montan ester waxes, sasol waxes, hydrogenated jojoba waxes as well as synthetic waxes, such as e.g. polyalkylene waxes and polyethylene glycol waxes.

Metal salts of fatty acids, such as e.g. magnesium-, aluminum- and/or zinc stearate or ricinoleate can be used as stabilizers.

Biogenetic active agents are understood to mean for example, tocopherol, tocopherol acetate, tocopherol palmitate, ascorbic acid, desoxyribonucleic acid, retinol, bisabolol, allantoin, phytanetriol, panthenol, AHA-acids, amino acids, ceramides, pseudoceramides, essential oils, plant extracts and vitamin complexes.

Cosmetic deodorants act against body odors, masking or eliminating them. Body odors result from the action of skin bacteria on apocrine sweat, whereby unpleasant smelling degradation products are formed. Accordingly, deodorants contain active principles, which act as germicides, enzyme inhibitors, odor absorbers or odor masks.

As germicides, which can be optionally added to the cosmetics according to the invention, basically all substances that are active against gram-positive bacteria are suitable, such as e.g. 4-hydroxybenzoic acid and its salts and esters, N-(4-chlorophenyl)-N'-(3,4-dichlorophenyl) urea, 2,4,4'-trichloro-2'-hydroxydiphenyl ether (Triclosan), 4-chloro-3,5-dimethylphenol, 2,2'-methylene-bis(6-bromo-4-chlorophenol), 3-methyl-4-(1-methylethyl) phenol, 2-benzyl-4-chlorophenol, 3-(4-chlorophenoxy)-1,2-propanediol, 3-iodo-2-propinylbutyl carbamate, chlorhexidine, 3,4,4'-trichlorocarbanilide (TTC), antibacterial fragrances, menthol, mint oil, phenoxyethanol, glycerol monolaurate (GML), diglycerol monocaprinate (DMC), salicylic acid-N-alkylamides such as, e.g. salicylic acid n-octylamide or salicylic acid n-decylamide.

Enzyme inhibitors can also be added to the inventive cosmetics. Examples of possible suitable enzyme inhibitors are esterase inhibitors. Trialkyl citrates are preferred, such as trimethyl citrate, tripropyl citrate, triisopropyl citrate, tributyl citrate and particularly triethyl citrate (Hydagen® CAT, Henkel KGaA, Düsseldorf/Germany). The substances inhibit the enzymatic activity and thereby reduce the odor formation. Additional substances that can be considered as esterase inhibitors are sterol sulfates or phosphates, such as e.g. lanosterin-, cholesterin-, campesterin-, stigmasterin- and sitosterin sulfate or phosphate, dicarboxylic acids and their esters, such as e.g. glutaric acid, monoethyl glutarate, diethyl glutarate, adipic acid, monoethyl adipate, diethyl adipate, malonic acid and diethyl malonate, hydroxycarboxylic acids and their esters such as e.g. citric acid, malic acid, tartaric acid or diethyl tartrate, as well as zinc glycinate.

Suitable odor absorbers are substances, which take up the odor forming compounds and firmly block them. They reduce the partial pressures of the individual components and thus also reduce their rate of propagation. It is important that the perfumes remain unaffected by this. Odor absorbers have no activity against bacteria. They comprise as the major component, for example, a complex zinc salt of ricinoleic acid or special, largely odor-neutral fragrances, which are known to the expert as fixing agents, such as e.g. extracts of labdanum or styrax or specific abietic acid derivatives. Fragrances or perfume oils act as masking agents and in addition to their function as masking agents, lend the deodorants their particular fragrance. Exemplary perfume oils include mixtures of natural and synthetic aromas. Natural aromas are extracts of flowers, stalks and leaves, fruits, fruit skins, roots, branches, herbs and grasses, needles and twigs as well as resins and balsams. In addition, animal materials such as e.g. civet and castoreum can be considered. Typical synthetic aroma compounds are products of the type of the esters, ethers, aldehydes, ketones, alcohols and hydrocarbons.

Antiperspirants reduce sweat formation by influencing the activity of the ecrinal sweat glands and thereby act against armpit moisture and body odor. Aqueous or anhydrous formulations of antiperspirants typically contain the following ingredients:
  (a) astringent principles,
  (b) oil components
  (c) nonionic emulsifiers,
  (d) co emulsifiers,
  (e) structurants,
  (f) auxiliaries such as e.g. thickeners or complexing agents and/or
  (g) non-aqueous solvents such as e.g. ethanol, propylene glycol and/or glycerol.

Salts of aluminum, zirconium or zinc are the main suitable astringent antiperspirant active principles. Such suitable antihydrotically active substances are e.g. aluminum chloride, hydrated aluminum chloride, hydrated aluminum dichloride, hydrated aluminum sesquichloride and their complexes e.g. with 1,2-propylene glycol, aluminum hydroxy allantoinate, aluminum chloride tartrate, aluminum-zirconium-trichlorohydrate, aluminum-zirconium tetrachlorohydrate, aluminum-zirconium pentachloro hydrate and their complexes e.g. with amino acids such as glycine.

The antiperspirants can also comprise standard oil-soluble and water-soluble auxiliaries in minor amounts. Such oil-soluble auxiliaries can be for example:
  anti-inflammatory, skin protecting or fragrant essential oils,
  synthetic skin-protecting active substances and/or
  oil-soluble perfume oils.

Typical water-soluble additives are e.g. conservers, water-soluble aromas, pH adjustors, e.g. buffer mixtures, water-soluble thickeners, e.g. water-soluble natural or synthetic polymers such as e.g. xanthane gum, hydroxyethyl cellulose, polyvinyl pyrrolidone or high-molecular polyethylene oxides.

Climbazole, octopirox and zinc pyrethion can be used as anti-dandruff agents.

Usable film builders are for example, chitosan, microcrystalline chitosan, quaternized chitosan, polyvinyl pyrrolidone, vinyl pyrrolidone-vinyl acetate copolymers, polymers of the acrylic acid series, quaternized cellulose derivatives, collagen, hyaluronic acid or its salts and similar compounds.

As swelling agents for the aqueous phase, montmorillonite, mineral clays, Pemulen® as well as Carbopol types (Goodrich) can be used. Additional suitable polymers or swelling agents can be found in the review by R. Lochhead in Cosm. Toil. 108, 95 (1993).

The UV light protective factors are understood for example to be organic substances (protective light filters) that are liquid or solid at room temperature and which are able to absorb UV radiation and emit the resulting energy in the form of longer wavelength radiation, for example as heat. UVB filters can be oil-soluble or water-soluble. As oil-soluble substances, the following may be cited:
  3-benzylidenecamphor or 3-benzylidenenorcamphor and its derivatives, for example 3-(4-methylbenzylidene) camphor, as described in the EP 0693471 B 1;
  4-aminobenzoic acid derivatives, preferably 4-(dimethylamino)benzoic acid, 2-ethylhexyl ester, 4-(dimethylamino)benzoic acid, 2-octyl ester and 4-(dimethylamino)benzoic acid, amyl ester;
  esters of cinnamic acid, preferably 4-methoxycinnamic acid, 2-ethylhexyl ester, 4-methoxycinnamic acid, propyl ester, 4-methoxycinnamic acid, isoamyl ester, 2-cyano-3,3-phenylcinnamic acid, 2-ethylhexyl ester (octocrylene);
  esters of salicylic acid, preferably salicylic acid, 2-ethylhexyl ester, salicylic acid, 4-isopropylbenzyl ester, salicylic acid, homomenthyl ester;
  derivatives of benzophenone, preferably 2-hydroxy4-methoxybenzophenone, 2-hydroxy4-methoxy-4'-methylbenzophenone, 2,2'-dihydroxy-4-methoxybenzophenone;
  esters of benzalmalonic acid, preferably 4-methoxybenzmalonic acid, di-2-ethylhexylester;
  triazine derivatives, such as, for example 2,4,6-trianilino-(p-carbo-2'-ethyl-1'-hexyloxy)-1,3,5-triazine and octyl triazone, as described in EP 0818450 A1 or dioctyl butamidotriazone (UVasorb® HEB);

propane-1,3-dione, such as for example 1-(4-tert.-butylphenyl)-3-(4'-methoxyphenyl)propane-1,3-dione;

ketotricyclo(5.2.1.0) decane derivatives, as described in EP 0694521 B1.

Water-soluble substances include:

2-phenylbenzimidazole-5-sulfonic acid and its alkali-, earth alkali-, ammonium-, alkylammonium-, alkanolammonium- and glucammonium salts;

sulfonic acid derivatives of benzophenones, preferably 2-hydroxy4-methoxybenzophenone-5-sulfonic acid and its salts;

sulfonic acid derivatives of 3-benzylidenecamphor, as for example 4-(2-oxo-3bornylidenemethyl)benzene sulfonic acid and 2-methyl-5-(2-oxo-3-bornylidene) sulfonic acid and its salts.

Typical UV-A filters particularly include derivatives of benzoylmethane, such as, for example 1-(4'-tert.-butylphenyl)-3-(4'-methoxyphenyl)propane-1,3-dione, 4-tert.-butyl4'-methoxydibenzoylmethane (Parsol 1789), 1-phenyl-3-(4'-isopropylphenyl)-propane-1,3-dione as well as enamine compounds, as described in the DE 19712033 A1 (BASF). Naturally, the UV-A and UV-B filters can also be added as mixtures. Beside the cited soluble materials, insoluble, light protective pigments, namely finely dispersed, metal oxides or salts can also be considered for this task. Exemplary suitable metal oxides are particularly zinc oxide and titanium oxide and also oxides of iron, zirconium, silicon, manganese, aluminum and cerium as well as their mixtures. Silicates (talc), barium sulfate or zinc stearate can be added as salts. The oxides and salts are already used in the form of pigments for skin care and skin protecting emulsions and decorative cosmetics. Here, the particles should have a mean diameter of less than 100 nm, preferably between 5 and 50 nm and especially between 15 and 30 nm. They can be spherical, however elliptical or other shaped particles can also be used. The pigments can also be surface treated, i.e. hydrophilized or hydrophobized. Typical examples are coated titanium dioxides, such as, for example Titandioxid T 805 (Degussa) or Eusolex® T2000 (Merck). Hydrophobic coating agents preferably include trialkoxy octylsilanes or Simethicones. Sunprotection agents preferably contain micropigments or nanopigments. Micronized zinc oxide is preferably used. Further suitable UV light protection filters may be found in the review by P. Finkel in SöFW-Journal, Volume 122 (1996), p. 543.

As well as both above-cited groups of primary light protective materials, secondary light protective agents of the antioxidant type can also be used, which interrupt photochemical chain reactions that are propagated when the UV-radiation penetrates the skin. Typical examples are amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotinoides, carotines (e.g. α-carotine, β-carotine, lycopine) and their derivatives, chlorogenic acid and their derivatives, liponic acid and their derivatives (e.g. dihydroliponic acid), aurothioglucose, propylthiouracil and other thioles (e.g. thioredoxine, glutathione, cystein, cystine, cystamine and their glycosyl-, n-acetyl-, methyl-, ethyl-, propyl-, amyl-, butyl- and lauryl-, palmitoyl-, oleyl-, γ-linoleyl-, cholesteryl- and glyceryl esters) as well as their salts, dilauryl thiodipropionate, distearyl thiodipropionate, thiodipropionic acid and their derivatives (esters, ethers, peptides, lipids, nucleotides, nucleosides and salts) as well as sulfoximine compounds (e.g. buthioninesulfoximines, homocysteinsulfoximine, butionine sulfone, penta-, hexa-, heptathionine sulfoximine) in very minor compatible doses (e.g. pmol to μmol/kg), further (metal)-chelates (e.g. α-hydroxyfatty acids, palmitic acid, phytinic acid, lactoferrin), α-hydroxyacids (e.g. citric acid, lactic acid, malic acid), humic acid, gallic acid, gall extracts, bilirubin, biliverdin, EDTA, EGTA and their derivatives, unsaturated fatty acids and their derivatives (e.g. γ-linolenic acid, linolic acid, oleic acid), folic acid and their derivatives, ubiquinone and ubiquinol and their derivatives, vitamin C and derivatives (e.g. ascorbyl palmitate, Mg-ascorbyl phosphate, ascorbyl acetate), tocopheroles and derivatives (e.g. vitamin-E-acetate), vitamin A and derivatives (vitamin-A-palmitate) as well as coniferyl benzoate of benzoic resin, rutinic acid and their derivatives, α-glycosylrutine, ferula acid, furfurylideneglucitol, carnosine, butylhydroxytoluene, butylhydroxyanisol, nordihydroguajac resin acid, nordihydroguajaret acid, trihydroxybutyrophenone, uric acid and their derivatives, mannoses and their derivatives, superoxide-dismutase, zinc und its derivatives (e.g. ZnO, $ZnSO_4$) selenium and its derivatives (e.g. selenium-methionine), stilbenes and their derivatives (e.g. stilbene oxide, trans-stilbene oxide) and the inventive suitable derivatives (salts, esters, ethers, sugars, nucleotides, nucleosides, peptides and lipids) of these cited active substances.

To improve the flow properties, hydrotropes can also be added, such as, for example, ethanol, isopropyl alcohol, or polyols. Polyols, which are considered, possess preferably 2 to 15 carbon atoms and at least two hydroxyl groups. The polyols can comprise further functional groups, especially amino groups, or can be modified by nitrogen. Typical examples are glycerol;

alkylene glycols, such as, for example ethylene glycol, diethylene glycol, propylene glycol, butylene glycol, hexylene glycol as well as polyethylene glycols with an average molecular weight of 100 to 1000 Daltons;

technical oligoglycerol mixtures with a self condensation degree of 1.5 to 10 about like technical diglycerol mixtures with a diglycerol content of 40 to 50 wt. %;

methylol compounds, particularly like trimethylolethane, trimethylolpropane, trimethylolbutane, pentaerythritol and dipentaerythritol;

lower alkyl glucosides, particularly those with 1 bis 8 carbons in the alkyl radical, such as, for example methyl- and butyl glucoside;

sugar alcohols having 5 to 12 carbon atoms, such as, for example sorbitol or mannitol, sugars with 5 to 12 carbon atoms, such as, for example glucose or saccharose;

aminosugars, such as, for example glucamine;

dialcoholamines, like diethanolamine or 2-amino-1,3-propanediol.

Suitable preservatives are, for example phenoxyethanol, formaldehyde solution, parabene, pentanediol or sorbic acid as well as the further classes of materials described in Appendix 6, part A and B of the Cosmetic Regulation. Insect repellants include N,N-diethyl-m-toluamide, 1,2-pentanediol or ethyl butylacetylaminopropionate; suitable self tanning agents include dihydroxyacetone.

As perfume oils, the known mixtures of natural and synthetic aromas can be cited. Natural aromas are extracts of flowers (lilies, lavender, roses, jasmine, neroli, ylang ylang), stalks and leaves (geranium, patchouli, petit grain), fruits (aniseed, coriander, caraway, juniper), fruit skins (bergamot, lemons, oranges), roots (mace, angelica, celery, cardamom, costic, iris, calmus), wood (pine, sandal, guava, cedar, rose wood), herbs and grasses (tarragon, lemon grass, sage, thyme), needles and twigs (spruce, fir, scotch pine, larch), resins and balsam (galbanum, elemi, benzoin, myrrh, olibanum, opoponax). In addition, animal materials such as e.g. civet and castoreum can be considered. Typical synthetic aroma compounds are products of the type of the esters, ethers, aldehydes, ketones, alcohols and hydrocarbons.

As colorants, those substances suitable and approved for cosmetic purposes can be used, as summarized, for example in the publication "Kosmetische Färbemittel" of the Colorant Commission of the Deutsche Forschungsgemeinschaft, Verlag Chemie, Weinheim, 1984, p. 81-106. These colorants are typically used in concentrations of 0.001 to 0.1 wt. %, based on the total mixture.

The total content of auxiliaries and additives can be 1 to 50, preferably 5 to 40 wt. %, based on the composition. The manufacture of the composition can be made using customary cold or hot processes; preferably according to the phase inversion temperature method.

A further subject is constituted by oxidative colorants for dyeing keratin fibers, particularly hair, or by hair dyes, which comprise one of the previously described inventive perhydrolases, a hydrogen peroxide source and substrates for the perhydrolases. Keratin fibers are understood to mean wool, feathers, skins and particularly human hair.

The substrates for the use mentioned above are preferably selected from methyl, ethyl or glycerol esters of butyric, caproic or octanoic acid, and preferably from methyl esters of butyric, caproic and octanoic acid or trioctanoine, the methyl ester of butyric acid being especially preferred.

The hydrogen peroxide source is accordingly selected especially from sodium percarbonate, sodium perborate or a potassium monopersulfate triple salt, mixtures of percarbonate/potassium persulfate in a ratio of 1 to 3 (pH 5.5); percarbonate/potassium persulfate in a ratio of 1 to 1 (pH 7.5); percarbonate/potassium persulfate in a ratio of 3 to 1 (pH>9), with $H_2O_2$ being especially preferred.

For the production of oxidizing agents according to the invention, the oxidative dyestuff precursors and the perhydrolases are incorporated into a suitable aqueous carrier. Such carriers include, for example, thickened aqueous solutions, creams (emulsions), gels or surfactant-containing foaming preparations, for example shampoos or aerosol foams or other preparations that are suitable for use on the hair.

In principle, water-free powders are also suitable as carriers; in such a case the oxidative dye substance is usually dissolved or dispersed in water directly before use. Preferable carrier components include:

wetting agents and emulsifiers
thickening agents reducing agents (antioxidants)
hair-care additives
fragrances and
solvents such as, for example, water, glycols or low molecular weight alcohols.

Suitable wetting agents and emulsifiers include, for example, anionic, zwitterionic, amphoteric and non-ionic surfactants. Cationic surfactants can also be used to obtain specific effects.

Suitable thickening agents are water-soluble high molecular weight polysaccharide derivatives or polypeptides, for example, cellulose or starch ethers, gelatin, plant gums, biopolymers (xanthan gum) or water-soluble synthetic polymers, such as, for example, polyvinylpyrrolidone, polyvinyl alcohol, polyethylene oxide, polyacrylamide, polyurethane, polyacrylate and others.

Furthermore, surfactant-containing preparations can also be thickened by solubilization or emulsification of polar lipids. Examples of such lipids are, for example, fatty alcohols with 12-18 C atoms, (free) fatty acids with 12-18 C atoms, partial glycerides of fatty acid, sorbitan fatty acid esters, fatty acid alkanolamide, low molecular weight oxyethylated fatty acids or fatty alcohols, lecithins, sterines. Finally, it is also possible to produce carriers in gel form based on aqueous soap gels, for example from ammonium oleate.

Reducing agents (antioxidants), which are added to the carrier in order to prevent a premature oxidative reaction of the dye before its use on the hair, can be, for example, sodium sulfite or sodium ascorbate.

Hair care ingredients can include, for example, fats, oils or waxes in emulsified form, structuring additives, for example, glucose or pyridoxine, brightening components, for example, water-soluble proteins, protein degradation products, amino acids, water-soluble cationic polymers, silicones, vitamins, panthenol or plant extracts.

Finally, fragrances and solvents, for example, glycols such as 1,2 propylene glycol, glycerol, glycol ethers such as butyl glycol, ethyl diglycol or lower univalent alcohols such as ethanol or isopropanol, can also be ingredients.

In addition, other additives can also be present in order to improve the stability and usage properties of the oxidative dyes, for example, complexing agents such as EDTA, NTA or organophosphonates, swelling and penetrating agents, for example urea, guanidine, bicarbonates, buffer salts such as ammonium chloride, ammonium nitrate, ammonium sulfate or alkyl ammonium salts and propellants if required.

Dental care agents form a further subject of the invention, especially denture cleaners containing one of the previously described perhydrolases according to the invention, a source of hydrogen peroxide and a substrate for the perhydrolases. In particular, these agents bring about bleaching or disinfection of the articles in question.

The substrates for the use mentioned above are preferably selected from methyl, ethyl or glycerol esters of butyric, caproic or octanoic acid, and preferably from methyl esters of butyric, capric and octanoic acid or trioctane, with methyl esters of butyric acid being especially preferred.

The hydrogen peroxide source is accordingly selected especially from sodium percarbonate, sodium perborate or a potassium monopersulfate triple salt, mixtures of percarbonate/potassium persulfate in a ratio of 1 to 3 (pH 5.5); percarbonate/potassium persulfate in a ratio of 1 to 1 (pH 7.5); percarbonate/potassium persulfate in a ratio of 3 to 1 (pH>9), with $H_2O_2$ being especially preferred.

In the case of partial prostheses or dentures, presentation as denture cleaning tablets or as mouthwash or rinse or toothpaste is also suitable.

The mouth, tooth or denture care agents according to the invention can be available, for example as mouthwash, gel, liquid tooth cleaner, firm toothpaste, denture cleaner or denture adhesive cream.

For this it is necessary to incorporate the perhydrolases according to the invention within a suitable carrier.

For example, preparations in powder form or water-alcohol solutions can serve as carriers, which can contain 0 to 15 weight % ethanol, 1 to 1.5 weight % flavor oils and 0.01 to 0.5 weight % sweeteners for mouthwash or 15 to 60 weight % ethanol, 0.05 to 5 weight % flavor oils, 0.1 to 3 weight % sweeteners as well as other additives if required for mouthwash concentrates which are diluted with water before use. The concentration of the components must be selected to be high enough so that following dilution the concentration during use does not fall below the lower limit of the range mentioned.

Gels as well as more or less flowable pastes, which are squeezed out of flexible plastic containers or tubes and applied to the teeth with the aid of a toothbrush, can also serve as carriers. Such products contain higher quantities of wetting and binding agents or stabilizers and polishing agents. Furthermore, perfume oils, sweeteners and water are also contained in these preparations.

Wetting agents can include, for example, glycerol, sorbitol, xylite, propylene glycols, polyethylene glycols or mixtures of these polyols, especially polyethylene glycols with a molecular weight from 200 to 800 (from 400-2000). The preferred wetting agent is sorbitol in a quantity of 25-40 weight %.

Condensed phosphates in the form of their alkali salts, preferably in the form of the sodium or potassium salt, can be included as anti-tartar agents and as inhibitors of demineralization. Aqueous solutions of these phosphates react as alkalis due to hydrolytic effects. On addition of acid, the pH value of the mouth, tooth and/or denture care agents according to the invention is kept within the preferred range of 7.5-9.

A mixture of various condensed phosphates or hydrated salts of condensed phosphates can also be used. However, the specified quantities of 2-12 weight % refer to the anhydrous salts. The preferred condensed phosphate is a sodium or potassium tripolyphosphate in a quantity of 5-10% by weight of the composition.

A favored active ingredient is a caries-inhibiting fluorine compound, preferably from the fluoride or monofluorophosphate group in a quantity of 0.1-0.5 weight % fluorine. Suitable fluorine compounds include, for example, sodium monofluorophosphate ($Na_2PO_3F$), potassium monofluorophosphate, sodium or potassium fluoride, stannous fluoride or a fluoride of an organic amino compound.

Binding agents and stabilizers include, for example, natural and synthetic water-soluble polymers such as carrageenan, traganth, guar, starch and their non-ionic derivatives such as hydroxypropyl guar, hydroxyethyl starch, cellulose ethers such as hydroxyethyl cellulose or methylhydroxypropyl cellulose. Agar-agar, xanthan gum, pectins, water-soluble carboxyvinyl polymers (e.g. Carbopol® types), polyvinyl alcohol, polyvinyl pyrrolidone, high-molecular-weight polyethylene glycols (molecular weight 103 to 106 D) can also be used. Other materials suitable to control viscosity include layered silicates, for example montinorillonite, colloidal swelling silicas, e.g. aerogel silicas or pyrogenic silicas.

Polishing components can include all polishing agents that are known for this purpose, but preferably precipitated and gel silicas, aluminum hydroxide, aluminum silicate, aluminum oxide, aluminum oxide trihydrate, insoluble sodium metaphosphate, calcium pyrophosphate, dicalcium phosphate, chalk, hydroxyapatite, hydrotalcite, talcum, magnesium aluminum silicate (Veegum®), calcium sulfate, magnesium carbonate, magnesium oxide, sodium aluminum silicates, for example zeolite A or organic polymers, for example polymethacrylate. The polishing agents are preferably used in smaller quantities, for example 1-10 weight %.

The tooth and/or mouth care products according to the invention can have their organoleptic qualities improved by the addition of flavor oils and sweeteners. Flavor oils can include all natural and synthetic flavorings used in products for the care of mouth, teeth or dentures. Natural flavors can be used in the form of ethereal oils isolated from drugs or in the form of individual components isolated from the latter. Preferably, at least one flavor oil from the group of peppermint oil, curled mint oil, aniseed oil, caraway oil, eucalyptus oil, fennel oil, cinnamon oil, geranium oil, sage oil, thyme oil, marjoram oil, basil oil, citrus oil, wintergreen oil, or one or more synthetically produced components isolated from these oils should be included. The most important components of the abovementioned oils are, for example, menthol, carvol, anethole, cineol, eugenol, cinnamaldehyde, geraniol, citronellol, linalool, salvene, thymol, terpinene, terpinol, methyl chavicol and methyl salicylate. Other suitable flavorings include, for example, menthyl acetate, vanillin, ionone, linalyl acetate, rhodinol and piperitone. Natural sugars such as sucrose, maltose, lactose and fructose or synthetic sweeteners such as sodium saccharin, sodium cyclamate or aspartame can be used for sweetening.

Surfactants that can be used include alkyl- and/or alkenyl-(oligo)-glycosides in particular. Their manufacture and use as surfactants is well known for example from U.S. Pat. No. 3 839 318, U.S. Pat. No. 3,707,535, U.S. Pat. No. 3,547,828, DE-A-19 43 689, DE-A-20 36 472 and DE-A-30 01 064 as well as from EP-A-77 167. With respect to glycoside residues, both monoglycosides (x=1), in which a pentose or hexose residue is glycosidically bound to a primary alcohol of 4-16 C atoms, and oligomeric glycosides with a degree of oligomerization of up to 10 are suitable. In this case the degree of oligomerization is a statistical average, which in such technical products usually forms the basis of a homologous distribution.

Suitable alkyl and/or alkenyl-(oligo)-glycosides are preferably of the formula $RO(C_6H_{10}O)_n$—H, in which R is an alkyl-and/or alkenyl group with 8 to 14 C atoms and x has an average value of 1 to 4. Alkyl-oligo-glucosides based on hydrogenated $C_{12/14}$ coconut alcohol with a DP of 1 to 3 are especially suitable. Alkyl- and/or alkenyl-glycoside surfactants can be used very economically, with amounts from 0.005 to 1 weight % already being sufficient.

In addition to the abovementioned alkyl-glucoside surfactants, other nonionic, amphoteric and cationic surfactants can be included, such as: fatty alcohol polyglycol ether sulfates, monoglyceride sulfates, monoglyceride ether sulfates, mono- and/or dialkyl sulfosuccinates, fatty acid isothionates, fatty acid sarcosinates, fatty acid taurides, fatty acid glutamates, ether carbonic acids, fatty acid glucamides, alkyl amido betaines and/or protein/fatty acid condensates, the latter preferably being based on wheat proteins. Especially when dissolving the least water-soluble flavor oils, a non-ionic solvent from the surfactant group may be necessary. Oxyethylated fatty acid glycerides, oxyethylated fatty acid sorbitol partial esters or fatty acid partial esters of glycerol or sorbitol oxethylates exemplify especially suitable substances for this purpose. Solvents from the oxethylated fatty acid glyceride group include, above all, all the addition products from 20 to 60 mol ethylene oxide with mono- and diglycerides of linear fatty acids having 12 to 18 C atoms or with triglycerides of hydroxy fatty acids such as oxystearic acid or ricinoleic acid. Other suitable solvents include oxyethylated fatty acid sorbitol partial esters; preferably addition products from 20 to 60 mol ethylene oxide with sorbitol monoesters and sorbitol diesters of fatty acids having 12 to 18 C atoms. Fatty acid partial esters of glycerol and sorbitol oxyethylates are also suitable solvents, preferably mono- and diesters of $C_{12}$-$C_{18}$ fatty acids and addition products of 20 to 60 mol ethylene with 1 mol glycerol or 1 mol sorbitol.

Mouth, tooth and/or denture care products according to the invention preferably contain addition products of 20 to 60 mol ethylene oxide with hardened or unhardened castor oil (namely with triglyceride of oxystearic or ricinoleic acid), with glycerol mono- and/or distearate or with sorbitol mono- and/or distearate to serve as solvents for the flavor oils that are included as required.

Examples of other customary additives to mouth, tooth and denture care products include,
  pigments, e.g. titanium dioxide, and/or colorants
  pH adjusters and buffers, e.g. sodium bicarbonate, sodium citrate, sodium benzoate, citric acid, phosphoric acid or acid salts, e.g. $NaH_2PO_4$ wound-healing and anti-inflammatory substances, e.g. allantoin, urea, panthenol, azulene or chamomile extract other anti-tartar substances e.g. organophosphates such as hydroxyethane diphosphonate or azacycloheptane diphosphonate preservatives, e.g. sorbic acid salts, p-hydroxybenzoic acid ester plaque inhibitors such as hexachlorophene, chlorhexidine, hexetidine, triclosan, bromchlorophene, phenyl salicylic acid ester.

A specific embodiment is the composition of a mouthwash, rinse, denture cleaner or dental adhesive.

For a preferred denture cleaner according to the invention, especially for denture-cleaning tablets and powders, in addition to the already listed ingredients for mouth, tooth and/or denture care products, per-compounds such as peroxoborate, peroxomonosulfate or percarbonate are also suitable. They have the advantage that in addition to a bleaching effect they simultaneously act to deodorize and/or disinfect. Such percompounds are used in denture cleaners at between 0.01 and 10 weight %, especially at between 0.5 and 5 weight %.

Enzymes, e.g. proteases and carbohydrase, are also suitable ingredients for the degradation of proteins and carbohydrates. The pH value can be in the range pH 4 to 12, and especially in the range pH 5 to pH 11.

Still other additives are required for denture cleaning tablets, for example materials that cause fizzing, e.g. $CO_2$-liberating substances such as sodium bicarbonate, fillers such as sodium sulfate or dextrose, lubricants, e.g. magnesium stearate, flow regulators such as colloidal silicon dioxide and granulating agents such as the already mentioned high-molecular-weight polyethylene glycols or polyvinyl pyrrolidone.

Denture fixative agents can be offered as powders, creams, films or liquids and they assist denture adhesion. Materials from natural and synthetic sources are suitable as the active agents. In addition to alginates, natural materials include plant gums such as gum arabic, traganth gum and karaya gum as well as natural rubber. Particular use is made of alginates and synthetic materials such as sodium carboxymethylcellulose, high-molecular-weight ethylene oxide copolymers, salts of poly(vinyl ether-co-maleic acid) and polyacrylamides.

Hydrophobic bases are particularly suitable as additives for paste and liquid products, especially hydrocarbons such as white vaseline (DAB—German Pharmacopoeia) or mineral oil.

The following examples describe the invention without however restricting it.

EXAMPLES

All molecular biological procedures are according to standardized methods as given, for example, in the manual by Fritsch, Sambrook and Maniatis, "Molecular cloning: a laboratory manual", Cold Spring Harbor Laboratory Press, New York, 1989, or comparable relevant works. Enzymes and kits were used according to the manufacturer's instructions.

Example 1

Expression of the Subtilisin Carlsberg protease from *Bacillus licheniformis* DSM 641

The region coding for subtilsin Carlsberg protease, including a promoter sequence, was amplified by means of PCR from the chromosomal DNA of *Bacillus licheniformis*— Strain DSM 461 obtained from the Deutschen Sammlung von Mikroorganismen und Zellkulturen GmbH, Mascheroder Weg 1b, 38124 Braunschweig. The reaction took place with the use of Taq-Polymerase from Gibco in an appropriate reaction preparation according to the following PCR program: denaturation at 94° C., 4 min; 30 cycles 94° C., 30 s, 50° C., 30 s, 72° C., 100 s and finally 72° C., 7 min. The oligonucleotides PSC-s and PSC-as (SEQ ID Nos. 19 and 20) were both used as a PCR primer.

The amplicon obtained was cleaved with the AvaI restriction endonuclease and was cloned into the pBC16 vector (available from Deutschen Sammlung von Mikroorganismen und Zellkulturen GmbH as Number 4424; see FIG. 1), which was also linearized with AvaI, to produce the pBC-SC vector (see FIG. 2) and then transformed according to a standard protoplast transformation protocol in *Bacillus subtilis* DB 104 (Kawamura und Doi (1984), J. Bacteriol., Vol 160 (1), p. 442-444).

The transformants were first regenerated on tetracycline-containing DM3 medium, pH 7.3 (8 g/l agar, 0.5 M succinic acid, 3.5 g/l $K_2HPO_4$, 1.5 g/l $KH_2PO_4$, 20 mM $MgCl_2$, 5 g/l casaminoacids, 5 g/l yeast extract, 6 g/l glucose, 0.1 g/l bovine serum albumin, 15 mg/l tetracycline) and then inoculated onto tetracycline-containing TBY skimmed milk plates (10 g/l trypton, 5 g/l yeast, 5 g/l NaCl, 15 g/l agar, 10 g/l milk powder, 15 mg/l tetracycline).

Single colonies from this culture were transferred to an agar-free, but otherwise identical, liquid medium and cultured at 37° C. in standardized conditions.

Example 2

Production of Perhydrolases from Subtilisin Carlsberg Using Error-Prone Mutagenesis Insert-containing plasmids were isolated by routine methods from a liquid culture established according to Example 1 and subjected to error-prone-mutagenesis.

The 100-μl starting mixture for the error-prone PCR contained 10 μl 10×-mutagenesis buffer (Taq buffer, Gibco), 4 μl dNTP-Mix (each 200 μmol/l end concentration), 1 μl dGTP/dATP (at 1 mmol/l), 0.2 μmol of each primer (see below for sequence), 5-15 ng template-(plasmid-) DNA (subtilisin Carlsberg), and 4 μl $MgCl_2$ (2 mmol/l), 0.7 μl $MnCl_2$ (0.35 mmol/l) and an appropriate quantity of $H_2O$. Then 5 U Taq-polymerase were added and the mixture was subjected to the following program of temperatures: denaturation at 94° C., 4 min; 30 cycles 94° C., 30 s, 50° C., 30 s, 72° C., 100 s and then 72° C., 7 min. In this way, both oligonucleotides, P300-S and PSC-as (SEQ ID NO. 21 and 20), were used as the PCR primer.

After termination of the reaction, the PCR product was purified using the Qiaquick PCR Purification Kit (Qiagen), cloned after restriction digestion in the NheI-/XhoI digestion site of the *Bacillus* expression vector pBC-SC and transformed by means of protoplast transformation in the commercially available *Bacillus subtilis* strain DB 104. The mutants that were obtained were first isolated from agar plates with TBY medium (10 g/l Trypton, 5 g/l yeast extract, 5 g/l NaCl) containing 15 μg/ml tetracycline and then cultured in a corresponding liquid medium at 37° C. under standardized conditions.

Example 3

Expression of Perhydrolase in *Bacillus subtilis* DB104 and Screening for Perhydrolytic and Hydrolytic Activity The mutants obtained according to Example 2 were incubated in 1 ml TBY medium (10 g/l Trypton, 5 μl yeast extract, 5 g/l NaCl) containing 15 μg/ml tetracycline for 48 h at 37° C. and 800 rpm.

The perhydrolases were purified from the culture supernatant in a batch process by means of affinity chromatography using Bacitracin (Aldrich, cat. no. 85,186-8) saturated Sepharose 4B (Pharmacia-Biotech, cat. no. 17-0430-01). For this purpose, 1 g Sepharose 4B was incubated with 100 mg Bacitracin in 100 mM NaHCO$_3$, 500 mM NaCl for 14 h at 4° C., followed by incubation for 2 h at 4° C. with 1 M ethanolamine and then diluted 1:4 with 100 mM ethanolamine, 10 mM CaCl$_2$, pH 6.5. Elution took place with 100 mM ethanolamine, containing 1 M NaCl and 25% isopropanol, pH 6.5. The culture supernatant purified in this manner was then used in the following tests.

The protein content was measured using the Micro-BCA Protein Assay Reagent Kit (Pierce), whereby 150 µl kit reagent was incubated with 75 µl water and 75 µl purified culture supernatant for 2 h at 37° C. and the protein content was calculated from the absorption at 562 nm using a calibration curve.

In order to evaluate hydrolytic (proteolytic) activity, 25 µl of the purified culture supernatant was mixed with 222.5 µl 20 mM Tris/HCl buffer pH 8.6 and 2.5 µl 110 mM suc-Ala-Ala-Pro-Phe-pNA (SEQ ID NO:24) (AAPF; Bachem Biochemika GmbH, Heidelberg, Germany) in DMSO. The increase in absorption at 405 nm was monitored for 10 minutes and converted into units (AAPF) per µg protein using a calibration curve.

In order to evaluate perhydrolytic activity, 100 µl of the purified culture supernatant was mixed with 30 µl 100 mM phosphate buffer pH 9, 50 µl 200 mM butyric acid methyl ester (Aldrich) and 20 µl 313 mM hydrogen peroxide and incubated for 15 min at 37° C. Then 50 µl 1.5 M acetic acid with 0.03 mg/ml potassium iodide were added as well as 50 µl 0.14 mM diammonium salt of 2,2'-azino-bis(3-ethylbenzthiazoline-6-sulfonic acid) (Sigma), the mixture was incubated for a further 10 min at room temperature and the absorption was measured at 405 nm. The values obtained were then converted using a calibration curve into ppm AO per µg protein, where 1 ppm AO corresponds to 62.5 µmol/l hydrogen peroxide.

Example 4

Hydrolytic (Proteolytic) And Perhydrolytic Activity Of The Discovered Perhydrolases The activity tests described in Example 3 were conducted on nine variants in total. The respective results are presented together in Table 1.

TABLE 1

Hydrolytic (proteolytic) and perhydrolytic activity of nine different perhydrolases according to the invention

| No. | Variant | proteolytic activity [U(AAPF)/µg] | perhydrolytic activity [ppm AO/µg] |
|---|---|---|---|
| control | Wild type | 0.8 | 0.33 |
| 1 | L89S/L216W/N217D | not done | 0.60 |
| 2 | L216W/N217D | 0.1 | 0.65 |
| 3 | T58A/L89S/L216W/N217D | not done | 0.57 |
| 4 | T58A/G117D/L216W/N217D | 0.1 | 0.7 |
| 5 | T58A/L89S/L216W | 0.2 | 0.98 |
| 6 | T58A/L89S/N96D/L216W | not done | 0.92 |

TABLE 1-continued

Hydrolytic (proteolytic) and perhydrolytic activity of nine different perhydrolases according to the invention

| No. | Variant | proteolytic activity [U(AAPF)/µg] | perhydrolytic activity [ppm AO/µg] |
|---|---|---|---|
| 7 | T58A/L216W | 0.1 | 0.92 |
| 8 | T58Q/L89S/L216W | 0.2 | 0.95 |
| 9 | L89S/L216W | 0.2 | 0.86 |

It is seen that the unchanged subtilisin Carlsberg (control), in addition to having proteolytic activity as expected (assessed here as 0.8 U(AAPF)/µg), also has a certain level of subsidiary perhydrolytic activity, which was determined in this reaction preparation to be 0.33 ppm AO per µg enzyme.

All nine perhydrolases that were tested, namely the special variants of subtilisin Carlsberg indicated, showed decreased protease activity. On the other hand, the amino acid substitutions resulted in increased perhydrolase (subsidiary) activity, which in this reaction preparation was determined to be at least 0.57 ppm AO per µg enzyme (prep. 3) and in the best case (prep. 5) 0.98 ppm AO per µg enzyme. In this last case, perhydrolytic activity was almost tripled through three substitutions at positions 58, 89 and 216 (T58A/L89S/L216W). To this extent, it is justifiable to speak of new perhydrolases.

Further control preparations with these variants and the following application-oriented examples confirmed this result.

Example 5

Bleaching of Typical Textile Stains with Perhydrolases

The perhydrolase-active supernatant obtained in Example 3 was used in a washing test at a concentration of 10 µg/ml in a solution of 50 mM phosphate buffer (pH 9) together with 100 mM butyric acid methyl ester and 313 mM hydrogen peroxide.

12.74 ml of this bleaching solution was applied to 10 cm$^2$ of commercial, bleachable stained cotton; the stains used were types E-114 (red wine) and E-167 (tea) from Eidgenössischen Material-Prüfungs- und Versuchsanstalt, St. Gallen, Switzerland (EMPA), or the corresponding self-applied stains from Henkel, namely A (red wine) and B (tea). These preparations were agitated for 30 minutes at 600 rpm and 30° C., rinsed in running water and allowed to air-dry at room temperature.

The brightness (L value) of the processed cotton fabric was measured using the Cm508d calorimeter (Minolta) and compared with the bleaching results from an enzyme-free preparation. The determination was carried out in light type D65 (daylight) with a measuring angle of 10°. The measured data were calibrated against L=100 (white) and L=0 (black).

The following delta L values, averaged over the respective measurements and presented in Table 2, can thus be derived for the previously described perhydrolases.

TABLE 2

Bleaching effect of nine different perhydrolases according to the invention on typical textile stains

| No. | II. Variant | Delta L (A) | Delta L (B) |
|---|---|---|---|
| Control | Wild type | 0.91 | 0.84 |
| 1 | L89S/L216W/N217D | 1.76 | 1.67 |
| 2 | L216W/N217D | 1.32 | 1.68 |

TABLE 2-continued

Bleaching effect of nine different perhydrolases according to the invention on typical textile stains

| No. | II. Variant | Delta L (A) | Delta L (B) |
|---|---|---|---|
| 3 | T58A/L89S/L216W/N217D | 1.34 | 1.39 |
| 4 | T58A/G117D/L216W/N217D | 1.77 | 1.58 |
| 5 | T58A/L89S/L216W | 1.71 | 1.82 |
| 6 | T58A/L89S/N96D/L216W | 1.96 | 2.07 |
| 7 | T58A/L216W | 2.38 | 2.00 |
| 8 | T58Q/L89S/L216W | 2.61 | 2.04 |
| 9 | L89S/L216W | 2.60 | 1.77 |

It is seen that all nine tested perhydrolases, namely those special variants of subtilisin Carlsberg, had a bleaching effect on standardized, commercially available textile stains that was clearly superior to that of the endogenous subsidiary activity of unaltered subtilisin Carlsberg. Control preparations with comparable stains confirmed this result.

Example 6

Bleaching of Typical Stains by Perhydrolases in Washing Agents

The supernatant with perhydrolase activity obtained in Example 3 was used in a washing test at a concentration of 10 μg/ml in a 10-ml solution containing 441 mg of a detergent formulation together with 100 mM butyric acid methyl ester and 313 mM hydrogen peroxide. The detergent formulation had the following composition: 0.3-0.5 weight % xanthan gum, 0.2-0.4 weight % antifoaming agent, 6-7 weight % glycerol, 0.3-0.5 weight % ethanol, 4-7 weight % FAEOS, 24-28 weight % nonionic surfactant (FAEO, APG, and others), 1 weight % boric acid, 1-2 weight % sodium citrate× 2H₂O, 2-4 weight % caustic soda, 14-16 weight % coconut fatty acids, 0.5 weight % HEDP, 0-0.4 weight % PVP, 0-0.05 weight % optical brighteners, 0-0.001 weight % colorings, 0-2 weight % fragrance, remainder: water and concomitant substances.

12.74 ml of this bleaching solution was applied to 10 cm² of commercial, bleachable stained cotton; the stains used were, as in the previous example, types E-114 (red wine) and E-167 (tea) from Eidgenössischen Material-Prüfungs- und Versuchsanstalt, St. Gallen, Switzerland (EMPA), or the corresponding self-applied stains from Henkel, namely A (red wine) and B (tea). These preparations were agitated for 30 minutes at 600 rpm and 30° C., rinsed in running water and allowed to air-dry at room temperature.

The brightness (L value) of the processed cotton fabric was again measured using the Cm508d calorimeter (Minolta) and compared with the bleaching results from an enzyme-free preparation. The determination was carried out in light type D65 (daylight) with a measuring angle of 10°. The measured data were calibrated against L=100 (white) and L=0 (black).

The following delta L values, averaged over the respective measurements and presented in Table 3, can thus be derived for the previously described perhydrolases.

TABLE 3

Bleaching effect of five different perhydrolases according to the invention, incorporated into a detergent formulation, on typical fabric stains

| No. | III. Variant | Delta L (A) | Delta L (B) |
|---|---|---|---|
| Control | Wild type | 0.44 | 0.26 |
| 1 | L89S/L216W/N217D | 0.64 | 0.69 |
| 2 | L216W/N217D | 1.06 | 0.67 |
| 3 | T58A/L89S/L216W/N217D | 1.09 | not done |
| 4 | T58A/G117D/L216W/N217D | 0.98 | 0.47 |
| 7 | T58A/L216W | 1.27 | 0.92 |

It is seen that all perhydrolases tested within a detergent formulation containing, amongst other ingredients, a surfactant and builder, on standardized, commercially available textile stains have a bleaching effect that is clearly superior to that of the endogenous subsidiary activity of unaltered subtilisin Carlsberg. Control preparations with comparable stains confirmed this result.

We claim:

1. A bodycare product; shampoo; hair care product; hair dye; hair bleach; oral care product; tooth care product; denture care product; cosmetic preparation; textile detergent; cleaning agent; rinsing agent; hand washing detergent; hand dishwashing detergent; machine dishwashing detergent; disinfectant; or agent for bleaching or disinfecting filter media, textile, fur, paper, skin, or leather comprising a perhydrolase comprising the amino acid sequence spanning positions +1 to +274 of SEQ ID NO:23 having a L216W substitution and optionally having one or more amino acid substitutions at positions 11, 15, 21, 38, 50, 54, 58, 77, 83, 89, 93, 96, 107, 117, 120, 134, 135, 136, 140, 147, 150, 154, 155, 160, 161, 171, 179, 180, 181, 194, 205, 208, 213, 217, 238, 239, 251, 253, 257, or 261.

2. A perhydrolase comprising the amino acid sequence spanning positions +1 to +274 of SEQ ID NO:23 having a L216W substitution and optionally having one or more amino acid substitutions at positions 11, 15, 21, 38, 50, 54, 58, 77, 83, 89, 93, 96, 107, 117, 120, 134, 135, 136, 140, 147, 150, 154, 155, 160, 161, 171, 179, 180, 181, 194, 205, 208, 213, 217, 238, 239, 251, 253, 257, or 261.

3. The perhydrolase of claim 2 wherein the one or more optional amino acid substitutions are at positions 11, 58, 77, 89, 96, 117, 120, 134, 135, 136, 140, 147, 150, 161, 208, 217, or 238.

4. The perhydrolase of claim 3 wherein the one or more optional amino acid substitutions are at positions 58, 89, 96, 117, or 217.

5. The perhydrolase of claim 4 wherein the one or more optional amino acid substitutions are T58A, T58Q, L89S, N96D, G117D, or N217D.

6. The perhydrolase of claim 2 comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

7. A nucleic acid encoding a perhydrolase comprising the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17.

8. A vector comprising the nucleic acid of claim 7.

9. A host cell that expresses a perhydrolase comprising the vector of claim 8.

10. The host cell of claim 9 wherein the host cell is a bacterium that secretes the perhydrolase from the cell.

11. The host cell of claim 10 wherein the host cell is a *Bacillus licheniformis, Bacillus amyloliquefaciens, Bacillus subtilis,* or *Bacillus alcalophilus* cell.

12. The host cell of claim 9 wherein the host cell is a eukaryotic cell that posttranslationally modifies the perhydrolase.

13. A method for producing percarboxylic acid in situ comprising reacting the perhydrolase of claim 2 with a substrate in the presence of hydrogen peroxide.

14. A detergent or bleaching composition comprising a bleaching system that produces percarboxylic acid and comprises the perhydrolase of claim 2, a hydrogen peroxide source, and a substrate for the perhydrolase, and optionally comprises a synthetic surfactant, organic builder, or inorganic builder.

15. The detergent or bleaching composition of claim 14 wherein the substrate for the perhydrolase is a methyl, ethyl or glycerol ester of butyric, caproic or octanoic acid.

16. The detergent or bleaching composition of claim 15 wherein the substrate for the perhydrolase is methyl butyrate, methyl caproate, methyl octanoate, or trioctanoin.

17. The detergent or bleaching composition of claim 14 wherein the hydrogen peroxide source is sodium percarbonate, sodium perborate triple salt, potassium monopersulfate triple salt, a 1:3 mixture of percarbonate and potassium persulfate, a 1:1 mixture of percarbonate and potassium persulfate, a 3:1 mixture of percarbonate and potassium persulfate, or $H_2O_2$.

18. The detergent or bleaching composition of claim 14 wherein the detergent or bleaching composition exhibits a perhydrolytic activity of about 0.05 to about 1.2 ppmAO/µg.

19. The detergent or bleaching composition of claim 14 wherein the detergent or bleaching composition is in the form of a tablet, pellets, a flowable powder with a bulk density of 300 g/l to 1200 g/l, a paste, a liquid, a non-aqueous paste, or a non-aqueous liquid.

20. The detergent or bleaching composition of claim 14 wherein at least one of the perhydrolase, the perhydrolase substrate, and the hydrogen peroxide source is enclosed in a substance that is impermeable to the perhydrolase, the perhydrolase substrate, and the hydrogen peroxide source at room temperature or in the absence of water, which substance becomes permeable to the perhydrolase, the perhydrolase substrate, and the hydrogen peroxide source under the conditions of use of the detergent or bleaching composition.

21. The detergent or bleaching composition of claim 14 further comprising
   a surfactant,
   a water-soluble, water-dispersible inorganic builder material,
   a water-soluble organic builder substance,
   a solid inorganic or organic acid or acid salt,
   a heavy metal complexing agent,
   a graying inhibitor,
   a dye transfer inhibitor, and
   a foam inhibitor.

22. An oxidation dye for dying keratin fibers comprising the perhydrolase of claim 2, a hydrogen peroxide source, and a substrate for the perhydrolase.

23. An agent for denture care comprising the perhydrolase of claim 2, a hydrogen peroxide source, and a substrate for the perhydrolase.

* * * * *